(12) United States Patent
Thommen et al.

(10) Patent No.: US 11,712,264 B2
(45) Date of Patent: Aug. 1, 2023

(54) MULTI-SHIELD SPINAL ACCESS SYSTEM

(71) Applicant: Medos International Sarl, Le Locle (CH)

(72) Inventors: Daniel Thommen, Lestal (CH); Joern Richter, Kandern (DE); Michael Wang, North Miami, FL (US); Richard Assaker, Kain (BE); Richard Fessler, Winnetka, IL (US); Christoph Mehren, Munich (DE); Seang Beng Tan, Clementi (SG); William Taylor, Del Mar, CA (US); Eric Buehlmann, Duxbury, MA (US); Michael White, Liestal (CH); Piet Hinoul, Basking Ridge, NJ (US); Richard Kocharian, Princeton, NJ (US)

(73) Assignee: Medos International Sarl, Le Locle (CH)

(*) Notice: Subject to any disclaimer, the term of this patent is extended or adjusted under 35 U.S.C. 154(b) by 0 days.

(21) Appl. No.: 17/159,129

(22) Filed: Jan. 26, 2021

(65) Prior Publication Data

US 2021/0204973 A1    Jul. 8, 2021

Related U.S. Application Data

(63) Continuation of application No. 15/697,494, filed on Sep. 7, 2017, now Pat. No. 11,000,312, which is a
(Continued)

(51) Int. Cl.
*A61B 17/34* (2006.01)
*A61B 1/00* (2006.01)
(Continued)

(52) U.S. Cl.
CPC ...... *A61B 17/3421* (2013.01); *A61B 1/00045* (2013.01); *A61B 1/00089* (2013.01);
(Continued)

(58) Field of Classification Search
CPC .... A61B 2017/3443; A61B 2017/3447; A61B 2017/347; A61B 2017/348;
(Continued)

(56) References Cited

U.S. PATENT DOCUMENTS 4,132,227 A    1/1979 Ibe
4,318,401 A    3/1982 Zimmerman
(Continued)

FOREIGN PATENT DOCUMENTS

CN    2659368 Y    12/2004
CN    1735380 A    2/2006
(Continued)

OTHER PUBLICATIONS

U.S. Appl. No. 15/254,877, filed Sep. 1, 2016, Multi-Shield Spinal Access System.
(Continued)

*Primary Examiner* — Marcela I. Shirsat
(74) *Attorney, Agent, or Firm* — Barnes & Thornburg LLP

(57) ABSTRACT

An access device for accessing an intervertebral disc having an outer shield comprising an access shield with a larger diameter (~16-30 mm) that reaches from the skin down to the facet line, with an inner shield having a second smaller diameter (~5-12 mm) extending past the access shield and reaches down to the disc level. This combines the benefits of the direct visual microsurgical/mini open approaches and the percutaneous, "ultra-MIS" techniques.

13 Claims, 72 Drawing Sheets

Related U.S. Application Data continuation-in-part of application No. 15/437,792, filed on Feb. 21, 2017, now Pat. No. 10,874,425, which is a continuation-in-part of application No. 15/254,877, filed on Sep. 1, 2016, now Pat. No. 10,987,129.

(60) Provisional application No. 62/214,297, filed on Sep. 4, 2015.

(51) Int. Cl.

| | | |
|---|---|---|
| *A61B 1/018* | (2006.01) | |
| *A61B 1/05* | (2006.01) | |
| *A61B 1/07* | (2006.01) | |
| *A61B 1/32* | (2006.01) | |
| *A61B 5/06* | (2006.01) | |
| *A61B 5/00* | (2006.01) | |
| *A61B 17/00* | (2006.01) | |
| *A61B 17/02* | (2006.01) | |
| *A61B 90/00* | (2016.01) | |
| *A61B 90/50* | (2016.01) | |
| *A61B 90/57* | (2016.01) | |
| *A61B 1/012* | (2006.01) | |
| *A61B 1/055* | (2006.01) | |
| *A61B 1/12* | (2006.01) | |
| *A61B 1/233* | (2006.01) | |
| *A61B 1/267* | (2006.01) | |
| *A61B 1/313* | (2006.01) | |
| *A61B 1/317* | (2006.01) | |
| *A61B 17/32* | (2006.01) | |
| *A61B 17/60* | (2006.01) | |
| *A61B 17/70* | (2006.01) | |
| *A61B 18/18* | (2006.01) | |
| *A61F 2/44* | (2006.01) | |
| *A61F 2/46* | (2006.01) | |
| *A61B 5/24* | (2021.01) | |
| *A61B 34/20* | (2016.01) | |
| *A61B 34/00* | (2016.01) | |
| *A61B 90/30* | (2016.01) | |
| *A61B 17/16* | (2006.01) | |
| *A61B 17/17* | (2006.01) | |
| *A61B 17/56* | (2006.01) | |
| *A61B 18/00* | (2006.01) | |
| *A61B 34/30* | (2016.01) | |

(52) U.S. Cl.
CPC ...... *A61B 1/00091* (2013.01); *A61B 1/00094* (2013.01); *A61B 1/00096* (2013.01); *A61B 1/00103* (2013.01); *A61B 1/00128* (2013.01); *A61B 1/00133* (2013.01); *A61B 1/00135* (2013.01); *A61B 1/00154* (2013.01); *A61B 1/012* (2013.01); *A61B 1/018* (2013.01); *A61B 1/05* (2013.01); *A61B 1/051* (2013.01); *A61B 1/055* (2013.01); *A61B 1/07* (2013.01); *A61B 1/126* (2013.01); *A61B 1/233* (2013.01); *A61B 1/2676* (2013.01); *A61B 1/317* (2013.01); *A61B 1/3132* (2013.01); *A61B 1/3135* (2013.01); *A61B 1/32* (2013.01); *A61B 5/068* (2013.01); *A61B 5/24* (2021.01); *A61B 5/407* (2013.01); *A61B 5/4041* (2013.01); *A61B 17/00234* (2013.01); *A61B 17/025* (2013.01); *A61B 17/0218* (2013.01); *A61B 17/0293* (2013.01); *A61B 17/320068* (2013.01); *A61B 17/3423* (2013.01); *A61B 17/3462* (2013.01); *A61B 17/60* (2013.01); *A61B 17/708* (2013.01); *A61B 17/7032* (2013.01); *A61B 17/7074* (2013.01); *A61B 18/1815* (2013.01); *A61B 90/03* (2016.02); *A61B 90/361* (2016.02); *A61B 90/50* (2016.02); *A61B 90/57* (2016.02); *A61F 2/4455* (2013.01); *A61F 2/4611* (2013.01); *A61B 1/00149* (2013.01); *A61B 17/0206* (2013.01); *A61B 17/1637* (2013.01); *A61B 17/1671* (2013.01); *A61B 17/1703* (2013.01); *A61B 17/1757* (2013.01); *A61B 17/3403* (2013.01); *A61B 17/3439* (2013.01); *A61B 17/70* (2013.01); *A61B 17/7083* (2013.01); *A61B 34/30* (2016.02); *A61B 34/70* (2016.02); *A61B 90/30* (2016.02); *A61B 2017/0034* (2013.01); *A61B 2017/00261* (2013.01); *A61B 2017/00314* (2013.01); *A61B 2017/00345* (2013.01); *A61B 2017/00407* (2013.01); *A61B 2017/00477* (2013.01); *A61B 2017/00557* (2013.01); *A61B 2017/00738* (2013.01); *A61B 2017/00831* (2013.01); *A61B 2017/00858* (2013.01); *A61B 2017/00871* (2013.01); *A61B 2017/00946* (2013.01); *A61B 2017/00991* (2013.01); *A61B 2017/0256* (2013.01); *A61B 2017/0262* (2013.01); *A61B 2017/320075* (2017.08); *A61B 2017/345* (2013.01); *A61B 2017/347* (2013.01); *A61B 2017/3443* (2013.01); *A61B 2017/3445* (2013.01); *A61B 2017/3447* (2013.01); *A61B 2017/3454* (2013.01); *A61B 2017/3484* (2013.01); *A61B 2017/564* (2013.01); *A61B 2018/00339* (2013.01); *A61B 2018/00565* (2013.01); *A61B 2018/00577* (2013.01); *A61B 2018/1861* (2013.01); *A61B 2018/1869* (2013.01); *A61B 2034/2055* (2016.02); *A61B 2090/034* (2016.02); *A61B 2090/036* (2016.02); *A61B 2090/08021* (2016.02); *A61B 2090/306* (2016.02); *A61B 2090/371* (2016.02); *A61B 2090/3983* (2016.02); *A61B 2218/002* (2013.01); *A61B 2218/007* (2013.01); *A61F 2002/4635* (2013.01)

(58) Field of Classification Search
CPC . A61B 17/1757; A61B 17/02; A61B 17/3403; A61B 17/1703; A61B 17/3421; A61B 17/3423; A61B 17/3462; A61B 2034/2055; A61B 2034/2068; A61B 34/20; A61B 17/564
USPC .......................................................... 606/96
See application file for complete search history.

(56) References Cited

U.S. PATENT DOCUMENTS

| | | |
|---|---|---|
| 4,573,448 A | 3/1986 | Kambin |
| 4,646,738 A | 3/1987 | Trott |
| 4,678,459 A | 7/1987 | Onik et al. |
| 4,807,593 A | 2/1989 | Ito |
| 4,863,430 A | 9/1989 | Klyce et al. |
| 4,874,375 A | 10/1989 | Ellison |
| 4,888,146 A | 12/1989 | Dandeneau |
| 5,080,662 A | 1/1992 | Paul |
| 5,195,541 A | 3/1993 | Obenchain |
| 5,207,213 A | 5/1993 | Auhll et al. |
| 5,285,795 A | 2/1994 | Ryan et al. |
| 5,395,317 A | 3/1995 | Kambin |
| 5,439,464 A | 8/1995 | Shapiro |
| 5,529,580 A | 6/1996 | Kusunoki et al. |
| 5,540,706 A | 7/1996 | Aust et al. |
| 5,569,290 A | 10/1996 | McAfee |
| 5,591,187 A | 1/1997 | Dekel |
| 5,601,569 A | 2/1997 | Pisharodi |

(56) References Cited

U.S. PATENT DOCUMENTS

| | | | |
|---|---|---|---|
| 5,615,690 | A | 4/1997 | Giurtino et al. |
| 5,618,293 | A | 4/1997 | Sample et al. |
| 5,662,300 | A | 9/1997 | Michelson |
| 5,688,222 | A | 11/1997 | Hluchy et al. |
| 5,697,888 | A | 12/1997 | Kobayashi et al. |
| 5,730,754 | A | 3/1998 | Obenchain |
| 5,733,242 | A | 3/1998 | Rayburn et al. |
| 5,735,792 | A | 4/1998 | Vanden Hoek et al. |
| 5,749,602 | A | 5/1998 | Delaney et al. |
| 5,792,044 | A * | 8/1998 | Foley ............... A61B 17/3417 600/102 |
| 5,820,623 | A | 10/1998 | Ng |
| 5,885,300 | A | 3/1999 | Tokuhashi et al. |
| 5,894,369 | A | 4/1999 | Akiba et al. |
| 5,899,425 | A | 5/1999 | Corey, Jr. et al. |
| 5,928,137 | A | 7/1999 | Green |
| 5,954,635 | A | 9/1999 | Foley et al. |
| 5,976,075 | A | 11/1999 | Beane et al. |
| 5,989,183 | A | 11/1999 | Reisdorf et al. |
| 6,017,333 | A | 1/2000 | Bailey |
| 6,033,105 | A | 3/2000 | Barker et al. |
| 6,053,907 | A | 4/2000 | Zirps |
| 6,063,021 | A | 5/2000 | Hossain et al. |
| 6,110,182 | A | 8/2000 | Mowlai-Ashtiani |
| 6,126,592 | A | 10/2000 | Proch et al. |
| 6,139,563 | A | 10/2000 | Cosgrove et al. |
| 6,200,322 | B1 | 3/2001 | Branch et al. |
| 6,217,509 | B1 | 4/2001 | Foley et al. |
| 6,234,961 | B1 | 5/2001 | Gray |
| 6,283,966 | B1 | 9/2001 | Houfburg |
| 6,286,179 | B1 | 9/2001 | Byrne |
| 6,296,644 | B1 | 10/2001 | Saurat et al. |
| 6,322,498 | B1 | 11/2001 | Gravenstein et al. |
| 6,354,992 | B1 | 3/2002 | Kato |
| 6,357,710 | B1 | 3/2002 | Fielden et al. |
| 6,371,968 | B1 | 4/2002 | Kogasaka et al. |
| 6,383,191 | B1 | 5/2002 | Zdeblick et al. |
| 6,447,446 | B1 | 9/2002 | Smith et al. |
| 6,468,289 | B1 | 10/2002 | Bonutti |
| 6,520,495 | B1 | 2/2003 | La Mendola |
| 6,558,407 | B1 | 5/2003 | Ivanko et al. |
| 6,575,899 | B1 | 6/2003 | Foley et al. |
| 6,579,281 | B2 | 6/2003 | Palmer et al. |
| 6,596,008 | B1 | 7/2003 | Kambin |
| 6,626,830 | B1 | 9/2003 | Califiore et al. |
| 6,648,915 | B2 | 11/2003 | Sazy |
| 6,663,563 | B1 | 12/2003 | Sharratt |
| 6,676,597 | B2 | 1/2004 | Guenst et al. |
| 6,679,833 | B2 | 1/2004 | Smith et al. |
| 6,685,724 | B1 | 2/2004 | Haluck |
| 6,688,564 | B2 | 2/2004 | Salvermoser et al. |
| 6,758,809 | B2 | 7/2004 | Briscoe et al. |
| 6,808,505 | B2 | 10/2004 | Kadan |
| 6,887,198 | B2 | 5/2005 | Phillips et al. |
| 6,983,930 | B1 | 1/2006 | La Mendola et al. |
| 7,001,342 | B2 * | 2/2006 | Faciszewski ...... A61B 10/0266 600/564 |
| 7,087,058 | B2 | 8/2006 | Cragg |
| 7,104,986 | B2 | 9/2006 | Hovda et al. |
| 7,137,949 | B2 | 11/2006 | Scirica et al. |
| 7,179,261 | B2 | 2/2007 | Sicvol et al. |
| 7,182,731 | B2 | 2/2007 | Nguyen et al. |
| 7,226,413 | B2 | 6/2007 | McKinley |
| 7,341,556 | B2 | 3/2008 | Shalman |
| 7,434,325 | B2 | 10/2008 | Foley et al. |
| 7,491,168 | B2 | 2/2009 | Raymond et al. |
| 7,591,790 | B2 | 9/2009 | Pflueger |
| 7,594,888 | B2 | 9/2009 | Raymond et al. |
| 7,618,431 | B2 | 11/2009 | Roehm, III et al. |
| 7,636,596 | B2 | 12/2009 | Solar |
| 7,637,905 | B2 | 12/2009 | Saadat et al. |
| 7,641,659 | B2 | 1/2010 | Emstad et al. |
| 7,766,313 | B2 | 8/2010 | Panosian |
| 7,771,384 | B2 | 8/2010 | Ravo |
| 7,794,456 | B2 | 9/2010 | Sharps et al. |
| 7,794,469 | B2 | 9/2010 | Kao et al. |
| 7,811,303 | B2 | 10/2010 | Fallin et al. |
| 7,931,579 | B2 | 4/2011 | Bertolero et al. |
| 7,946,981 | B1 | 5/2011 | Cubb |
| 7,951,141 | B2 | 5/2011 | Sharps et al. |
| 7,959,564 | B2 | 6/2011 | Ritland |
| 7,988,623 | B2 | 8/2011 | Pagliuca et al. |
| 8,007,492 | B2 | 8/2011 | DiPoto et al. |
| 8,038,606 | B2 | 10/2011 | Otawara |
| 8,043,381 | B2 | 10/2011 | Hestad et al. |
| 8,062,218 | B2 | 11/2011 | Sebastian et al. |
| 8,079,952 | B2 | 12/2011 | Fujimoto |
| 8,092,464 | B2 | 1/2012 | McKay |
| 8,096,944 | B2 | 1/2012 | Harrel |
| 8,202,216 | B2 | 6/2012 | Melkent et al. |
| 8,206,357 | B2 | 6/2012 | Bettuchi |
| 8,230,863 | B2 | 7/2012 | Ravikumar et al. |
| 8,236,006 | B2 * | 8/2012 | Hamada ............. A61B 17/7001 606/104 |
| 8,267,896 | B2 | 9/2012 | Hartoumbekis et al. |
| 8,303,492 | B2 | 11/2012 | Ito |
| 8,333,690 | B2 | 12/2012 | Ikeda |
| 8,360,970 | B2 | 1/2013 | Mangiardi |
| 8,372,131 | B2 | 2/2013 | Hestad et al. |
| 8,382,048 | B2 | 2/2013 | Nesper et al. |
| 8,397,335 | B2 | 3/2013 | Gordin et al. |
| 8,419,625 | B2 | 4/2013 | Ito |
| 8,435,174 | B2 | 5/2013 | Cropper et al. |
| 8,460,180 | B1 | 6/2013 | Zarate et al. |
| 8,460,186 | B2 | 6/2013 | Ortiz et al. |
| 8,460,310 | B2 | 6/2013 | Stern |
| 8,518,087 | B2 | 8/2013 | Lopez et al. |
| 8,535,220 | B2 | 9/2013 | Mondschein |
| 8,556,809 | B2 | 10/2013 | Vijayanagar |
| 8,585,726 | B2 | 11/2013 | Yoon et al. |
| 8,602,979 | B2 | 12/2013 | Kitano |
| 8,622,894 | B2 | 1/2014 | Banik et al. |
| 8,636,655 | B1 | 1/2014 | Childs |
| 8,648,932 | B2 | 2/2014 | Talbert et al. |
| 8,688,186 | B1 | 4/2014 | Mao et al. |
| 8,690,764 | B2 | 4/2014 | Clark et al. |
| 8,721,536 | B2 | 5/2014 | Marino et al. |
| 8,740,779 | B2 | 6/2014 | Yoshida |
| 8,784,421 | B2 | 7/2014 | Garrison et al. |
| 8,821,378 | B2 | 9/2014 | Morgenstern Lopez et al. |
| 8,834,507 | B2 | 9/2014 | Mire et al. |
| 8,845,734 | B2 | 9/2014 | Weiman |
| 8,852,242 | B2 | 10/2014 | Morgenstern Lopez et al. |
| 8,870,753 | B2 | 10/2014 | Boulais et al. |
| 8,870,756 | B2 | 10/2014 | Maurice |
| 8,876,712 | B2 | 11/2014 | Yee et al. |
| 8,888,689 | B2 | 11/2014 | Poll et al. |
| 8,888,813 | B2 | 11/2014 | To |
| 8,894,573 | B2 | 11/2014 | Loftus et al. |
| 8,894,653 | B2 | 11/2014 | Solsberg et al. |
| 8,926,502 | B2 | 1/2015 | Levy et al. |
| 8,932,207 | B2 | 1/2015 | Greenburg et al. |
| 8,932,360 | B2 | 1/2015 | Womble et al. |
| 8,936,545 | B2 | 1/2015 | To |
| 8,936,605 | B2 | 1/2015 | Greenberg |
| 8,952,312 | B2 | 2/2015 | Blanquart et al. |
| 8,961,404 | B2 | 2/2015 | Ito |
| 8,972,714 | B2 | 3/2015 | Talbert et al. |
| 8,974,381 | B1 | 3/2015 | Lovell et al. |
| 8,986,199 | B2 | 3/2015 | Weisenburgh, II et al. |
| 8,992,580 | B2 | 3/2015 | Bar et al. |
| 9,028,522 | B1 | 5/2015 | Prado |
| 9,050,036 | B2 | 6/2015 | Poll et al. |
| 9,050,037 | B2 | 6/2015 | Poll et al. |
| 9,050,146 | B2 | 6/2015 | Woolley et al. |
| 9,055,936 | B2 | 6/2015 | Mire et al. |
| 9,072,431 | B2 | 7/2015 | Adams et al. |
| 9,078,562 | B2 | 7/2015 | Poll et al. |
| 9,123,602 | B2 | 9/2015 | Blanquart |
| 9,131,948 | B2 | 9/2015 | Fang et al. |
| 9,144,374 | B2 | 9/2015 | Maurice, Jr. |
| 9,153,609 | B2 | 10/2015 | Blanquart |
| 9,198,674 | B2 | 12/2015 | Benson et al. |
| 9,211,059 | B2 | 12/2015 | Drach et al. |

(56) References Cited

U.S. PATENT DOCUMENTS

| | | |
|---|---|---|
| 9,216,016 B2 | 12/2015 | Fiechter et al. |
| 9,216,125 B2 | 12/2015 | Sklar |
| 9,226,647 B2 | 1/2016 | Sugawara |
| 9,232,935 B2 | 1/2016 | Brand et al. |
| 9,247,997 B2 | 2/2016 | Stefanchik et al. |
| 9,265,491 B2 | 2/2016 | Lins et al. |
| 9,277,928 B2 | 3/2016 | Morgenstern Lopez |
| 9,307,972 B2 | 4/2016 | Lovell et al. |
| 9,320,419 B2 | 4/2016 | Kirma et al. |
| RE46,007 E | 5/2016 | Banik et al. |
| RE46,062 E | 7/2016 | James et al. |
| 9,386,971 B1 | 7/2016 | Casey et al. |
| 9,387,313 B2 | 7/2016 | Culbert et al. |
| 9,414,828 B2 | 8/2016 | Abidin et al. |
| 9,462,234 B2 | 10/2016 | Blanquart et al. |
| 9,486,296 B2 | 11/2016 | Mire et al. |
| 9,492,194 B2 | 11/2016 | Morgenstern Lopez et al. |
| 9,509,917 B2 | 11/2016 | Blanquart et al. |
| 9,510,853 B2 | 12/2016 | Aljuri et al. |
| 9,516,239 B2 | 12/2016 | Blanquart et al. |
| 9,522,017 B2 | 12/2016 | Poll et al. |
| 9,526,401 B2 | 12/2016 | Saadat et al. |
| 9,579,012 B2 | 2/2017 | Vazales et al. |
| 9,603,510 B2 | 3/2017 | Ammirati |
| 9,603,610 B2 | 3/2017 | Richter et al. |
| 9,610,007 B2 | 4/2017 | Kienzle et al. |
| 9,610,095 B2 | 4/2017 | To |
| 9,622,650 B2 | 4/2017 | Blanquart |
| 9,629,521 B2 | 4/2017 | Ratnakar |
| 9,641,815 B2 | 5/2017 | Richardson et al. |
| 9,655,605 B2 | 5/2017 | Serowski et al. |
| 9,655,639 B2 | 5/2017 | Mark |
| 9,668,643 B2 | 6/2017 | Kennedy, II et al. |
| 9,675,235 B2 | 6/2017 | Lieponis |
| 9,700,378 B2 | 7/2017 | Mowlai-Ashtiani |
| 9,706,905 B2 | 7/2017 | Levy |
| 10,561,427 B2 | 2/2020 | Weitzman et al. |
| 10,576,231 B2 | 3/2020 | Gunday et al. |
| 10,682,130 B2 | 6/2020 | White et al. |
| 10,758,220 B2 | 9/2020 | White et al. |
| 10,869,659 B2 | 12/2020 | Thommen et al. |
| 10,874,425 B2 | 12/2020 | Thommen et al. |
| 10,987,129 B2 | 4/2021 | Thommen et al. |
| 11,000,312 B2 | 5/2021 | Thommen et al. |
| 11,331,090 B2 | 5/2022 | Thommen et al. |
| 11,439,380 B2 | 9/2022 | Thommen et al. |
| 11,559,328 B2 | 1/2023 | Richter et al. |
| 2002/0022762 A1 | 2/2002 | Beane et al. |
| 2002/0035313 A1 | 3/2002 | Scirica et al. |
| 2002/0091390 A1 | 7/2002 | Michelson |
| 2002/0138020 A1 | 9/2002 | Pflueger |
| 2002/0165560 A1 | 11/2002 | Danitz et al. |
| 2003/0083555 A1 | 5/2003 | Hunt et al. |
| 2003/0083688 A1 | 5/2003 | Simonson |
| 2003/0171744 A1 | 9/2003 | Leung et al. |
| 2003/0191474 A1 | 10/2003 | Cragg et al. |
| 2004/0092940 A1 | 5/2004 | Zwirnmann |
| 2004/0122446 A1 | 6/2004 | Solar |
| 2004/0127992 A1 | 7/2004 | Serhan et al. |
| 2004/0143165 A1 | 7/2004 | Alleyne |
| 2004/0158260 A1 | 8/2004 | Blau et al. |
| 2004/0158286 A1 | 8/2004 | Roux et al. |
| 2004/0249246 A1 | 12/2004 | Campos |
| 2005/0021040 A1 | 1/2005 | Bertagnoli |
| 2005/0075540 A1 | 4/2005 | Shluzas et al. |
| 2005/0075644 A1 | 4/2005 | DiPoto et al. |
| 2005/0080435 A1 | 4/2005 | Smith et al. |
| 2005/0085692 A1 | 4/2005 | Kiehn et al. |
| 2005/0090848 A1 | 4/2005 | Adams |
| 2005/0107671 A1 | 5/2005 | McKinley |
| 2005/0137461 A1 | 6/2005 | Marchek et al. |
| 2005/0187570 A1 | 8/2005 | Nguyen et al. |
| 2005/0192589 A1 | 9/2005 | Raymond et al. |
| 2005/0256525 A1 | 11/2005 | Culbert et al. |
| 2006/0020165 A1 | 1/2006 | Adams |
| 2006/0041270 A1 | 2/2006 | Lenker et al. |
| 2006/0052671 A1 | 3/2006 | McCarthy |
| 2006/0074445 A1 | 4/2006 | Gerber et al. |
| 2006/0142643 A1 | 6/2006 | Parker |
| 2006/0161189 A1 | 7/2006 | Harp |
| 2006/0173521 A1 | 8/2006 | Pond et al. |
| 2006/0200186 A1 | 9/2006 | Marchek et al. |
| 2006/0206118 A1 | 9/2006 | Kim et al. |
| 2006/0264895 A1 | 11/2006 | Flanders |
| 2007/0049794 A1 | 3/2007 | Glassenberg et al. |
| 2007/0055259 A1 | 3/2007 | Norton et al. |
| 2007/0129634 A1 | 6/2007 | Hickey et al. |
| 2007/0149975 A1 | 6/2007 | Oliver et al. |
| 2007/0162223 A1 | 7/2007 | Clark |
| 2007/0203396 A1 | 8/2007 | McCutcheon et al. |
| 2007/0213716 A1 | 9/2007 | Lenke et al. |
| 2007/0225556 A1 | 9/2007 | Ortiz et al. |
| 2007/0249899 A1 | 10/2007 | Seifert |
| 2007/0255100 A1 | 11/2007 | Barlow et al. |
| 2007/0260113 A1 | 11/2007 | Otawara |
| 2007/0260120 A1 | 11/2007 | Otawara |
| 2007/0260184 A1 | 11/2007 | Justis et al. |
| 2007/0270866 A1 | 11/2007 | von Jako |
| 2008/0015621 A1 | 1/2008 | Emanuel |
| 2008/0033251 A1 | 2/2008 | Araghi |
| 2008/0064921 A1 | 3/2008 | Larkin et al. |
| 2008/0064928 A1 | 3/2008 | Otawara |
| 2008/0081951 A1 | 4/2008 | Frasier et al. |
| 2008/0139879 A1 | 6/2008 | Olson et al. |
| 2008/0147109 A1 | 6/2008 | Kambin et al. |
| 2008/0183189 A1* | 7/2008 | Teichman ............... A61B 6/506 606/130 |
| 2008/0188714 A1 | 8/2008 | McCaffrey |
| 2008/0242930 A1 | 10/2008 | Hanypsiak et al. |
| 2008/0260342 A1 | 10/2008 | Kuroiwa |
| 2009/0018566 A1 | 1/2009 | Escudero et al. |
| 2009/0024158 A1 | 1/2009 | Viker |
| 2009/0062871 A1 | 3/2009 | Chin et al. |
| 2009/0105543 A1 | 4/2009 | Miller et al. |
| 2009/0125032 A1 | 5/2009 | Gutierrez et al. |
| 2009/0149857 A1* | 6/2009 | Culbert ............... A61B 1/00071 606/191 |
| 2009/0156898 A1 | 6/2009 | Ichimura |
| 2009/0187080 A1 | 7/2009 | Seex |
| 2009/0240111 A1 | 9/2009 | Kessler et al. |
| 2009/0253964 A1 | 10/2009 | Miyamoto |
| 2009/0253965 A1 | 10/2009 | Miyamoto |
| 2009/0259184 A1 | 10/2009 | Okoniewski |
| 2009/0264895 A1 | 10/2009 | Gasperut et al. |
| 2009/0287061 A1 | 11/2009 | Feigenbaum et al. |
| 2009/0318765 A1 | 12/2009 | Torii |
| 2010/0004651 A1 | 1/2010 | Biyani |
| 2010/0022841 A1 | 1/2010 | Takahashi et al. |
| 2010/0076476 A1 | 3/2010 | To et al. |
| 2010/0081875 A1 | 4/2010 | Fowler et al. |
| 2010/0114147 A1 | 5/2010 | Biyani |
| 2010/0151161 A1 | 6/2010 | Da Rolo |
| 2010/0161060 A1 | 6/2010 | Schaller et al. |
| 2010/0256446 A1 | 10/2010 | Raju |
| 2010/0268241 A1 | 10/2010 | Flom et al. |
| 2010/0280325 A1 | 11/2010 | Ibrahim et al. |
| 2010/0284580 A1 | 11/2010 | OuYang et al. |
| 2010/0286477 A1 | 11/2010 | OuYang et al. |
| 2010/0312053 A1 | 12/2010 | Larsen |
| 2010/0317928 A1 | 12/2010 | Subramaniam |
| 2010/0324506 A1 | 12/2010 | Pellegrino et al. |
| 2011/0009905 A1 | 1/2011 | Shluzas |
| 2011/0028791 A1 | 2/2011 | Marino et al. |
| 2011/0040333 A1 | 2/2011 | Simonson et al. |
| 2011/0054507 A1 | 3/2011 | Batten et al. |
| 2011/0056500 A1 | 3/2011 | Shin et al. |
| 2011/0073594 A1* | 3/2011 | Bonn .................... H05B 6/80 219/759 |
| 2011/0098628 A1 | 4/2011 | Yeung et al. |
| 2011/0106261 A1 | 5/2011 | Chin et al. |
| 2011/0112588 A1 | 5/2011 | Linderman et al. |
| 2011/0125158 A1 | 5/2011 | Diwan et al. |
| 2011/0130634 A1 | 6/2011 | Solitario, Jr. et al. |
| 2011/0201888 A1 | 8/2011 | Verner |

(56) References Cited

U.S. PATENT DOCUMENTS

| | | |
|---|---|---|
| 2011/0230965 A1 | 9/2011 | Schell et al. |
| 2011/0251597 A1 | 10/2011 | Bharadwaj et al. |
| 2011/0257478 A1 | 10/2011 | Kleiner et al. |
| 2011/0295070 A1 | 12/2011 | Yasunaga |
| 2011/0319941 A1 | 12/2011 | Bar et al. |
| 2012/0016192 A1 | 1/2012 | Jansen et al. |
| 2012/0029412 A1 | 2/2012 | Yeung et al. |
| 2012/0095296 A1 | 4/2012 | Trieu et al. |
| 2012/0101338 A1 | 4/2012 | O'Prey et al. |
| 2012/0111682 A1 | 5/2012 | Andre |
| 2012/0116170 A1 | 5/2012 | Vayser et al. |
| 2012/0157788 A1 | 6/2012 | Serowski et al. |
| 2012/0172664 A1 | 7/2012 | Hayman et al. |
| 2012/0209273 A1 | 8/2012 | Zaretzka et al. |
| 2012/0221007 A1 | 8/2012 | Batten et al. |
| 2012/0232350 A1 | 9/2012 | Seex |
| 2012/0232552 A1 | 9/2012 | Morgenstern Lopez et al. |
| 2012/0259173 A1 | 10/2012 | Waldron et al. |
| 2012/0265022 A1 | 10/2012 | Menn |
| 2012/0296171 A1 | 11/2012 | Lovell et al. |
| 2012/0298820 A1 | 11/2012 | Manolidis |
| 2012/0316400 A1 | 12/2012 | Vijayanagar |
| 2012/0323080 A1 | 12/2012 | DeRidder et al. |
| 2013/0030535 A1 | 1/2013 | Foley et al. |
| 2013/0103067 A1 | 4/2013 | Fabro et al. |
| 2013/0103103 A1 | 4/2013 | Mire et al. |
| 2013/0150670 A1 | 6/2013 | O'Prey et al. |
| 2013/0150674 A1 | 6/2013 | Haig et al. |
| 2013/0172674 A1 | 7/2013 | Kennedy, II et al. |
| 2013/0172676 A1 | 7/2013 | Levy et al. |
| 2013/0211202 A1 | 8/2013 | Perez-Cruet et al. |
| 2013/0282022 A1 | 10/2013 | Yousef |
| 2013/0289399 A1 | 10/2013 | Choi et al. |
| 2013/0303846 A1 | 11/2013 | Cybulski et al. |
| 2013/0304106 A1 | 11/2013 | Breznock |
| 2014/0025121 A1 | 1/2014 | Foley et al. |
| 2014/0066940 A1 | 3/2014 | Fang et al. |
| 2014/0074170 A1 | 3/2014 | Mertens et al. |
| 2014/0088367 A1 | 3/2014 | DiMauro et al. |
| 2014/0128979 A1 | 5/2014 | Womble et al. |
| 2014/0142584 A1 | 5/2014 | Sweeney |
| 2014/0148647 A1 | 5/2014 | Okazaki |
| 2014/0163319 A1 | 6/2014 | Blanquart et al. |
| 2014/0180321 A1 | 6/2014 | Dias et al. |
| 2014/0194697 A1 | 7/2014 | Seex |
| 2014/0215736 A1 | 8/2014 | Gomez et al. |
| 2014/0221749 A1 | 8/2014 | Grant et al. |
| 2014/0222092 A1 | 8/2014 | Anderson et al. |
| 2014/0257296 A1 | 9/2014 | Morgenstern Lopez |
| 2014/0257332 A1 | 9/2014 | Zastrozna |
| 2014/0257489 A1 | 9/2014 | Warren et al. |
| 2014/0261545 A1 | 9/2014 | Jenkins et al. |
| 2014/0275793 A1 | 9/2014 | Song |
| 2014/0275799 A1 | 9/2014 | Schuele |
| 2014/0276840 A1 | 9/2014 | Richter et al. |
| 2014/0276916 A1 | 9/2014 | Ahluwalia et al. |
| 2014/0277204 A1 | 9/2014 | Sandhu |
| 2014/0285644 A1 | 9/2014 | Richardson et al. |
| 2014/0318582 A1 | 10/2014 | Mowlai-Ashtiani |
| 2014/0336764 A1 | 11/2014 | Masson et al. |
| 2014/0357945 A1 | 12/2014 | Duckworth |
| 2014/0371763 A1 | 12/2014 | Poll et al. |
| 2014/0378985 A1 | 12/2014 | Mafi |
| 2015/0018623 A1 | 1/2015 | Friedrich et al. |
| 2015/0065795 A1 | 3/2015 | Titus |
| 2015/0073218 A1 | 3/2015 | Ito |
| 2015/0087913 A1 | 3/2015 | Dang et al. |
| 2015/0112398 A1 | 4/2015 | Morgenstern Lopez et al. |
| 2015/0133727 A1 | 5/2015 | Bacich et al. |
| 2015/0164496 A1 | 6/2015 | Karpowicz et al. |
| 2015/0216593 A1 | 8/2015 | Biyani |
| 2015/0223671 A1 | 8/2015 | Sung et al. |
| 2015/0223676 A1 | 8/2015 | Bayer et al. |
| 2015/0230697 A1 | 8/2015 | Phee et al. |
| 2015/0238073 A1 | 8/2015 | Charles et al. |
| 2015/0250377 A1 | 9/2015 | Iizuka |
| 2015/0257746 A1 | 9/2015 | Seifert |
| 2015/0272694 A1 | 10/2015 | Charles |
| 2015/0313585 A1 | 11/2015 | Abidin et al. |
| 2015/0313633 A1 | 11/2015 | Gross et al. |
| 2015/0327757 A1 | 11/2015 | Rozenfeld et al. |
| 2015/0335389 A1 | 11/2015 | Greenberg |
| 2015/0342619 A1 | 12/2015 | Weitzman |
| 2015/0342621 A1 | 12/2015 | Jackson, III |
| 2015/0366552 A1 | 12/2015 | Sasaki et al. |
| 2015/0374213 A1 | 12/2015 | Maurice, Jr. |
| 2015/0374354 A1 | 12/2015 | Boyd et al. |
| 2016/0015467 A1 | 1/2016 | Vayser et al. |
| 2016/0030061 A1 | 2/2016 | Thommen et al. |
| 2016/0066965 A1 | 3/2016 | Chegini et al. |
| 2016/0067003 A1 | 3/2016 | Chegini et al. |
| 2016/0074029 A1 | 3/2016 | O'Connell et al. |
| 2016/0095505 A1 | 4/2016 | Johnson et al. |
| 2016/0106408 A1 | 4/2016 | Ponmudi et al. |
| 2016/0166135 A1 | 6/2016 | Fiset |
| 2016/0174814 A1 | 6/2016 | Igov |
| 2016/0192921 A1 | 7/2016 | Pimenta et al. |
| 2016/0213500 A1 | 7/2016 | Beger et al. |
| 2016/0228280 A1 | 8/2016 | Schuele et al. |
| 2016/0235284 A1 | 8/2016 | Yoshida et al. |
| 2016/0256036 A1 | 9/2016 | Gomez et al. |
| 2016/0287264 A1 | 10/2016 | Chegini et al. |
| 2016/0296220 A1 | 10/2016 | Mast et al. |
| 2016/0324541 A1 | 11/2016 | Pellegrino et al. |
| 2016/0345952 A1 | 12/2016 | Kucharzyk et al. |
| 2016/0353978 A1 | 12/2016 | Miller et al. |
| 2016/0367294 A1 | 12/2016 | Boyd et al. |
| 2017/0003493 A1 | 1/2017 | Zhao |
| 2017/0007226 A1 | 1/2017 | Fehling |
| 2017/0007294 A1 | 1/2017 | Iwasaka et al. |
| 2017/0027606 A1 | 2/2017 | Cappelleri et al. |
| 2017/0042408 A1 | 2/2017 | Washbur et al. |
| 2017/0042411 A1 | 2/2017 | Kang et al. |
| 2017/0065269 A1 | 3/2017 | Thommen et al. |
| 2017/0065287 A1 | 3/2017 | Silva et al. |
| 2017/0086939 A1 | 3/2017 | Vayser et al. |
| 2017/0105770 A1 | 4/2017 | Woolley et al. |
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0196549 A1 | 7/2017 | Piskun et al. |
| 2017/0224391 A1 | 8/2017 | Biester et al. |
| 2017/0245930 A1 | 8/2017 | Brannan et al. |
| 2017/0280969 A1 | 10/2017 | Levy et al. |
| 2017/0296038 A1 | 10/2017 | Gordon et al. |
| 2017/0311789 A1 | 11/2017 | Mulcahey et al. |
| 2018/0008138 A1 | 1/2018 | Thommen et al. |
| 2018/0008253 A1 | 1/2018 | Thommen et al. |
| 2018/0014858 A1 | 1/2018 | Biester et al. |
| 2018/0098788 A1 | 4/2018 | White et al. |
| 2018/0098789 A1 | 4/2018 | White et al. |
| 2018/0110503 A1 | 4/2018 | Flock et al. |
| 2018/0110506 A1 | 4/2018 | Thommen et al. |
| 2018/0153592 A1 | 6/2018 | Larson |
| 2018/0214016 A1 | 8/2018 | Thommen et al. |
| 2018/0249992 A1 | 9/2018 | Truckey |
| 2018/0333061 A1 | 11/2018 | Pracyk et al. |
| 2019/0209154 A1 | 7/2019 | Richter et al. |
| 2019/0216454 A1 | 7/2019 | Thommen et al. |
| 2019/0216486 A1 | 7/2019 | Weitzman |
| 2019/0374236 A1 | 12/2019 | Weitzman et al. |
| 2020/0268368 A1 | 8/2020 | White et al. |
| 2020/0360048 A1 | 11/2020 | White et al. |
| 2020/0367737 A1 | 11/2020 | Matsumoto et al. |
| 2021/0052298 A1 | 2/2021 | Thommen et al. |
| 2021/0204973 A1 | 7/2021 | Thommen et al. |
| 2021/0282806 A1 | 9/2021 | Thommen et al. |
| 2022/0192700 A1 | 6/2022 | Thommen et al. |

(56) References Cited

U.S. PATENT DOCUMENTS

| | | |
|---|---|---|
| 2022/0249125 A1 | 8/2022 | Thommen et al. |
| 2022/0265134 A1 | 8/2022 | Thommen et al. |

FOREIGN PATENT DOCUMENTS

| | | |
|---|---|---|
| CN | 1742685 A | 3/2006 |
| CN | 101426437 A | 5/2009 |
| CN | 201290744 Y | 8/2009 |
| CN | 101815476 A | 8/2010 |
| CN | 102448380 A | 5/2012 |
| CN | 202211669 U | 5/2012 |
| CN | 102497828 A | 6/2012 |
| CN | 102821673 A | 12/2012 |
| CN | 102843984 A | 12/2012 |
| CN | 202740102 U | 2/2013 |
| CN | 102727309 B | 11/2014 |
| CN | 105286776 A | 2/2016 |
| CN | 103976779 B | 9/2016 |
| CN | 106794032 A | 5/2017 |
| CN | 107126254 A | 9/2017 |
| DE | 9415039 U1 | 11/1994 |
| DE | 29916026 U1 | 11/1999 |
| DE | 20309079 U1 | 8/2003 |
| EP | 0 537 116 A1 | 4/1993 |
| EP | 0 807 415 A2 | 11/1997 |
| EP | 0 891 156 A1 | 1/1999 |
| EP | 0890341 A1 | 1/1999 |
| EP | 2 491 848 A1 | 8/2012 |
| GB | 2481727 A | 1/2012 |
| JP | 05-207962 A | 8/1993 |
| JP | 08-278456 A | 10/1996 |
| JP | 2000126190 A | 5/2000 |
| JP | 2000-511788 A | 9/2000 |
| JP | 2001520906 A | 11/2001 |
| JP | 2007-007438 A | 1/2007 |
| JP | 2008-508943 A | 3/2008 |
| JP | 2009543612 A | 12/2009 |
| JP | 2011-512943 A | 4/2011 |
| JP | 2012527327 A | 11/2012 |
| JP | 2012527930 A | 11/2012 |
| JP | 2013059688 A | 4/2013 |
| JP | 2013-538624 A | 10/2013 |
| JP | 2014-517710 A | 7/2014 |
| JP | 2015-500680 A | 1/2015 |
| JP | 2015-521913 A | 8/2015 |
| WO | 96/29014 A1 | 9/1996 |
| WO | 97/34536 A2 | 9/1997 |
| WO | 2001/056490 A1 | 8/2001 |
| WO | 2001/089371 A1 | 11/2001 |
| WO | 2002/002016 A1 | 1/2002 |
| WO | 2004/039235 A2 | 5/2004 |
| WO | 2004/103430 A2 | 12/2004 |
| WO | 2006/017507 A2 | 2/2006 |
| WO | 2007/059068 A1 | 5/2007 |
| WO | 2008/121162 A1 | 10/2008 |
| WO | 2009/033207 A1 | 3/2009 |
| WO | 2009/108318 A2 | 9/2009 |
| WO | 2010/111629 A2 | 9/2010 |
| WO | 2010138083 A1 | 12/2010 |
| WO | 2012/004766 A2 | 1/2012 |
| WO | 2012/040239 A1 | 3/2012 |
| WO | 2012/122294 A1 | 9/2012 |
| WO | 2013/033426 A2 | 3/2013 |
| WO | 2013/059640 A1 | 4/2013 |
| WO | 2013/074396 A1 | 5/2013 |
| WO | 2014/041540 A1 | 3/2014 |
| WO | 2014/050236 A1 | 4/2014 |
| WO | 2014/100761 A2 | 6/2014 |
| WO | 2014/185334 A1 | 11/2014 |
| WO | 2015026793 A1 | 2/2015 |
| WO | 2015/175635 A1 | 11/2015 |
| WO | 2016/111373 A1 | 7/2016 |
| WO | 2016/131077 A1 | 8/2016 |
| WO | 2016/168673 A1 | 10/2016 |
| WO | 2016/201292 A1 | 12/2016 |
| WO | 2017/006684 A1 | 1/2017 |
| WO | 2017/015480 A1 | 1/2017 |
| WO | 2017/040873 A1 | 3/2017 |
| WO | 2017/083648 A1 | 5/2017 |
| WO | 2018/131039 A1 | 7/2018 |
| WO | 2018/165365 A2 | 9/2018 |
| WO | 2021/209987 A1 | 10/2021 |

OTHER PUBLICATIONS

U.S. Appl. No. 15/437,792, filed Feb. 21, 2017, Multi-Shield Spinal Access System.

U.S. Appl. No. 15/692,845, filed Aug. 31 2017, Surgical Visualization Systems and Related Methods.

U.S. Appl. No. 15/697,494, filed Sep. 7, 2017, Multi-Shield Spinal Access System.

U.S. Appl. No. 15/786,846, filed Oct. 18, 2017, Devices and Methods for Surgical Retraction.

U.S. Appl. No. 15/786,858, filed Oct. 18, 2017, Devices and Methods for Providing Surgical Access.

U.S. Appl. No. 15/786,891, filed Oct. 18, 2017, Surgical Access Port Stabilization.

U.S. Appl. No. 15/786,923, filed Oct. 18 2017, Surgical Instrument Connectors and Related Methods.

U.S. Appl. No. 15/901,435, filed Feb. 21 2018, Surgical Visualization Systems and Related Methods.

U.S. Appl. No. 15/931,839, filed May 14, 2020, Surgical Access Port Stabilization.

U.S. Appl. No. 15/966,293, filed Apr. 30 2018, Neural Monitoring Devices and Methods.

U.S. Appl. No. 16/352,654, filed Mar. 13, 2019, Multi-Shield Spinal Access System.

U.S. Appl. No. 16/362,497, filed Mar. 22, 2019, Surgical Instrument Connectors and Related Methods.

U.S. Appl. No. 16/985,200, filed Aug. 4, 2020, Devices and Methods for Providing Surgical Access.

U.S. Appl. No. 17/089,695, filed Nov. 4, 2020, Multi-Shield Spinal Access System.

Hott, J. S., et al., "A new table-fixed retractor for anterior odontoid screw fixation: technical note," J Neurosurg (Spine 3), 2003, v. 98, pp. 118-120.

Extended European Search Report for Application No. 16843037.9; dated Mar. 14, 2019 (8 pages).

Extended European Search Report for Application No. 18758290.3, dated Nov. 27, 2020 (7 pages).

International Search Report and Written Opinion for Application No. PCT/US2015/043554, dated Nov. 19, 2015 (8 pages).

International Search Report and Written Opinion for Application No. PCT/US2015/048485, dated Feb. 9, 2016 (16 pages).

International Search Report and Written Opinion for Application No. PCT/US2015/060978, dated Feb. 15, 2016 (8 pages).

Invitation to Pay Additional Fees for Application No. PCT/US2016/050022, dated Nov. 3, 2016 (2 pages).

International Search Report and Written Opinion for Application No. PCT/US2016/050022, dated Feb. 1, 2017 (19 pages).

International Preliminary Report on Patentability issued for Application No. PCT/US2016/050022, dated Mar. 15, 2018.

International Search Report and Written Opinion for Application No. PCT/US2018/018905, dated May 7, 2018 (10 pages).

International Search Report for Application No. PCT/IB2018/057367, dated Jan. 29, 2019, (4 pages).

International Search Report and Written Opinion for Application No. PCT/EP2020/056706, dated Jun. 9, 2020 (17 pages).

International Search Report and Written Opinion issued for Application No. PCT/US2018/021472, dated Jul. 19, 2018.

International Search Report and Written Opinion for Application No. PCT/US19/18700, dated May 3, 2019 (7 pages).

International Search Report and Written Opinion for Application No. PCT/US2018/021449, dated Aug. 27, 2018 (13 pages).

International Search Report and Written Opinion for Application No. PCT/US2018/021454, dated Jul. 3, 2018 (16 pages).

International Search Report and Written Opinion for Application No. PCT/US2018/021466 dated Jul. 3, 2018 (8 pages).

(56) References Cited

OTHER PUBLICATIONS

International Search Report and Written Opinion for Application No. PCT/US2018/047136, dated Jan. 23, 2019 (9 pages).
Iprenburg, M, "Percutaneous Transforaminal Endoscopic Discectomy: The Thessys Method," in Lewandrowski, K., et al, Minimally Invasive Spinal Fusion Techniques, Summit Communications, 2008 pp. 65-81.
Japanese Office Action issued in Appln. No. JP 2018-511695, dated May 26, 2020 (21 pages).
Jung, K., et al., "A hands-free region-of-interest selection interface for solo surgery with a wide-angle endoscope: preclinical proof of concept," Surg Endosc, 2017, v. 31, pp. 974-980.
Regan, J. M. et al., "Burr Hole Washout versus Craniotomy for Chronic Subdural Hematoma: Patient Outcome and Cost Analysis," Plos One, Jan. 22, 2015, DOI:10.1371/journal.pone.0115085.
Shalayev, S. G. et al., "Retrospective analysis and modifications of retractor systems for anterior odontoid screw fixation," Neurosurg Focus 16 (1):Article 14, 2004, pp. 1-4.
Chinese Office Action for Application No. 201880013056.7, dated Oct. 26, 2021 (6 Pages).
Japanese Office Action for Application No. 2019-545263, dated Jan. 4, 2022 (11 pages).
Extended European Search Report for Application No. 20212396.4, dated Sep. 23, 2021 (9 pages).
Extended European Search Report for Application No. 18854503, dated Apr. 15, 2021 (10 pages).
Extended European Search Report for Application No. 19758283.6, dated Sep. 28, 2021 (8 pages).
Chinese Office Action for Application No. 201880013056.7, dated Mar. 25, 2021 (15 pages).
U.S. Appl. No. 17/192,889, filed Jan. 26, 2021, Surgical Visualization Systems and Related Methods.
Chinese Office Action and Search Report issued for Application No. 201880058099, dated Nov. 2, 2022 (14 pages).
Australian Examination Report for Application No. 2018225113, dated Jul. 15, 2022 (4 pages).
Chinese Office Action for Application No. 201880016688.9, dated Mar. 8, 2022, with Translation (21 pages).
Chinese Decision of Reexamination issued for 201680051245.4, dated Aug. 23, 2022, (23 pages).
"Clinical Workbook of Neurosurgery in Xijing [M], edited by Fei Zhou, Xi'an: Fourth Military Medical University Press, Aug. 2012, pp. 431-432: an endoscope with a diameter of 3.7 mm is used for intramedullary examination)."
Extended European Search Report for Application No. 18764249.1, dated Mar. 11, 2022 (8 pages).
Extended European Search Report for Application No. 18764504.9, dated Mar. 18, 2022 (7 pages).
Extended European Search Report for Application No. 18764370.5, dated Mar. 25, 2022 (8 pages).
Japanese Office Action for Application No. 2019-548591, dated Oct. 5, 2021, (14 pages).
Japanese Office Action for Application No. 2020-513791, dated May 17, 2022 (8 pages).
Japanese Office Action for Application No. 2020-177880, dated May 31, 2022 (3 pages).
Japanese Office Action for Application No. 2019545263, dated Aug. 9, 2022 (8 pages).
U.S. Appl. No. 17/692,942, filed Mar. 11, 2022, Multi-Shield Spinal Access System.

\* cited by examiner

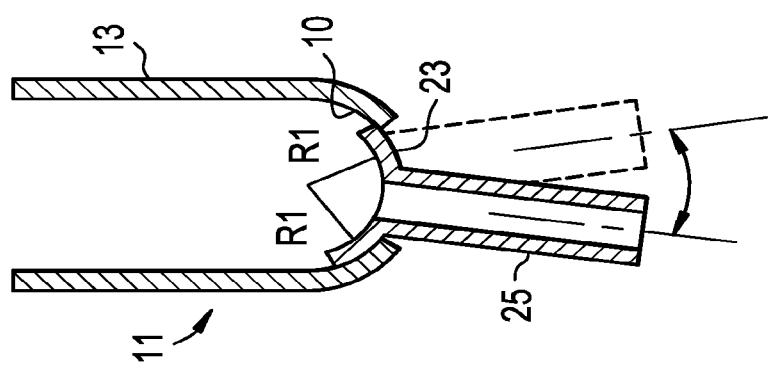
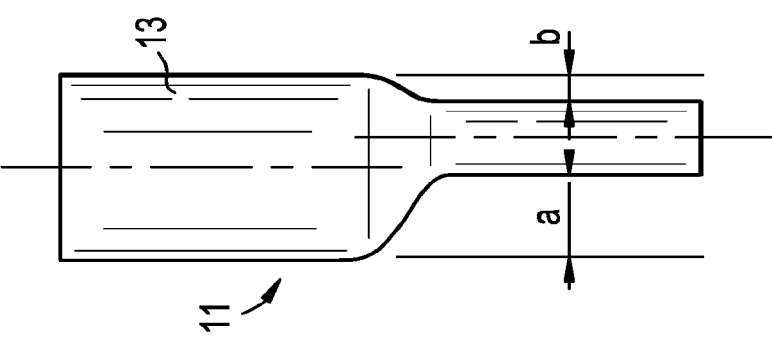
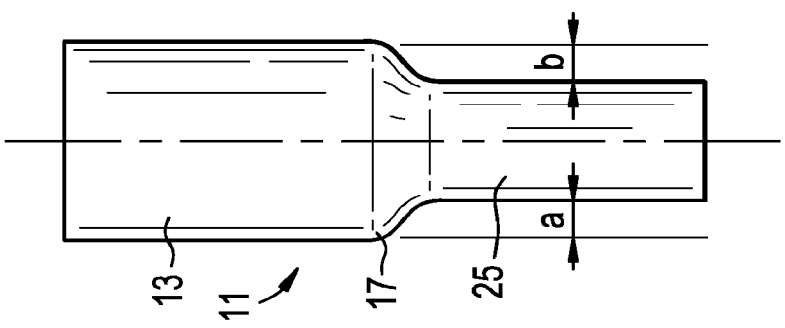
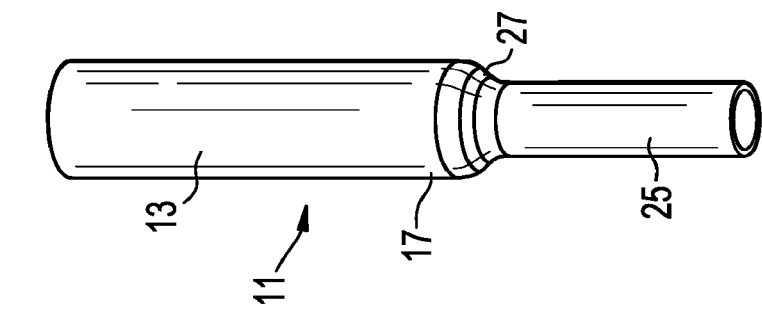

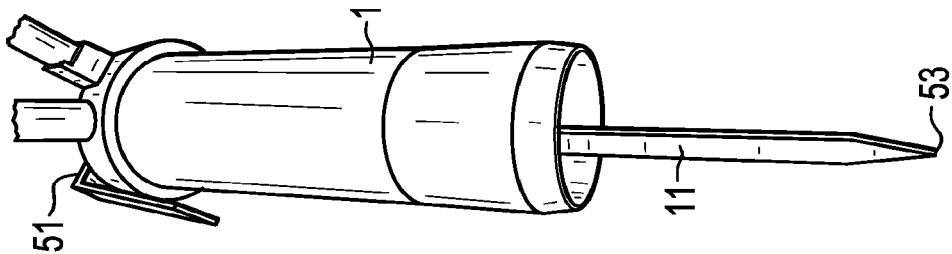
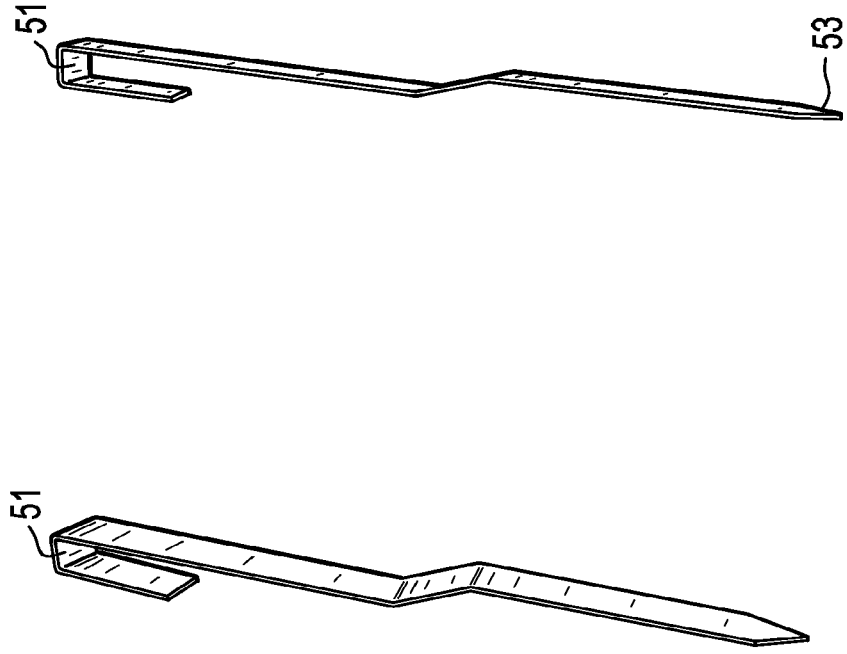

MULTI-SHIELD SPINAL ACCESS SYSTEM

CONTINUING DATA

This application is a continuation of U.S. application Ser. No. 15/697,494, filed on Sep. 7, 2017 (now issued as U.S. Pat. No. 11,000,312). U.S. application Ser. No. 15/697,494 is a continuation-in-part of U.S. application Ser. No. 15/437,792 filed on Feb. 21, 2017 (now issued as U.S. Pat. No. 10,874,425). U.S. application Ser. No. 15/437,792 is a continuation-in-part of U.S. application Ser. No. 15/254,877, filed on Sep. 1, 2016 (now issued as U.S. Pat. No. 10,987,129). U.S. application Ser. No. 15/254,877 claims priority to U.S. Provisional Application No. 62/214,297 filed on Sep. 4, 2015. The entire contents of each of these applications are incorporated herein by reference.

BACKGROUND OF THE INVENTION

Today, microsurgical spinal bone resections and spinal decompressions which are performed under microscopic view through mini-open tubes and retractors are becoming the standard of spinal surgical care. These access tools normally have inner diameters between about 16 mm and 30 mm. Where, as here, the approach and decompression technique are familiar to spinal surgeons, and where standard equipment and instruments can be used, these known technologies should be considered as a base from which further innovation can be made.

However, the anatomic window of Kambin's triangle, through which safe disc access is possible, has very limited dimensions. This access window can be enlarged by resecting at least a part of the superior articular process. But either way, the length of a working shield needed to safely introduce the implant to the intervertebral space via this approach must be in the region of about 8-12 mm in diameter, reaching from the facet joint line to the disc entry point.

SUMMARY OF THE INVENTION

The present inventors envision introducing a second, inner shield through the above-mentioned first, outer shield. The second inner shield extends past the first outer shield to arrive next to nervous tissue, thereby shielding the nerves from instruments or devices passing through to the disc space. During this step, the outer shield allows the visual, safe placement of the inner shield.

In one embodiment, there is provided an outer shield (which can be, for example, a tube or a blade) comprising an access shield with a larger diameter (~12-30 mm) that reaches from the skin down to the bone line, with an inner shield having a second smaller diameter (~5-12 mm) extending past the access shield and reaches down to the disc level. This combines the benefits of the direct visual from microsurgical/mini open approaches and percutaneous techniques (FIGS. 1a-1b and 2).

The outer shield has a number of features and advantages. First, it enables separation and protection of surrounding of soft tissue and visualization during a standard microsurgical decompression/bone resection work under microscopic view—based on a standard procedure that a surgeon who is familiar with MIS techniques is able to perform. Second, it enables separation and protection of surrounding of soft tissue and visualization during detection and removal of the facet joint, or parts of the facet joint—based on a standard procedure that a surgeon who is familiar with MIS technique is able to perform. Third, it enables identification, preparation and protection of sensitive (e.g., neural) tissue (exiting nerve root, traversing nerve root, dura) under direct visual control underneath the border between retraction-sensitive and non-retraction sensitive tissues (e.g., the facet line) based on a standard procedure that a surgeon who is familiar with MIS technique is able to perform. Fourth, it enables insertion of the inner shield and potential docking of the inner shield in the disc space or at the vertebrae under direct visual control.

Likewise, the inner shield has a number of features and advantages. First, it enables protection of nervous tissue (exiting nerve root, transverse nerve root, dura) against instruments that are introduced into the intervertebral disc. Second, it enables guidance of intradiscal instrumentation (discectomy instruments, visualization instruments, discectomy verification instruments, implant insertion instruments, bone graft filling instruments). Third, because of its small size, the shield can be inserted with minimal damage or trauma to bone and soft tissue in the area of the posterior column of the spine, comparable to percutaneous access instruments Therefore, in accordance with the present invention, there is provided a method of accessing an intervertebral disc in a patient, comprising the steps of:
  a) making an incision in a skin of the patient,
  b) percutaneously inserting through the incision an outer shield having a substantially tubular shape (such as a tube or a multi-slotted retractor), the outer shield having a length adapted to extend from the incision to a border between sensitive and insensitive tissue (e.g., a superior articular process (SAP), or a lamina), in the spine of the patient,
  c) stabilization of this outer shield to a pedicle anchor,
  d) insertion of an outer shield integrated optical visualization instrument,
  e) resecting a portion of the superior articular process, and/or performing a microsurgical decompression procedure,
  f) inserting or deploying an inner shield through or from the outer shield so that a distal end portion of the inner shield extends to the disc, the inner shield having an outer surface,
  g) contacting the outer surface of the shield to a nerve root to shield the nerve root,
  h) microsurgical decompression of any tissue deemed to be causing nerve impingement,
  i) extraction of the intervertebral disc material including the removal of the cartilaginous material from the vertebral endplates,
  j) insertion of the interbody device, and
  k) deployment of a mechanism of stabilization to stabilize the intervertebral segment.

Also in accordance with the present invention, there is provided a method of accessing an intervertebral disc in a patient, comprising the steps of:
  a) making an incision in a skin of the patient,
  b) percutaneously inserting through the incision an outer shield having a substantially tubular shape,
  c) stabilization of this outer shield to a pedicle anchor,
  d) inserting an inner shield through the outer shield so that a distal end portion of the inner shield extends to the disc, the inner shield having an outer surface,
  e) contacting the outer surface of the shield to a nerve root to shield the nerve root,
  f) microsurgical decompression of any tissue deemed to be causing nerve impingement,
  g) extraction of the intervertebral disc material including the removal of the cartilaginous material from the vertebral endplates, h) insertion of the interbody device, and i) deployment of a mechanism of stabilization to stabilize the intervertebral segment.

Also in accordance with the present invention, there is provided an access device for accessing an intervertebral disc, comprising:

a) an outer shield having a substantially tubular portion, a length adapted to extend from an incision to a border between sensitive and insensitive tissue (e.g., an articular process or a lamina), a proximal end portion, a distal end portion, an outer surface, and a longitudinal throughbore defining an inner surface, b) an inner shield having i) a first substantially tubular portion having a proximal end portion, a distal end portion, a longitudinal through-bore defining an inner surface, and an outer surface defining a diameter, and ii) a longitudinal flange extending distally from the distal end portion of the substantially tubular portion, wherein the outer surface of the inner shield substantially nests within the inner surface of the outer shield so that the flange extends distally past the distal end portion of the outer shield.

DESCRIPTION OF THE FIGURES

FIG. 4 shows a necked, funnel-shaped embodiment of the inner shield;

FIGS. 5-6 show different longitudinal cross sections of concentric and nonconcentric inner shields;

FIG. 7 shows a jointed access device;

FIGS. 15a-15b show inner shield having proximal elbows;

FIG. 16 shows an access device with a distal sharpened tip on the inner shield within an outer shield;

DETAILED DESCRIPTION OF THE INVENTION

Figure 1A:
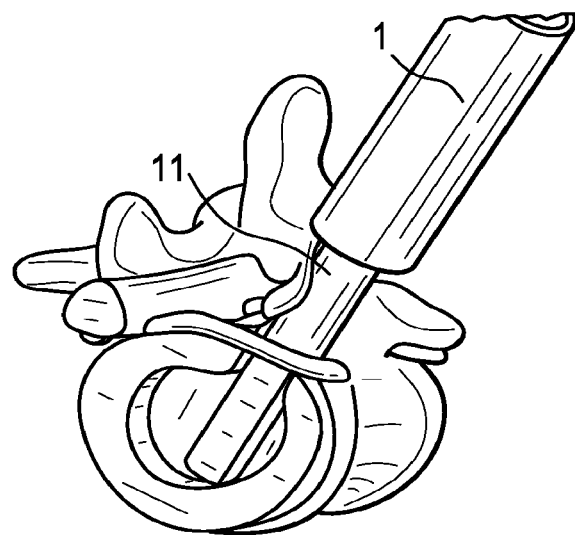
FIG. 1a shows an interbody device delivered through the access device.
Figure 1B:
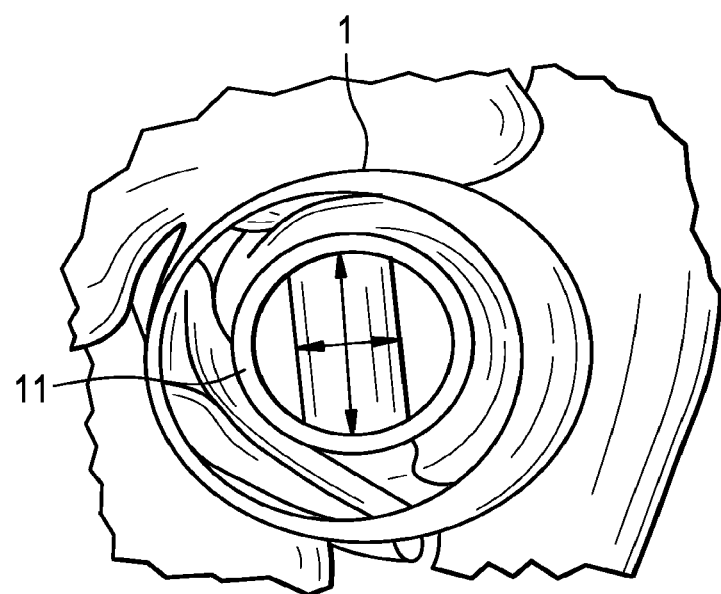
FIG. 1b shows an end view of the access device.
Figure 2A:
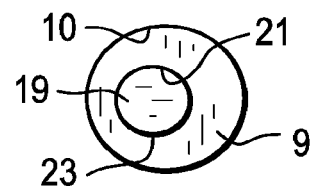
FIGS. 2a and 2b are different views of a tube-in-tube embodiment of the access device.
Figure 2B:
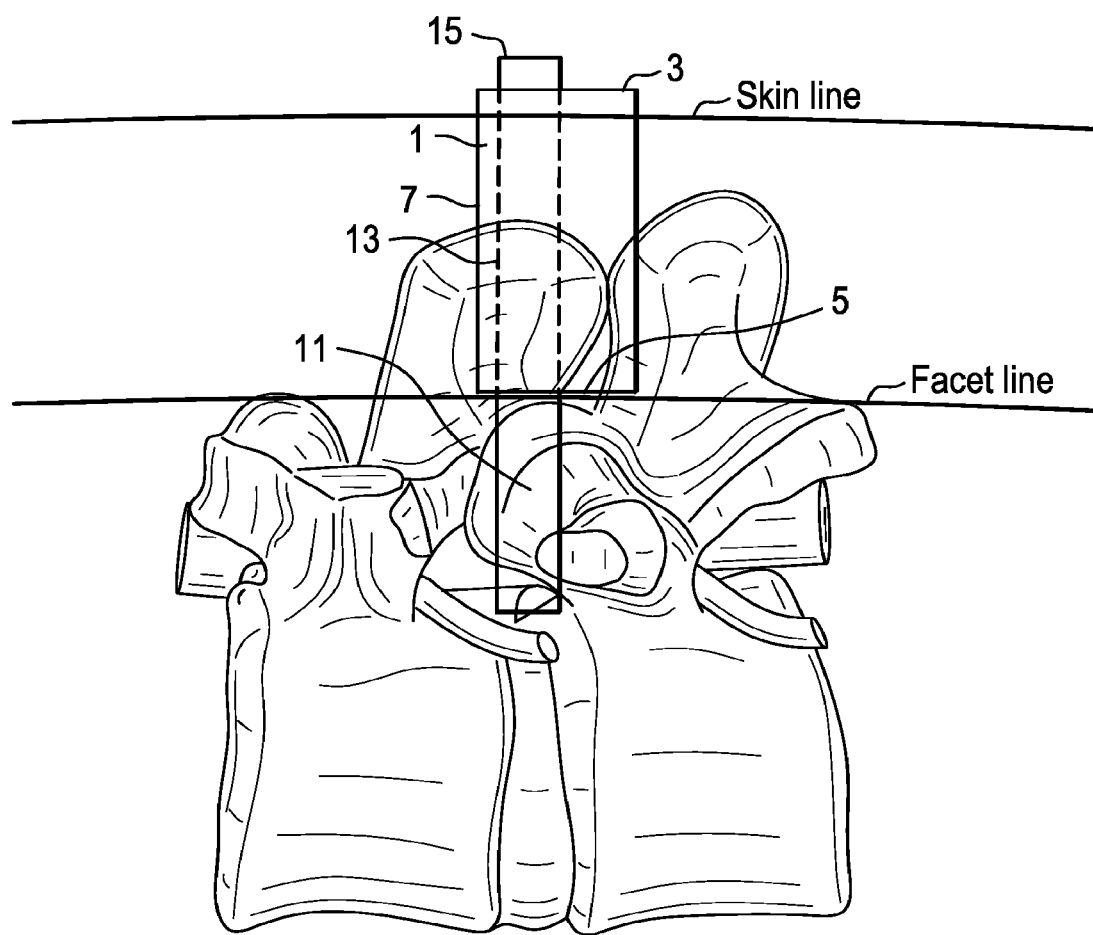

Fluoroscopic visualization is performed to define the incision site of the initial reference array placement, as well as the incision for access to the intervertebral disc.

Generally, the shields of the present invention can be applied to any of the conventional approaches commonly used in spine surgery. However, given the clinical benefit of the access device and its underlying rationale, it is preferably suitable to use these shields in either interlaminar, extraforaminal or transforaminal approaches to the intervertebral disc.

Now referring to FIGS. 1-7, there is provided an access device for accessing an intervertebral disc, comprising:

a) an outer shield 1 having a substantially tubular portion, a length adapted to extend from an incision to a border between sensitive and insensitive tissue (e.g., an articular process), a proximal end portion 3, a distal end portion 5, an outer surface 7, and a longitudinal through-bore 9 defining an inner surface 10, b) an inner shield 11 having i) a first substantially tubular portion 13 having a proximal end portion 15, a distal end portion 17, a longitudinal through-bore 19 defining an inner surface 21, and an outer surface 23 defining a diameter, and ii) a longitudinal flange 25 extending distally from the distal end portion of the substantially tubular portion, wherein the outer surface of the inner shield substantially nests within the inner surface of the outer shield so that the flange extends distally past the distal end portion of the outer shield, and the distal end portion of the substantially tubular portion of the inner shield extends distally past the distal end of the outer shield.

Outer Shield Embodiments

Figure 3A:
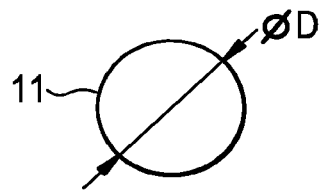
FIGS. 3a-3d show different axial cross section of the inner shield.
Figure 3B:
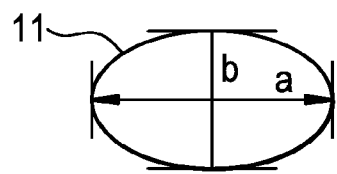
Figure 3C:
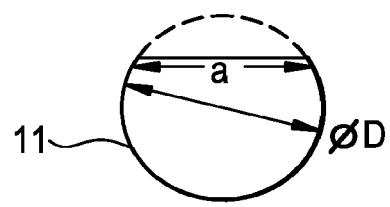
Figure 3D:
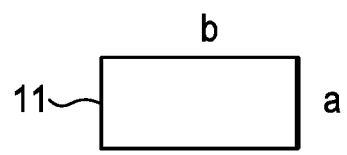

In the design of the outer shield, traditional tube or split tube/retractor concepts can be used. Newer concepts such as a "flexible tube" could also be adopted. The outer shield can be a simple cylindrical tube. It may also be a split tube, in the manner that conventional retractors are considered to be split tubes. It can be a flexible tube. It can be a tube with a slot running from the proximal end to the distal end. Various shape embodiments could be:

a) a cylindrical tube with an inner diameter D (FIG. 3*a*);

b) an oval tube with a height a different than a length b (FIG. 3*b*);

c) a "half moon" tube having a substantially circular or oval cross section of diameter D, with a section cut (or chord) "a" (FIG. 3*c*); and d) a rectangular tube with height a and width b (FIG. 3*d*).

In some embodiments, the shape of the distal end portion 5 includes an unsymmetrical shape for better tissue retraction lateral to the SAP.

The outer shield can be preferably used with a variety of access window sizes (i.e., widths) ranging from 6 mm to 25 mm and lengths ranging from 40 mm to 200 mm. Typically, the outer shield comprises a feature that allows for the attachment of a stabilization mechanism that allows for appropriate flexibility in attachment (e.g. a ball joint). In one embodiment, the outer shield has a customized feature adapted for the introduction of an endoscope or camera that allows the endoscope to be introduced to a predetermined depth where the working window at the distal portion of the outer shield can be visualized.

Inner Shield Embodiments

Now referring to FIGS. 3*a-d*, the inner shield 11 may encompass various designs as well.

In a first embodiment, the inner shield is a fully surrounding (i.e., extending for 360 degrees) stiff tube. It may possess various cross-sections, such as:

e) a cylindrical tube with an inner diameter D (FIG. 3*a*);

f) an oval tube with a height a different than a length b (FIG. 3*b*);

g) a "half moon" tube having a circular cross section of diameter D, with a section cut (or chord) "a" (FIG. 3*c*); and h) a rectangular tube with height a and width b (FIG. 3*d*).

The inner shield may possess different longitudinal shapes. For example, in a second embodiment, and now referring to FIGS. 4-7, the inner shield 11 is a funnel-shaped (e.g. necked) tube (as in FIG. 4). In this embodiment, it changes its cross sectional shape/area along the shield, with a bigger diameter/working zone at the proximal portion, and the length of this zone with a bigger diameter is adjusted to be the part of the inner shield that will be nested within the outer shield, and a smaller diameter/working zone where the inner shield is extending the outer shield.

This design increases the range of motion of intradiscal tools and enables better visualization. In FIG. 4, the flange is a second substantially tubular portion 25 having a diameter less than the diameter of the first substantially tubular portion 13 of the inner shield. A necked region 27 is disposed between the first and second substantially tubular portions.

In some embodiments, the inner shield may be in the form of one of a plurality of retractor blades.

In tubular embodiments, the smaller tube can be a concentric with the larger tube, or not concentric therewith. In FIG. 5, the first and second substantially tubular portions of the inner shield are concentric (a=b). In FIG. 6, the first and second substantially tubular portions of the inner shield are not concentric (a>b).

In some embodiments, there is provided a spherical joint between the larger and the smaller tubes, allowing the angle to change between the two tubes (FIG. 7). In FIG. 7, the outer surface 23 of the inner shield substantially nests within the inner surface 10 of the outer shield so that the proximal end of the substantially tubular portion of the inner shield terminates within the outer shield. Also, the distal end portion of the inner shield narrows distally to define a first radius R1, and the proximal end portion of the inner shield narrows distally to define a second radius, and the proximal end portion of the inner shield nests within the distal end portion of the outer shield to allow polyaxial pivoting of the inner shield.

In some embodiments, the inner shield is a partially surrounding tube/shield, or "flange," designed only to protect the nerves. For some applications, the only purpose of the inner tube might be to shield/protect the exiting nerve root. In this case, the inner shield might be simplified to a cylinder with a flange 25 extending distally therefrom, so that the flange is only a shield of about a quarter of a full circle. See FIG. 8*a*, or FIG. 9 if mounted on the outer shield.

Depth Adjustment of Nerve Protector

The aforementioned outer shield can be positioned and fixed in its depth through a mechanism which relies on interference between the outer shield and the inner shield at any location along either the outer shield or inner shield.

Figure 8B:
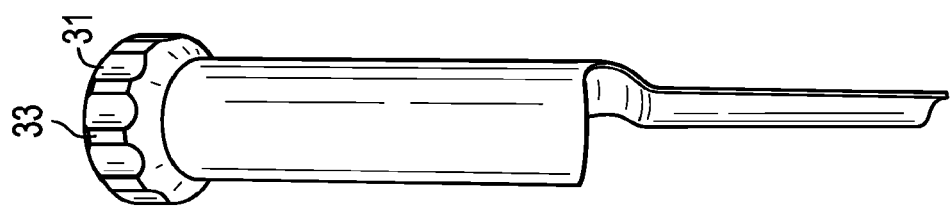
FIG. 8b shows an inner shield with a proximal stop.
Figure 8A:
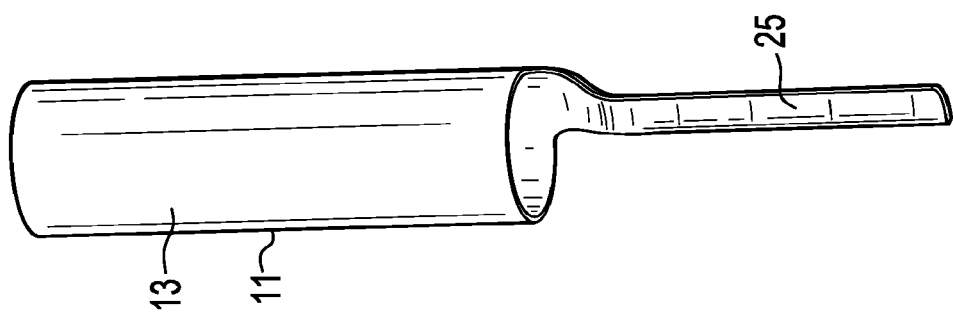
FIG. 8a shows a flanged embodiment of the inner shield.

In FIG. 8*b*, the proximal end portion of the first substantially tubular portion 13 of the inner shield comprises a stop 31 adapted to abut the proximal end portion of the outer shield, the stop being adapted to prevent excessive distal movement of the inner shield. Preferably, the stop extends substantially radially about the proximal end portion of the substantially tubular portion of the inner shield. The stop may also further comprise a textured radial surface 33 adapted for gripping. It acts as both a stop and as a handle to twist the shield.

Figure 9:
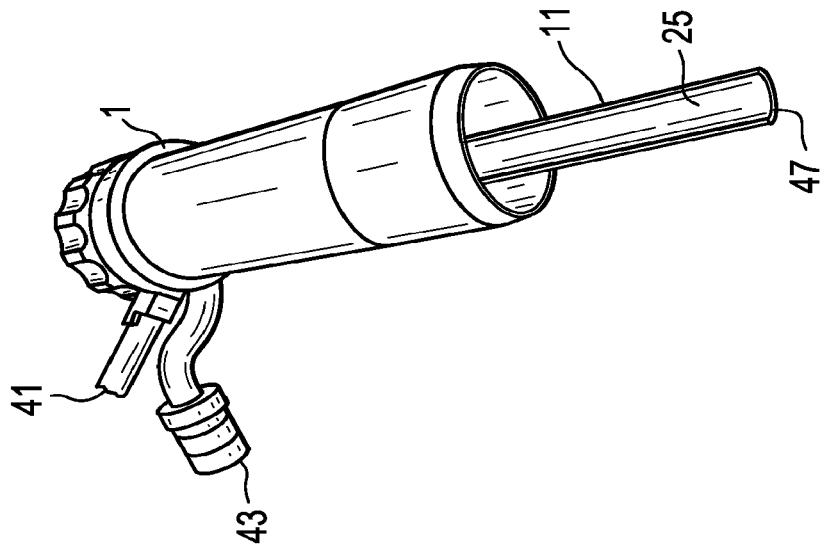
FIG. 9 shows an access device with two ports attached to the outer shield, one port is a connector to hold the outer tube, while the other is an interface for a light source.

In FIG. 9, the outer surface of the inner shield substantially nests within the inner surface of the outer shield so that the proximal end portion of the substantially tubular portion of the inner shield extends proximally past the proximal end of the outer shield. Also in FIG. 9, the outer surface of the outer shield further comprises a first port 41 adapted for connecting to a navigation instrument or a stabilization point, and a second port 43 adapted for connecting to a camera/light system.

Navigation of Outer Shield

The first port allows the outer shield to be navigated to determine its position (depth and orientation) in relation to the treatment site. In one embodiment, the outer surface of the outer shield has a feature that allows for the direct or indirect attachment of a navigation instrument. In another embodiment, the inner surface of the outer shield has a feature that allows for the direct or indirect attachment of a navigation instrument.

Endoscope in the Outer Shield

In some embodiments, the outer shield has an integrated endoscope that can be set in a fixed or variable (angle or circumferential) position relative to the anatomy. This endoscopic visualization can be utilized in subsequent surgical steps, including bone removal, inner shield deployment, discectomy and implant insertion. Preferably, the endoscope has an integrated lens cleaning mechanism for automated lens cleaning in situ.

Figure 10:
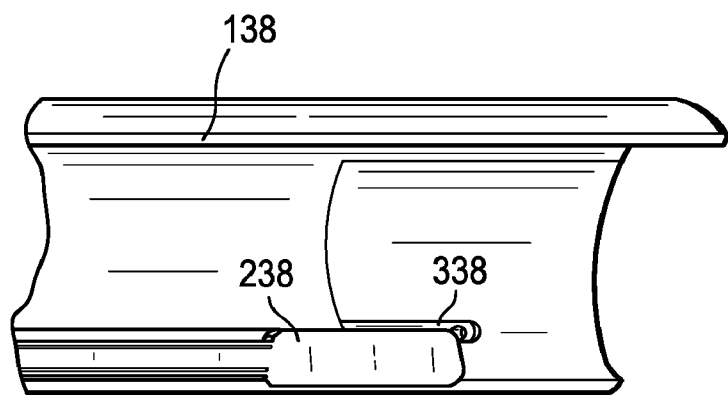
FIG. 10 discloses a cross-section of an outer tube wherein the outer tube wall has a first channel adapted for containing a visualization unit (such as a camera) and a second channel adapted for containing a cleaning system (such as a lens cleaning device)

FIG. 10 discloses a cross-section of an outer tube wherein the outer tube wall 138 has a first channel 238 adapted for containing a camera and a second channel 338 adapted for containing a lens cleaning device.

Figure 11:
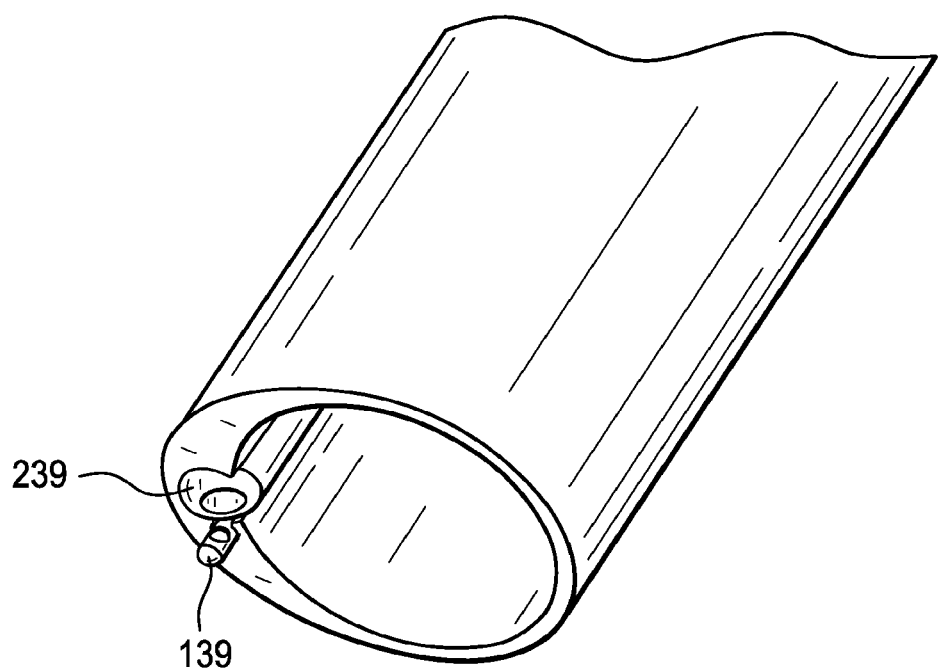
FIG. 11 discloses a cross-section of an outer tube wherein the outer tube wall contains a lens cleaning device and a camera.

FIG. 11 discloses a cross-section of an outer tube wherein the outer tube wall contains a lens cleaning device 139 and a camera 239.

Figure 12:
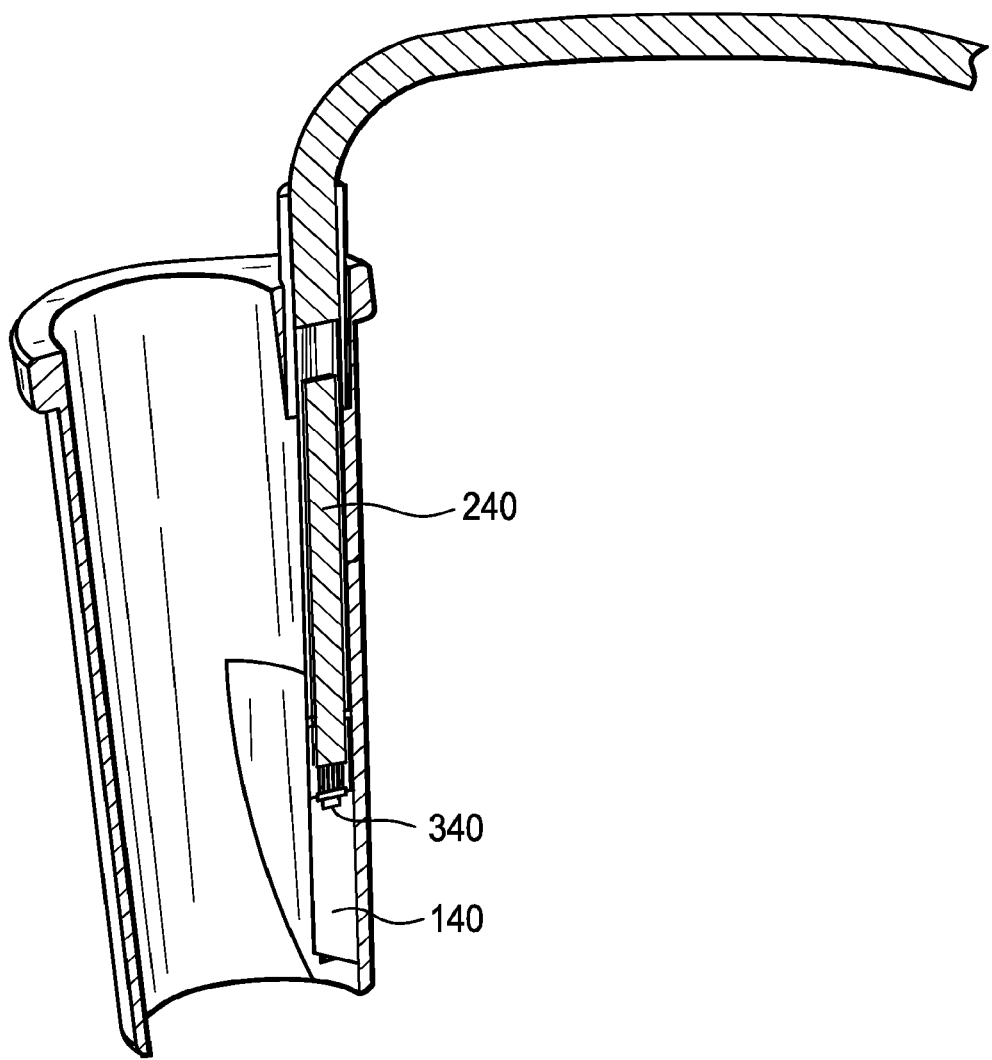
FIG. 12 discloses a chip-on-tip embodiment including a cross-section of an outer tube wherein the outer tube wall has a channel containing an endoscope having a video chip near its distal end.

FIG. 12 discloses a chip-on-tip embodiment including a cross-section of an outer tube wherein the outer tube wall has a channel 140 containing an endoscope 240 having a video chip 340 near its distal end.

Figure 13:
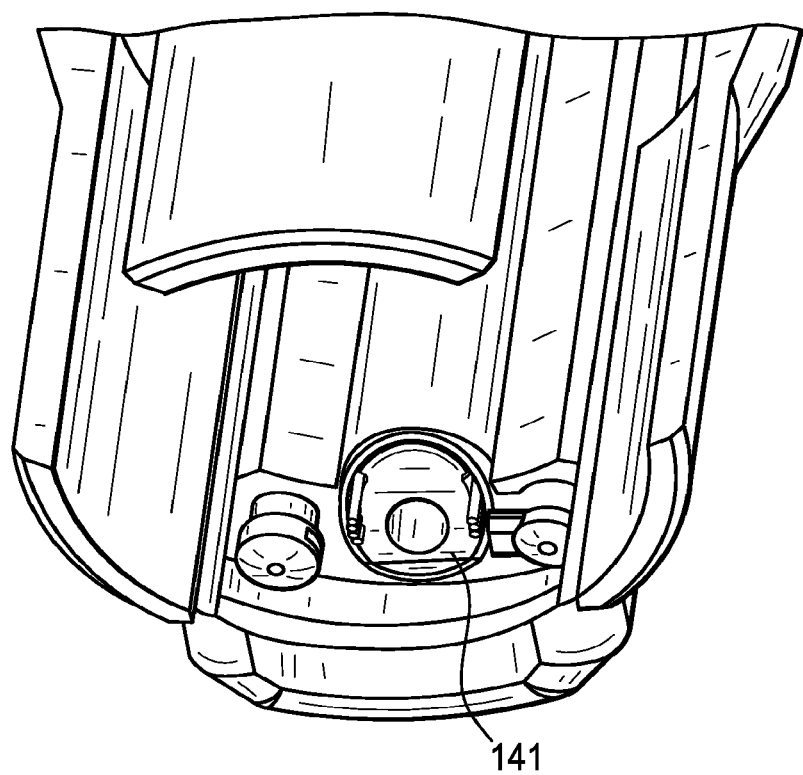
FIG. 13 discloses a distal end of an outer tube featuring a video chip near its distal end.

FIG. 13 discloses a distal end of an outer tube featuring a video chip 141 near its distal end.

Fixed Endoscope

The endoscope can be a chip-on-tip type of endoscope having an outer diameter less than 5 mm and having an incremental length substantially matching the length of the outer shield. The benefits of an integrated chip-on-tip endoscope/outer shield embodiment include the relatively free space within the bore of the outer shield, thereby enhancing visualization.

Preferably, the endoscope is angled within the port or has a built-in lens angle such that, at final positioning within the port, the circumference of the distal portion of the outer shield is visible and the area within the circumference is visible as well.

In some embodiments, the endoscope can be removed from the wall of the outer shield and inserted independently into the outer shield bore to inspect the treatment site (e.g. into the disc space for confirmation of adequate discectomy).

Figure 14:
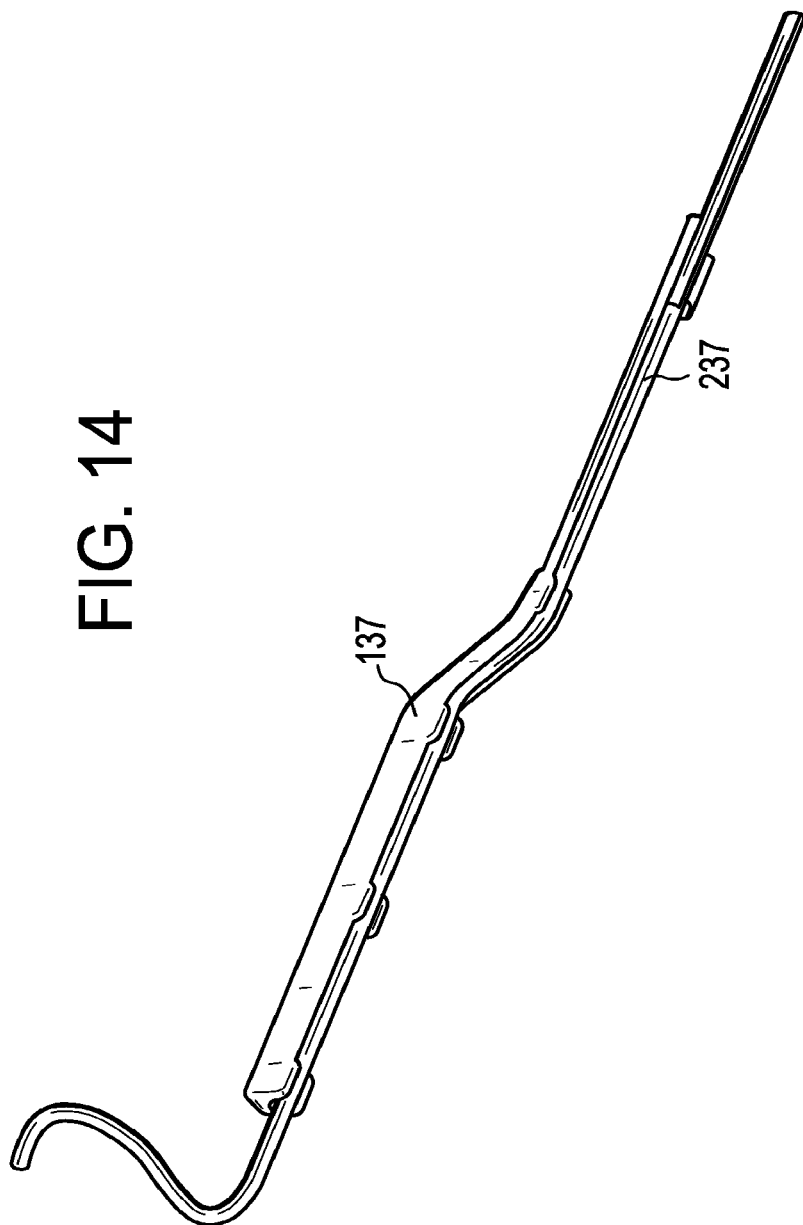
FIG. 14 discloses a scope holder for an endoscope.

FIG. 14 discloses a scope holder 137 for an endoscope 237.

Still referring to FIG. 9, in some embodiments, the flange 25 of the inner shield has an arcuate transverse cross-section. In some embodiments, the arcuate transverse cross-section of the flange defines an outer surface 47 of the flange having a curvature substantially similar to a curvature of the inner surface 10 of the outer shield. Preferably, the flange defines a second substantially tubular portion having a diameter less than or equal to the diameter of the first substantially tubular portion of the inner shield.

Now referring to FIGS. 15a-15b and 16, the inner shield can be a single blade that can be mounted/hooked to the outer tube. In this case, elbow 51 functions as a stop and also as a connector to the outer tube. Also, the proximal end of the inner shield may form an anchoring spike 53.

There are a number of ways to fix or locate the inner shield onto the disc and/or onto the outer shield. In one embodiment, which provides safety of the inner shield against slippage/dislocation, involves mounting it distally (onto or within the vertebral endplates or disc annulus) and/or proximally (onto the outer shield).

Distal fixation of the inner shield with the anatomy may include: a) fixation within disc annulus, b) fixation against vertebrae; c) fixation against other structures; d) K-Wires that are distally extending through the walls of the inner shield and anchored to the anatomy; and e) spikes extending the distal part (FIG. 15) to be anchored to the anatomy.

Figure 17:
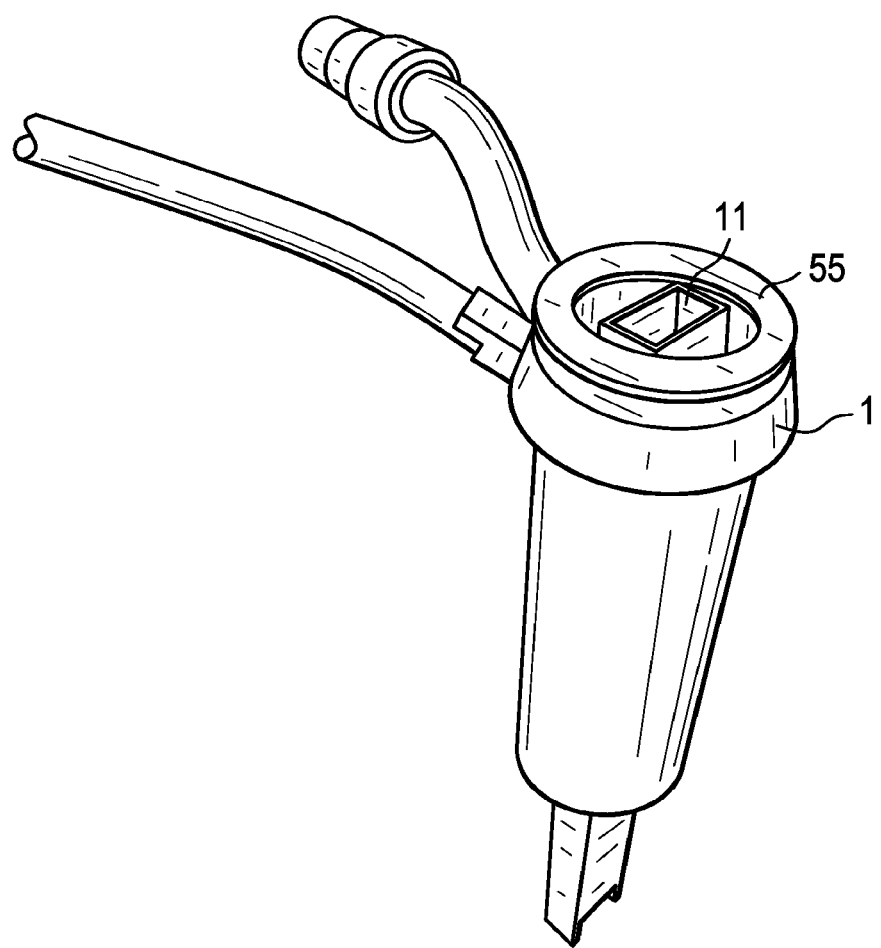
FIG. 17 shows an access device with a positioning ring between the inner and outer shields.

Proximal fixation of inner shield upon the outer shield may involve a positioning ring or a depth adjustment. Now referring to FIG. 17, proximal fixation of inner shield upon the outer shield may involve a positioning ring 55. Assuming the outer shield would be fixed relative to the anatomy, there would be the option of having positioning rings having the shape of the outer tube at the outside, and of the inner tube on the inside. When placed over the inner shield and into the outer shield, such a ring would stabilize the location or at least the orientation of the proximal inner shield against the outer shield, and by considering the assumption above also against the anatomy.

Figure 18:
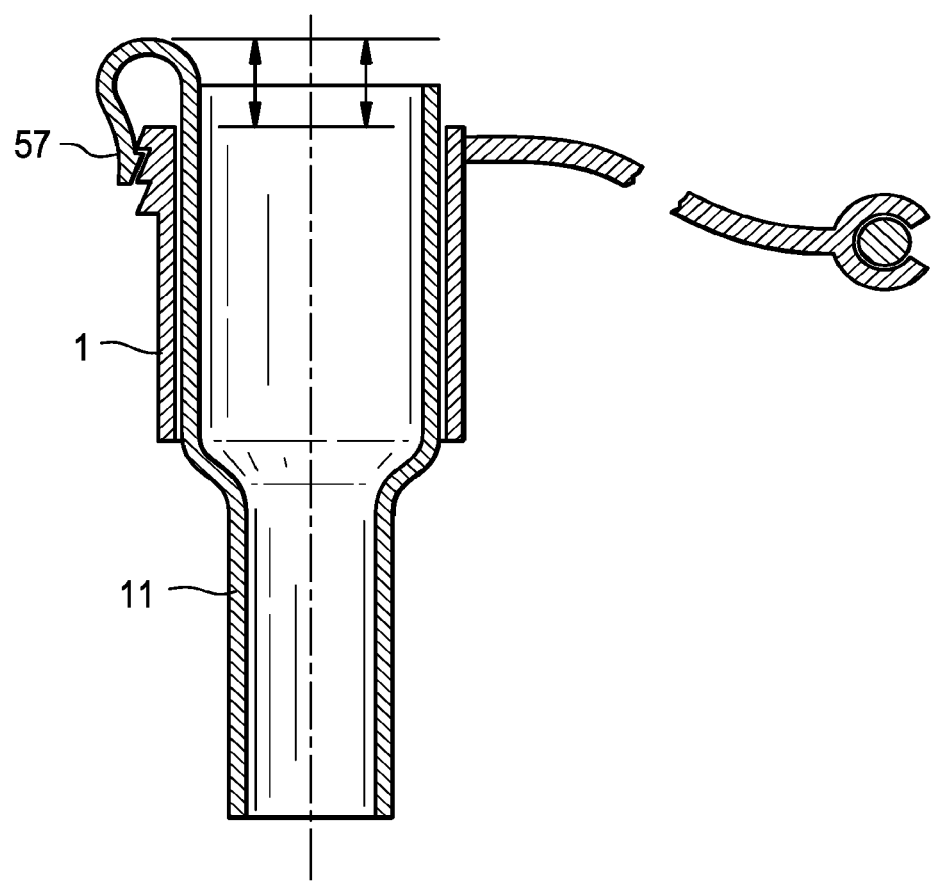
FIG. 18 shows an access device with a depth adjustment means formed by the inner and outer shields.

Now referring to FIG. 18, proximal fixation of inner shield upon the outer shield may involve a depth adjustment means 57. This would additionally stabilize or anchor the tip location of inner shield against the anatomy via anchoring or hooking the inner shield into the outer shield via ratchet system. The ratchet system can also be located between the inner surface of the outer shield, and the outer surface of the inner shield or within the wall of the outer shield. It may further include a spring system to increase friction between the inner and outer shields.

Inner Shield Deployment (Circumferential)

Embodiments having separate outer and inner shields allow for the independent positioning of the inner shield relative to the outer shield. Also, the use of a smaller inner shield (relative to the outer shield) allows for maximum visualization at the entrance where no retraction-sensitive tissues reside. This maximum visualization allows for accurate placement of the inner shield. Where retraction-sensitive tissues reside distal the outer shield, a relatively smaller inner shield allows for minimum retraction while providing an access through or past these tissues. Preferably, the inner diameter of the inner shield is no more than 40%-100% of the inner diameter of the outer shield.

In some embodiments, the inner shield-outer shield configuration is replaced by a) a primary shield having a substantially tubular shape having a cutout, and b) a secondary shield having a shape that is substantially insertable into the cutout. Preferably, the primary shield has a substantially annular shape and the secondary shield has an arcuate cross-section that substantially matches the annular shape of the primary shield. This embodiment allows the secondary shield to be tilted with respect to the primary shield.

Inner Shield Deployment (Radial)

In another nerve protection embodiment, the motion of retraction of the shields is radial rather than rotational. In these embodiments, a straight or bayonetted inner shield may be used. The inner shield may be positioned over the area in which the protected tissue is to be located. The flange shield can then be angled into the center of the access window at the distal end of the outer shield e.g. towards the caudal pedicle. It can then be subsequently advanced longitudinally onto the medial side of the nerve root, into the "safe zone" as described by Kambin. It is subsequently angled such that the distal tip of the inner shield is angled laterally, wherein its outer distal surface gently pushes the exiting nerve root away and/or shields it against the tools that are further introduced medially to the shield for intradiscal work. This embodiment may be constructed such that the inner shield substantially nests either a) within the wall of the outer shield (FIG. 19), b) inside the inner surface of the outer shield (FIG. 21), or c) outside the outer surface of the outer shield. In some embodiments, the inner shield is built into the wall of the outer shield or even outside the outer shield.

Figure 19:
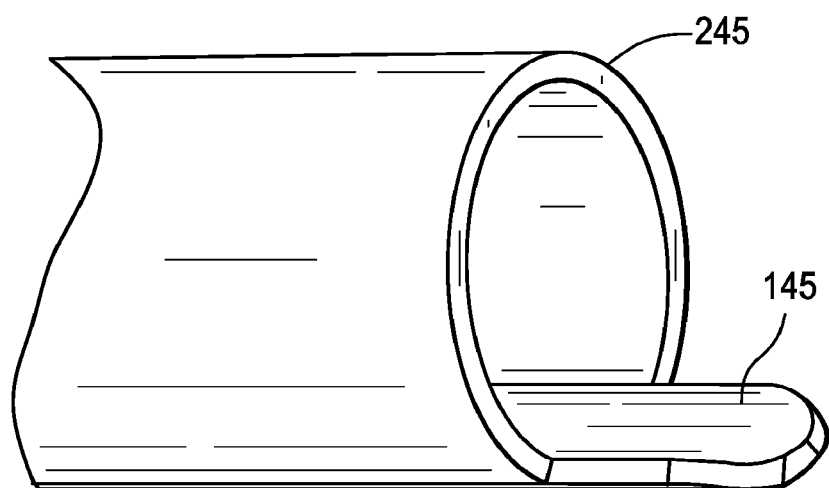
FIG. 19 discloses an integrated retractor having a flat inner face housed within a cutout of an outer tube 245.
Figure 20:
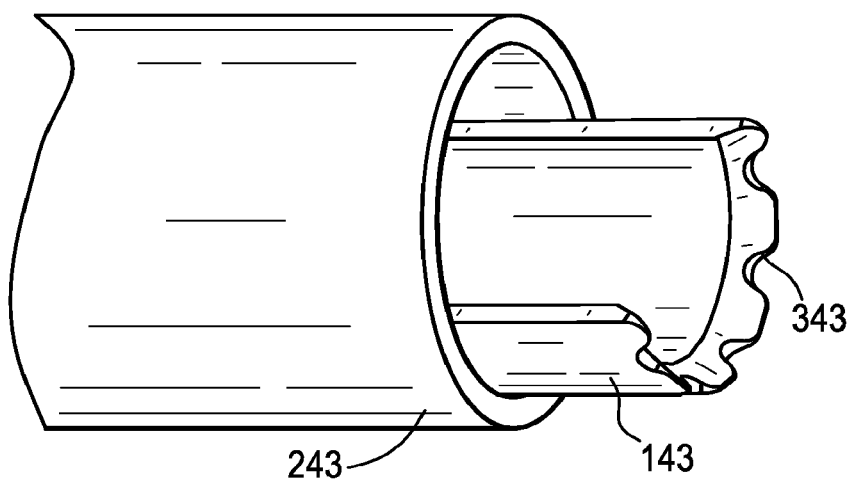
FIG. 20 shows the embodiment of FIG. 48.

FIG. 19 discloses an integrated retractor having a flat inner face 145 housed within a cutout of an outer tube 245.

Figure 21:
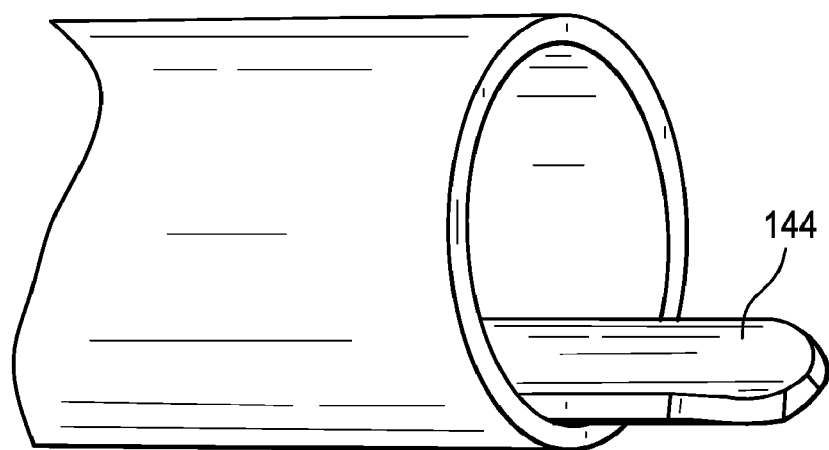
FIG. 21 discloses a retractor having a flat inner face housed within an outer tube.

FIG. 21 discloses a retractor having a flat inner face 144 housed within an outer tube.

In other embodiments, an outer tube can have a retractor nesting with the outer face of the outer tube.

Depth Control of Nerve Protector

The aforementioned outer shield can be controlled in its depth through a mechanism that relies on interference between the outer shield and the inner shield at any location along either the outer shield or inner shield.

There are a number of avenues by which the present device can be used to distract the disc space and/or provide nerve protection upon mounting.

In one distraction embodiment, a revolution spreader is used. This is a conventional concept involves an ovoid or rectangular cross-sectional shaped rod that is inserted into the disc with its smaller dimension directed towards the vertebral endplates. After turning the spreader by 90° under force, the larger dimension is directed towards the vertebral endplates, which distracts the disc by the difference of the two cross sectional dimensions.

In a second distraction embodiment, as now referring to FIGS. 22-24b, the inner shield may comprise a spreader, which includes a frame 60, a cranial blade 61, and a caudal blade 63.

Figure 22:
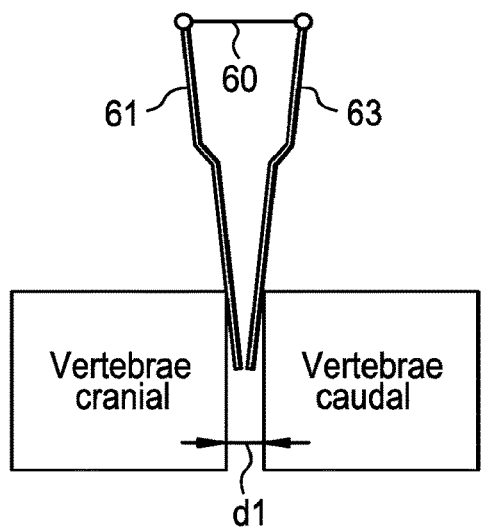
FIGS. 22-24b show a distraction embodiment.
Figure 23:
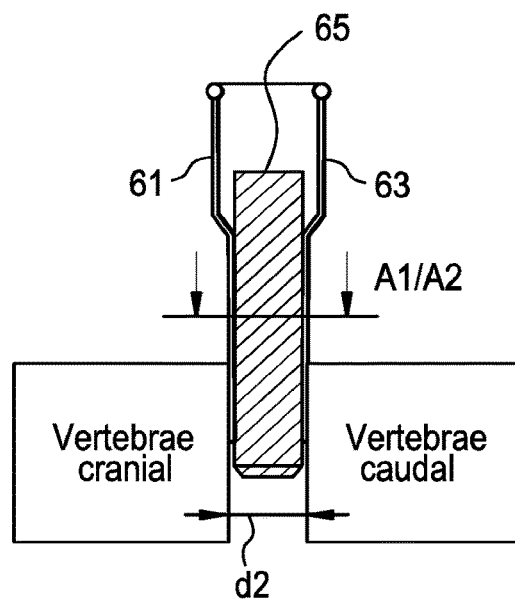
Figure 24A:
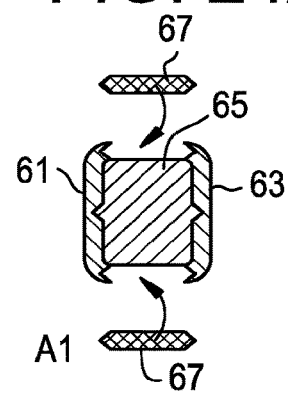
Figure 24B:
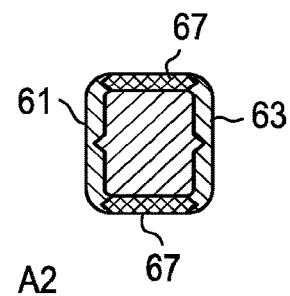

The spreader with respective cranial 61 and caudal 63 distraction blades in cranial and caudal locations is introduced into the disc in a collapsed/tapered configuration (FIG. 22). The spreader blades are then distracted with an inner core 65 (the core matching a counter geometry on the blade to not slip away sideways), elevating the intervertebral height from d1 to d2 (FIGS. 22-23). The side walls 67 matching to the inner core height are then introduced medially/laterally (FIG. 24a), to circumferentially close the four-wall shield. Once the inner core is removed, the stacked shield keeps the vertebral bodies separated in distracted condition (FIG. 24b).

Figure 26:
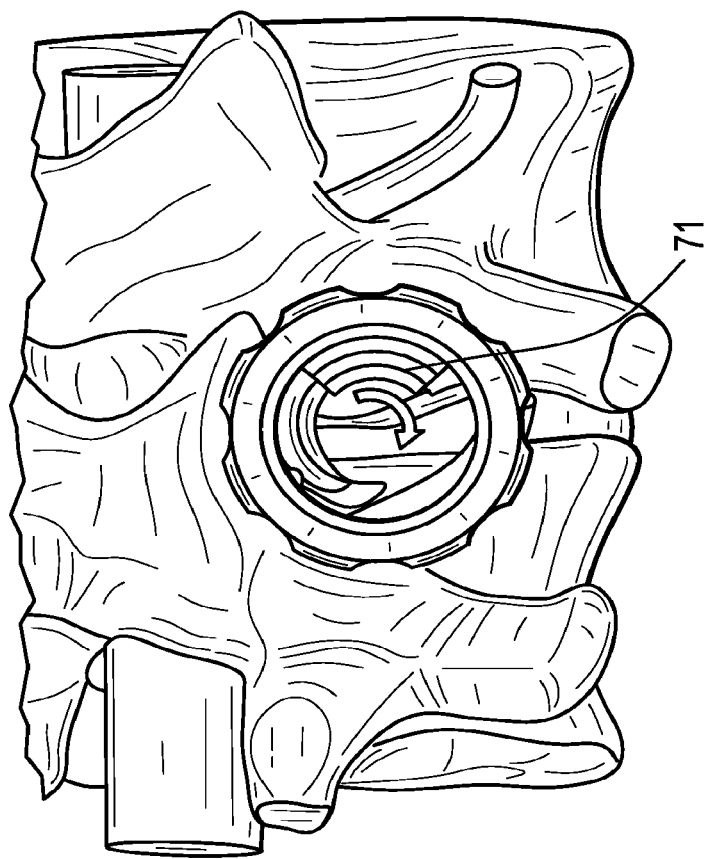
FIGS. 25-30 show an access device with an extending shield.
Figure 25:
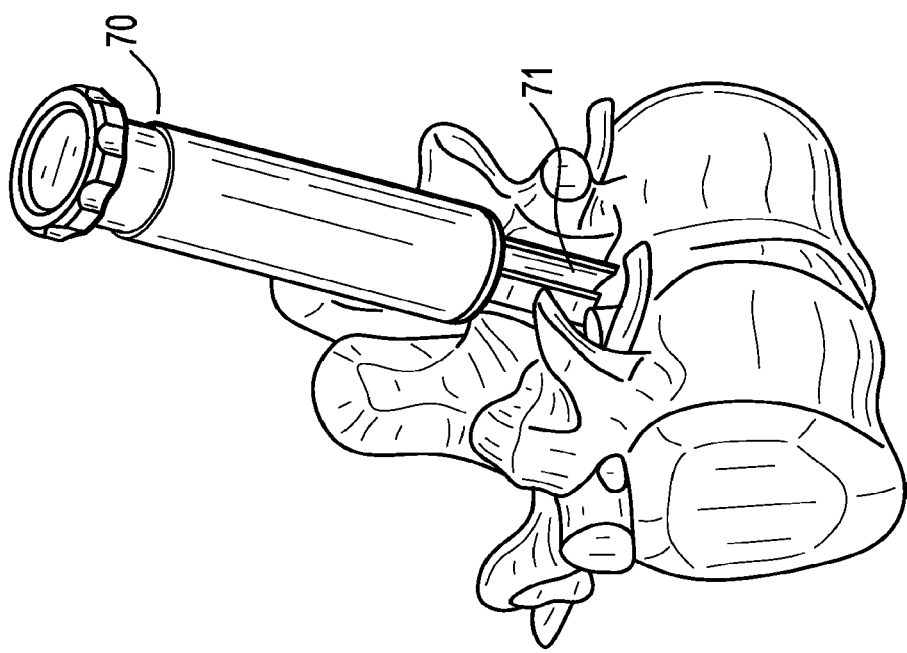
Figure 27:
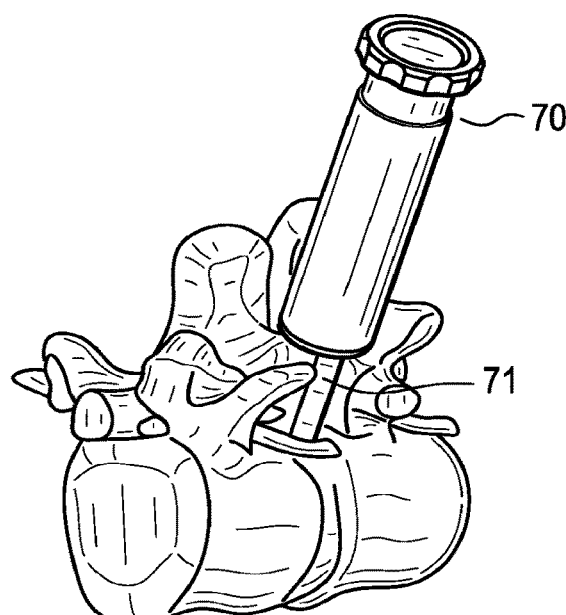
Figure 29:
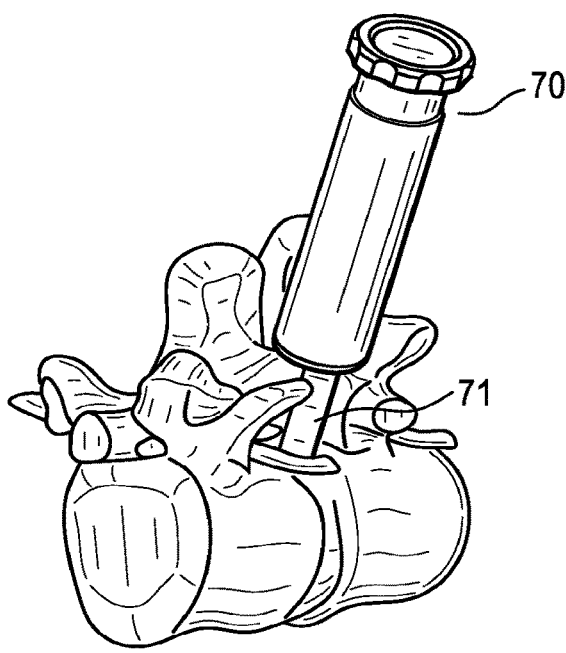
Figure 28:
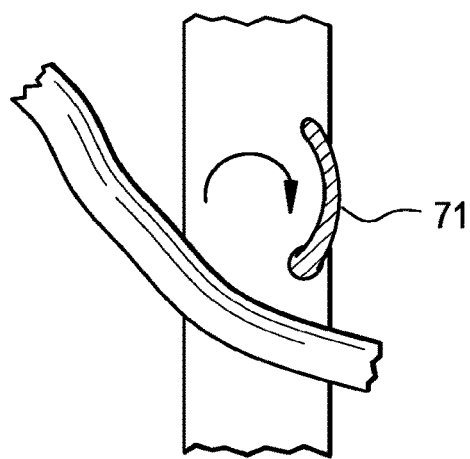
Figure 30:
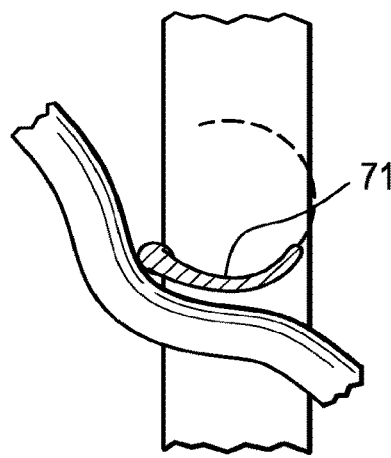
Figure 31:
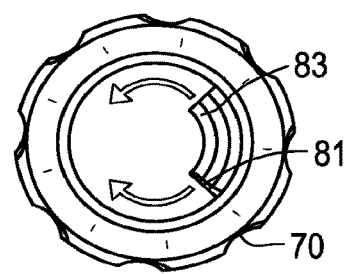
FIG. 31 shows an access device with an inner and outer shield.
Figure 33:
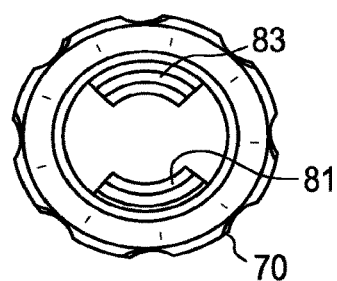
FIGS. 32-34 show in inner shield.
Figure 32:
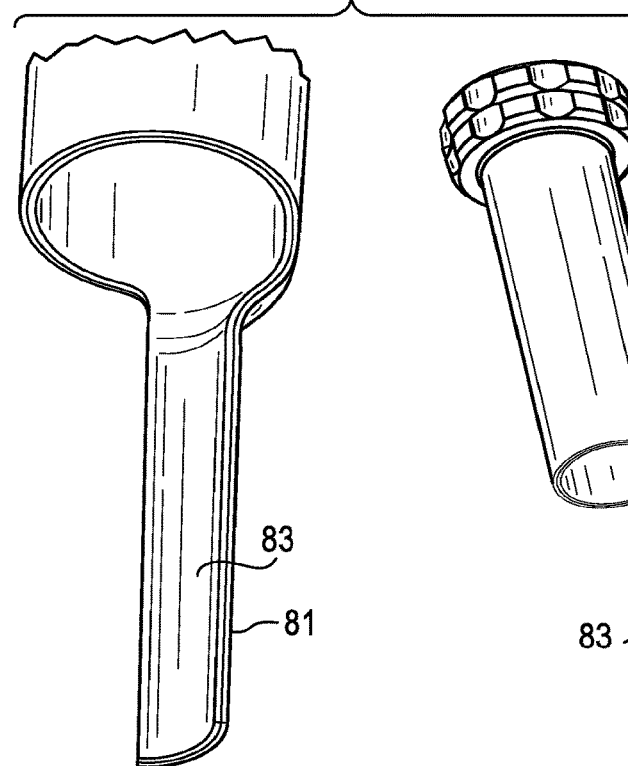
Figure 34:
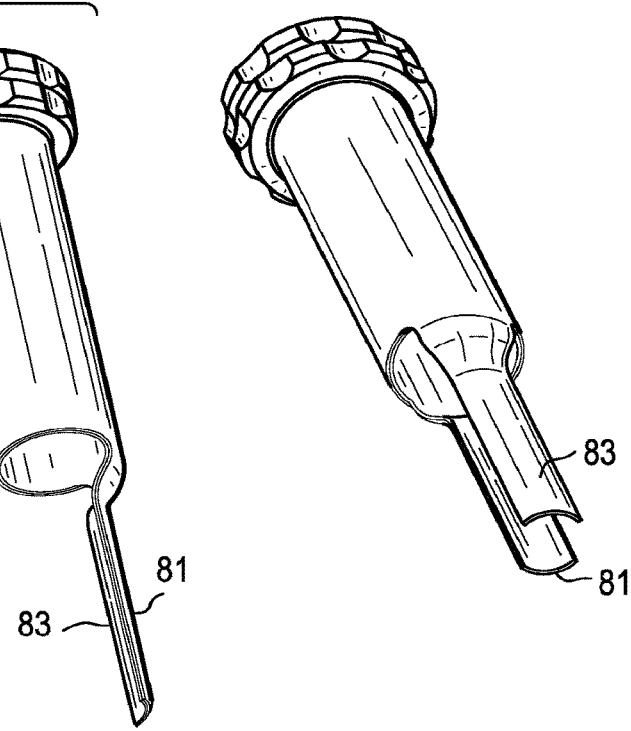

Now referring to FIGS. 25-26, the inner shield may further comprise a rotating flange 71 that moves laterally/medially upon rotation to shield the nerve root.

In a nerve protection embodiment, and now referring to FIGS. 27-30, a rotation funnel 70 is used. Preferably, the flange shield 71 can be smartly introduced to protect the exiting nerve root while being inserted. This shield can be directed towards the caudal pedicle if introduced through the outer shield. This location is a "safe zone" Once the distal tip reaches the disc level, the inner shield can be turned clockwise by about 90° (i.e., rotated), so that the flange gently pushes the exiting nerve root away, and/or shields it against the tools that are further introduced medially to the shield, for intradiscal work.

In a second nerve protection embodiment, and now referring to FIGS. 31-34, a concentrically-arrayed multi-shield is used to gently move and/or shield nerves. The rotation funnel principle can also be applied for more than one rotating shield. A single shield may be suitable if the protection only has to be provided against a structure that lies on one single side. In other situations, however, the shield entry towards the disc would be bounded both medially and laterally by the traversing and the exiting nerves, so the inner shield needs to shield against two opposing structures. In this case, the two concentrically-arranged outer 81 and inner 83 rotating flanges are turned by 90° in respective clockwise and counterclockwise directions to reach an end configuration wherein the opposed shields protect the nerves from the tools that are further introduced for intradiscal work.

In another nerve protection embodiment, a radially-retracting multi-shield is used to gently move and/or shield nerves. The radially-retracting principle can also be applied to more than one radially retracting shield.

Figure 35:
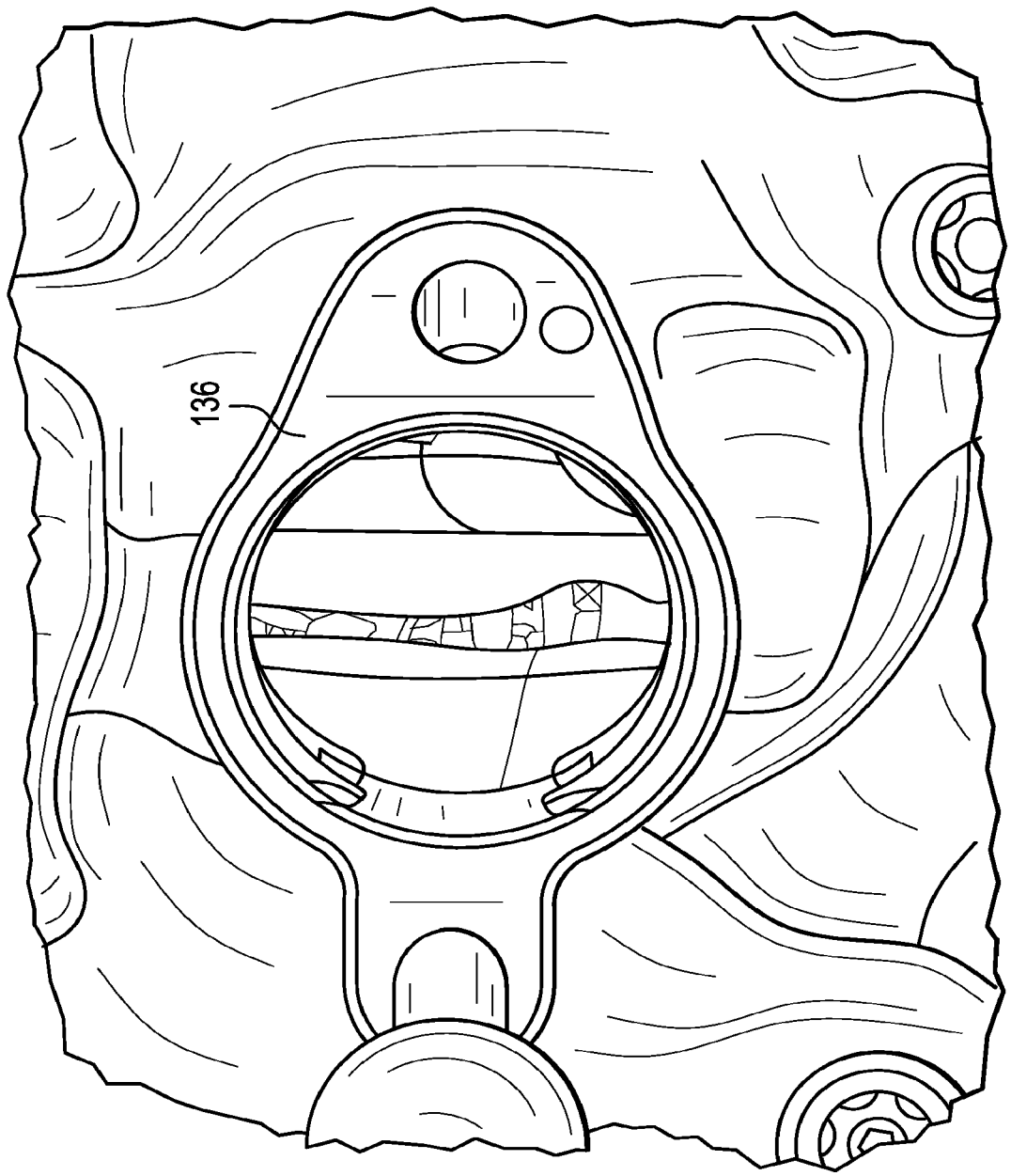
FIG. 35 discloses a radial soft tissue retractor.

FIG. 35 discloses a radial soft tissue retractor 136.

Figure 36:
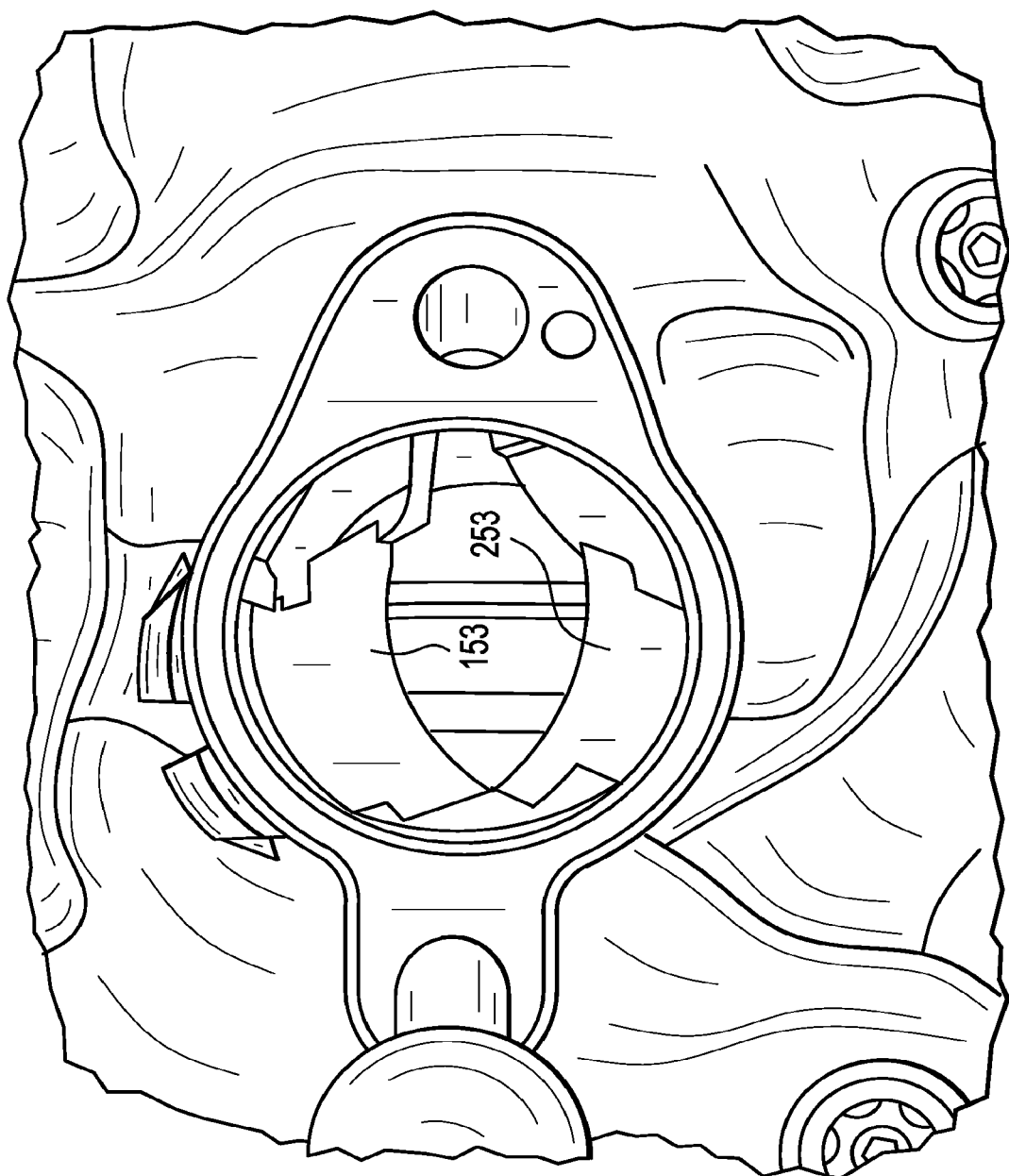
FIG. 36 discloses an outer tube/inner retractor assembly wherein the first inner retractor and second inner retractor both tilt inwards to retract soft tissue.

FIG. 36 discloses an outer tube/inner retractor assembly wherein the first inner retractor 153 and second inner retractor 253 both tilt inwards to retract soft tissue.

A single shield may be suitable if the protection only has to be provided against a structure that lies on one single side. In other situations, however, the shield entry into the disc would be bounded both medially and laterally by the traversing and the exiting nerves, so that the inner shield needs to shield against two opposing structures. In this case, the two opposing inner flanges are initially positioned towards the center of the outer tube access window and subsequently retracted outwards to shield the opposing nerves from the tools that are further introduced for intradiscal work.

FIGS. 37-46 disclose a preferred method of surgery involving the tube-in-tube access device.

Figure 37:
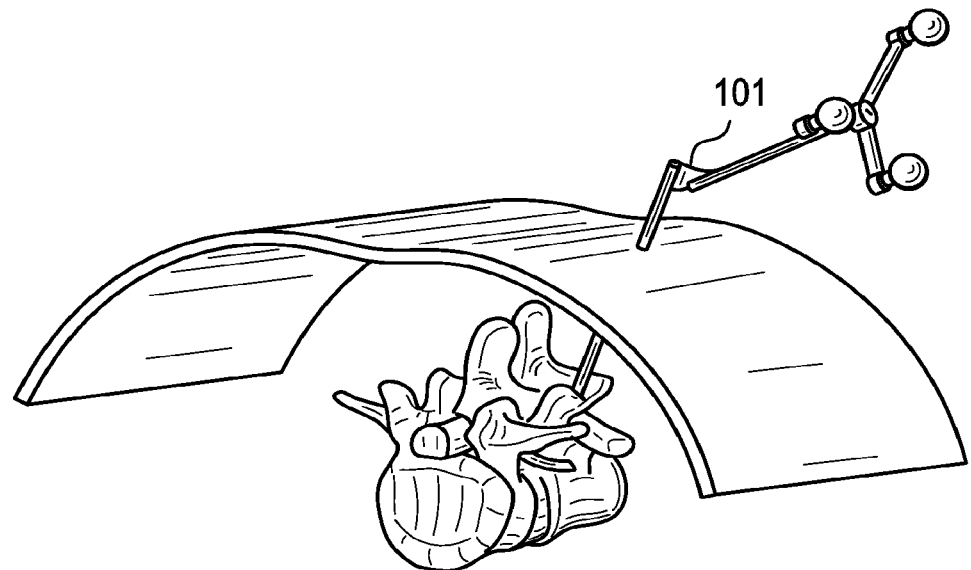
FIGS. 37-46 disclose a preferred method of surgery involving the access device.

In one embodiment, and now referring to FIG. 37, the surgeon places a pedicle screw-based anchor, adds a navigation reference frame 101 to the anchor, and uses a commercial navigation system for navigation. In some embodiments, a navigation array is placed onto the anatomy with reference to an anatomical feature that is symmetrically substantially adjacent the treatment site (e.g. contralateral cranial or caudal pedicle).

In some embodiments, there is navigation of the probe to a facet capsule or disc space through Kambin's triangle. Preferably, subsequent to fascia and muscle dissection, a probe enabled with navigation visualization is introduced to achieve an initial anchoring point. In one embodiment, the probe is inserted into the disc space by being indexed off the lateral border of the superior articulating process and may be optionally enabled with/supported by a nerve detection and/or visualization function. In another embodiment, the probe is introduced into the facet capsule.

In some embodiments, there is dilation over a navigated probe. Subsequent to the initial anchoring point, dilation is performed to prepare the surgical site for the size of port required to perform the treatment. Sequential dilation up to the preferred size port window is then performed. The port is then introduced over the associated dilator. In one embodiment, the initial anchoring is in the disc space and concentric sequential dilation device(s) would be used in order to retract tissue concentrically around the initial anchoring point (exposing the lateral portion of the SAP on the lateral aspect and Kambin's triangle on the medial aspect). In another embodiment, the initial anchoring is in the facet capsule and eccentric sequential dilation device(s) could be used to focus tissue retraction laterally over the lateral portion of the SAP and Kambin's triangle.

In some embodiments, the outer shield is stabilized onto an anatomical reference. The outer sleeve has a substantially tubular portion having a point or feature designed for attachment to a stabilization mechanism, which in turn is fixed to an anatomical feature on the vertebral body either cranial or caudal to the treatment site.

Figure 38:
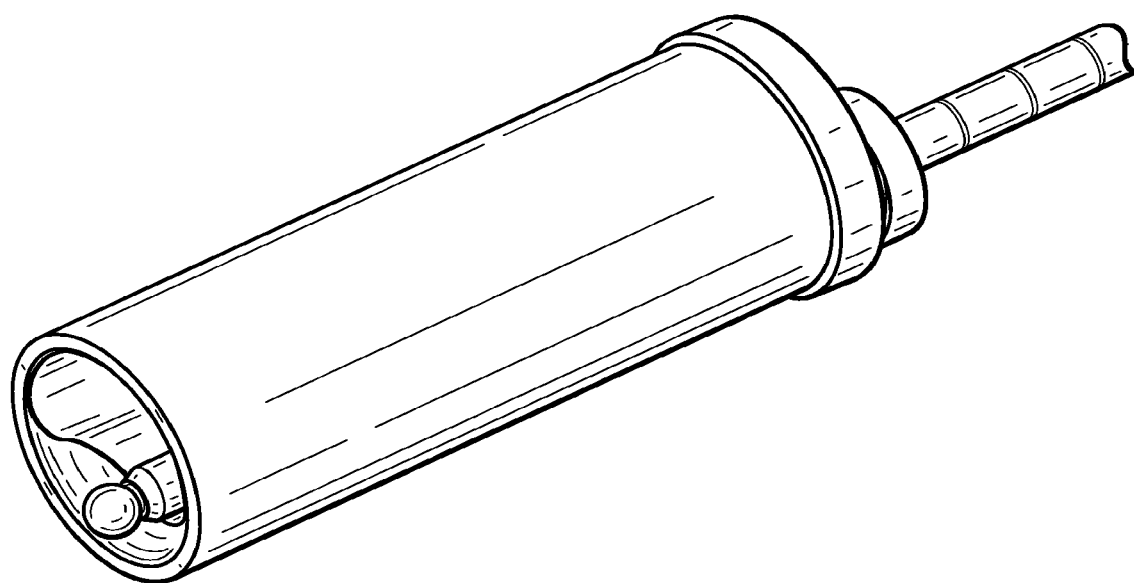

FIG. 38 discloses an outer tube into which a plug containing a template for guiding a bone cutting device.

In some embodiments, the outer sleeve is attached to a stabilization mechanism. In one embodiment, this stabilization device would be a device of sufficient length to reach an anatomical fixation point (e.g. pedicle screw) on the contralateral side of the treatment site. The mechanism (including its connection feature connecting to both the outer shield and the anatomical anchor) allows for sufficient flexibility of placement of the outer shield and sufficient stabilization to hold the outer shield in place until it is released by the user. The method of stabilization would be such that the user can dictate the degree of stiffness.

In another embodiment, this device has sufficient length to reach an anatomical fixation point (e.g. pedicle screw) on the ipsilateral side of the treatment site. Likewise, the mechanism (including its connection feature to both outer shield and anatomical anchor) would allow for sufficient flexibility of placement of the outer shield and sufficient stabilization to hold the outer shield in place until released by the user. The method of stabilization would be such that the user can dictate the degree of stiffness.

In another embodiment, this device would be a device of sufficient length to reach an anatomical fixation point (e.g. pedicle screw) on midline of the patient. Likewise, the mechanism (including its connection feature to both outer shield and anatomical anchor) would allow for sufficient flexibility of placement of the outer shield and sufficient stabilization to hold the outer shield in place unless released by the user. The method of stabilization would be such that the user can dictate the degree of stiffness.

Figure 39A:
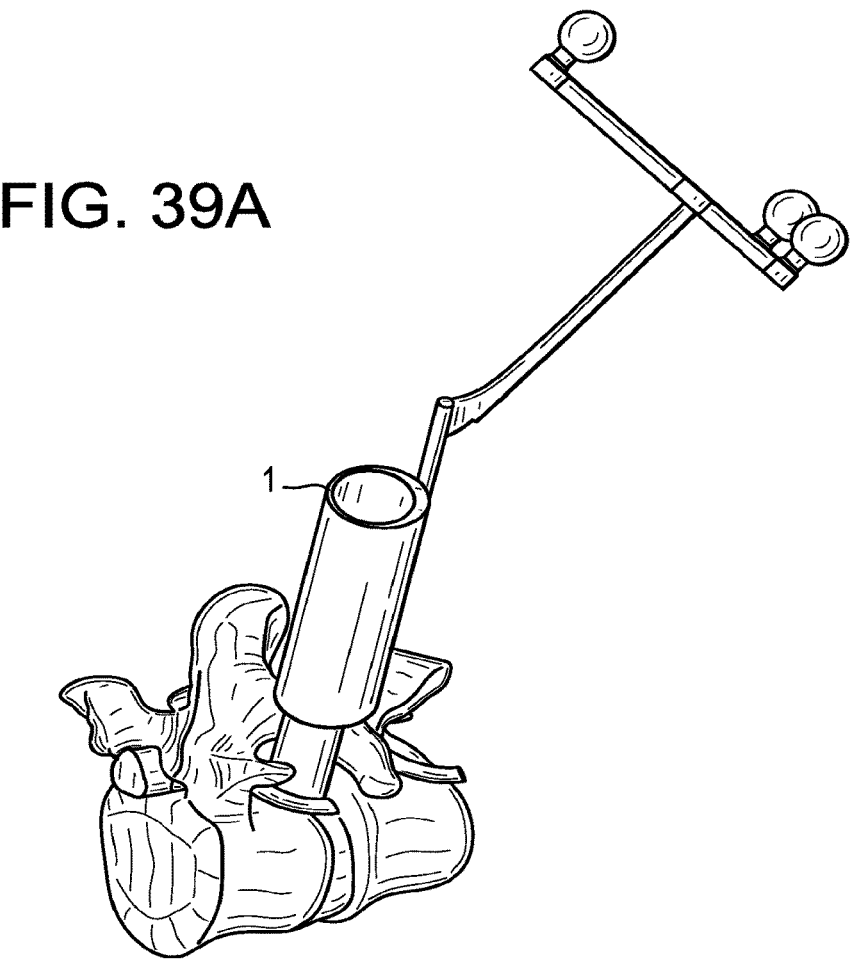
Figure 39B:
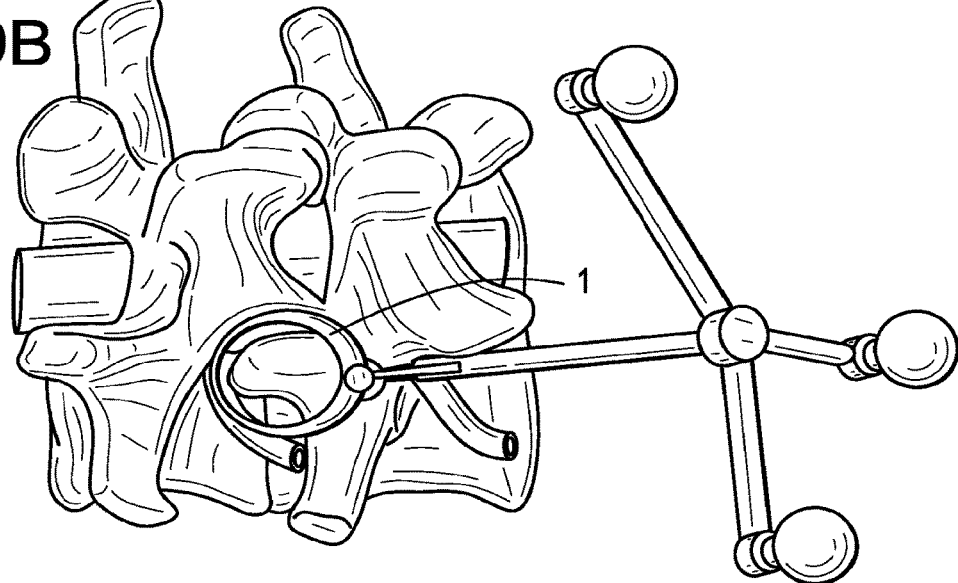

Now referring to FIGS. 39a-39b, the surgeon then dilates the tissue superior to the pedicle-based anchor, and inserts an outer shield 1, connected to the anchor, with its proximal end directed to the superior articular process. Blunt dissection up to the bone is carried out over the affected intervertebral disc, and muscle retraction over the affected intervertebral disc is then carried out. This retraction involves blunt dissection of the muscle and fascia to bone level under direct visualization.

Figure 40:
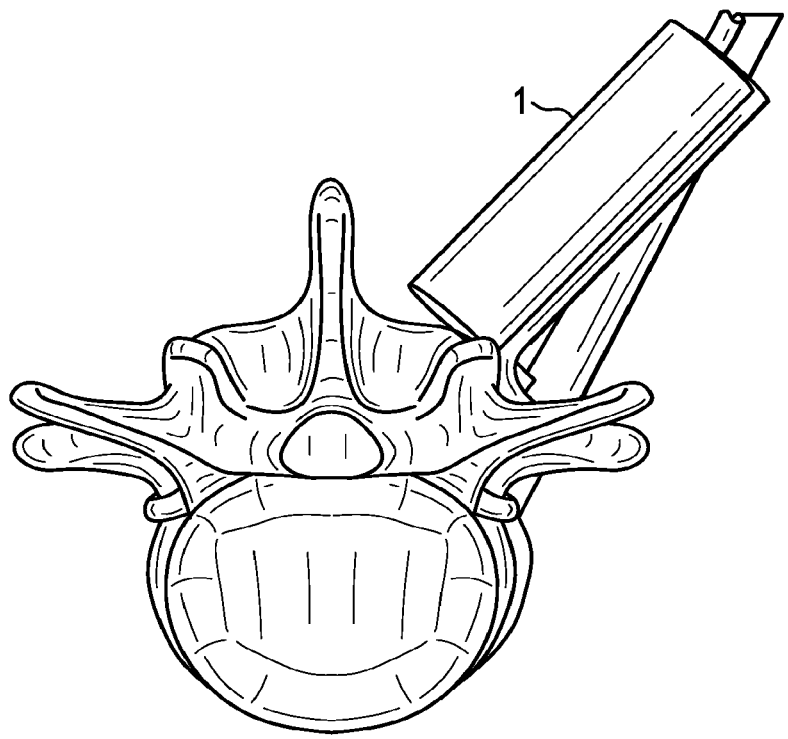

Now referring to FIG. 40, the surgeon then turns the outer shield 1 to the interlaminar space, preforms a central, bilateral decompression as required by the pathology, and then turns the shield back to its original position.

In some embodiments, an alternative to angling the access channel medially from the incision site could be the use of an alternative access site that would be more medial. In some embodiments, the initial anchoring point in the disc space will be medial to the inferior articulating process. For the embodiment having an initial anchoring point in the facet capsule, the dilation of the eccentric dilators will be medial from the capsule. Also, portions of the lamina and the inferior articulating process will be removed through the bone removal segment.

Figure 41:
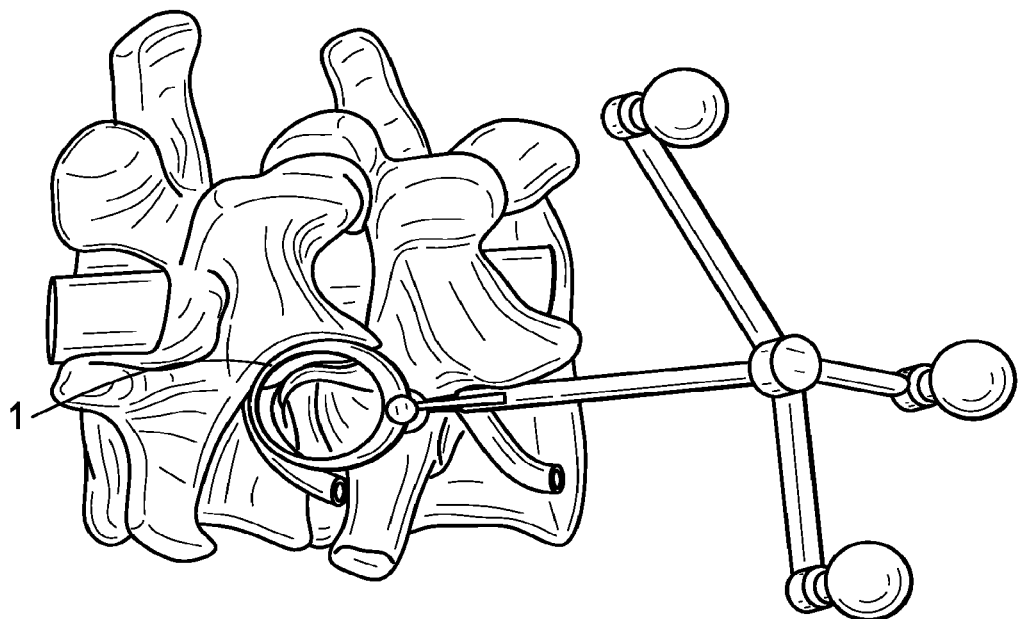

Now referring to FIG. 41, the surgeon then inserts a bone removal tool (not shown) into the outer shield tube and resects the lateral portion of the superior articular process to medially extend the traditional Kambin's triangle.

Under either direct or endoscopic visualization, a bone removal device is introduced to the outer shield and utilized to remove at least the lateral portion of the SAP. Such a device is available in lengths and sizes allowing for its safe introduction and use through an access window from 40 mm to 200 mm and a window size from 10mm-25 mm.

In one embodiment, this bone removal device is an ultrasonic cutting device. In another embodiment, this bone removal device is a reciprocating cutting surface. In yet another embodiment, this bone removal device is a revolving cutting tool. In another embodiment, this bone removal device is a mechanical punch with a stroke length between 10mm-30 mm. Removal of the bone can be performed in such a manner that sizes smaller than the access size will be excised and removed. The bone removal can be performed with the use of a template independently inserted into the outer shield and used to guide the direction of bone cutting and removal.

A Negative Template is a plug-like device that is inserted in the outer Access Tube. It contains a longitudinal cut-out in different shapes, depending on the cross-sectional shape of the tissue that needs to be removed respective of the cross-sectional shape of the tissue that needs to be covered and therefore protected from any surgical interactions. By inserting a cutting device like, e.g., a Milling Bit, into the longitudinal cut-out the surgeon is able to remove the tissue without the risk of endangering the covered tissue/structures. In combination with a proximal stop-system (on proximal end of outer Access Tube and/or shaft of milling system), the surgeon can remove the tissue layer by layer. The layer thickness and therefore the progression of the cutting procedure can be controlled via the stop system supported by a scale. This system allows the surgeon to perform safe tissue removal with a controlled serial work flow: check anatomical situation→adjust stop system to define cross-sectional thickness of tissue that needs to be removed→insert milling system until the stop system is engaged→mill/cut tissue (also blindly) in plane (2D)→remove milling system→check anatomical situation→adjust stop system.

A serial workflow can be considered to be safer than a parallel workflow, since the surgeon only needs to take care of one parameter at a time (here: planar position of milling bit followed by its depth followed by planar position of milling bit . . . ) whereas a parallel workflow requires the control of two or more parameters at a time (here: planar position of milling bit in parallel to its depth).

Navigation of SAP Removal can be carried out with the aforementioned bone removal device adapted to be navigated through its mechanical or visual connection with a navigation system.

Figure 42:
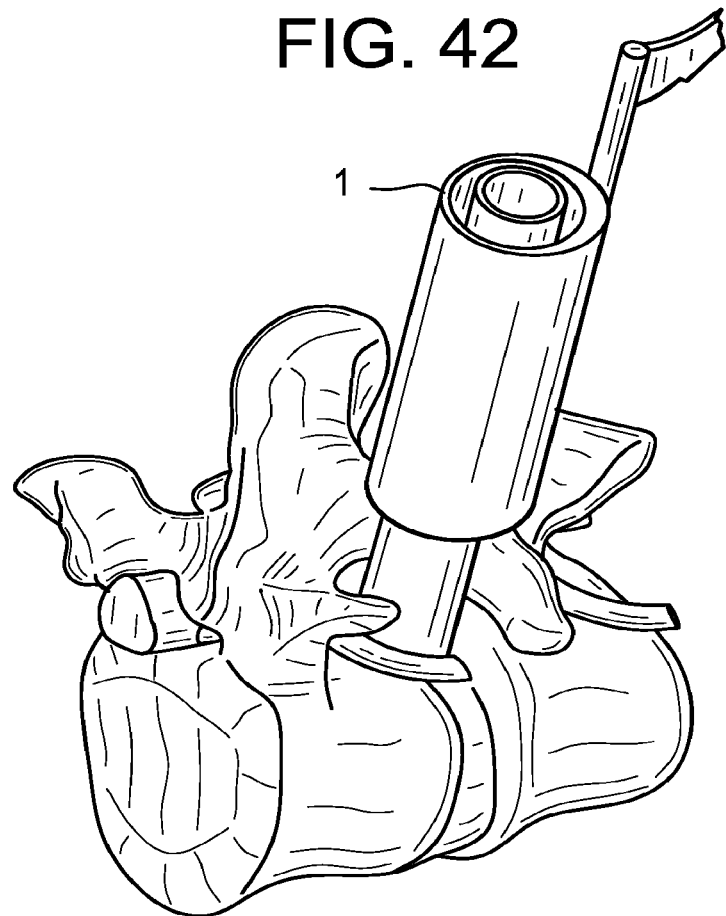
Figure 43:
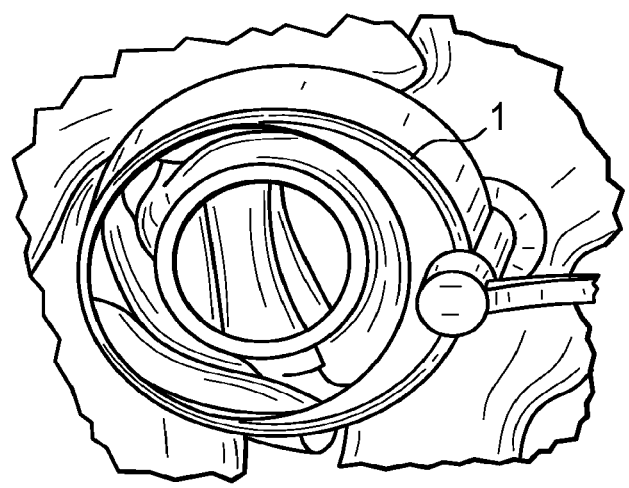

Now referring to FIGS. 42-43, the surgeon then inserts the inner shield tube into the outer shield tube, which acts to extend the outer tube anteriorly from the facet line until the tip of the inner shield reaches the level of the disc. The nerve root is protected by the inner shield.

Figure 44:
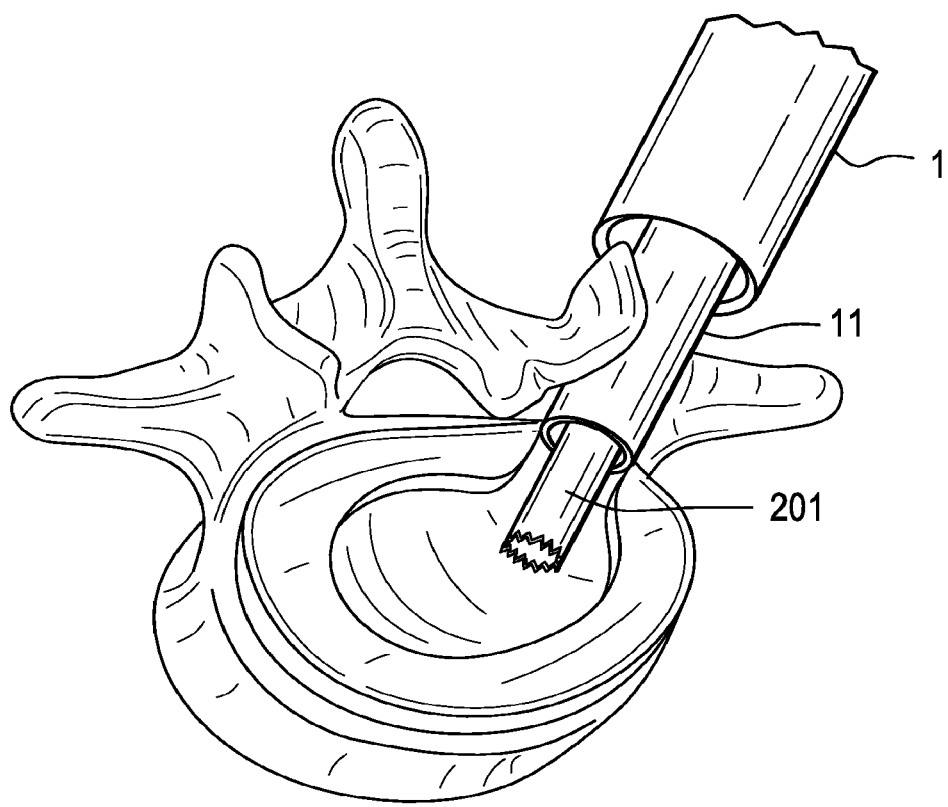

Now referring to FIG. 44, the surgeon then identifies the disc, spreads the disc with a wedged osteotome; checks the mobilization, and removes the posterior rim, osteophytes and annulus until a minimum annular window is opened. The surgeon then inserts a disc removal tool 201 into the access device, removes the disc and prepares the endplates.

An alternative embodiment to the prescribed disc clearing step in FIG. 44, would be to have the disc removal tool navigated through its mechanical or visual connection with a navigation system.

Figure 45:
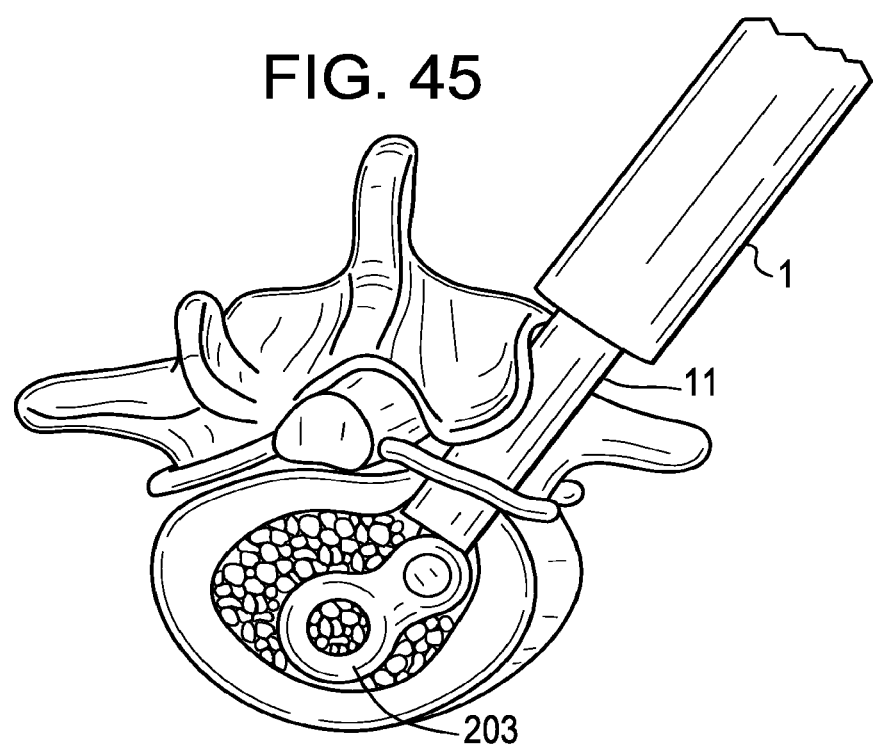

Now referring to FIG. 45, the surgeon then performs temporary disc space distraction, fills parts of the disc space with bone graft and inserts a fusion cage 203 into the remaining disc space.

Figure 46:

Now referring to FIG. 46, the surgeon then adds posterior fixation 103.

Viewing Element

In some embodiments, a visualization element based on the chip-on-tip technology and integrated into the wall of the port is used. This embodiment has a number of advantages over a standard rod-lens endoscope that is mounted at the tube wall:

Manufacturing costs. The chip-on-tip technology allows a very cost efficient manufacturing, therefore can be marketed as a 'single use' instrument.

Rigid portion only at distal tip. Whereas a standard rod-lens endoscope system has a stiff, cylindrical shape throughout the whole tube, the chip-on-top endoscope may have a non-cylindric configuration at the proximal outer tube end. Preferably, this shape is a flat cable shape. In some novel embodiments, in relation to a standard rod-lens-endoscope, the chip-on-tip endoscope has a relatively short "stiff" section (about 20 mm), where the proximal portion consists of a cable that can be flexible. In other embodiments, the stiff portion is shorter (producing a smaller chip-assembly) and actively articulating concepts are used to change the lens angle. Due to the cable's integration in the tube wall, the shape of the port window is maintained throughout the procedure. For example, a 5 mm chip on tip endoscope turns a 15 mm circular access window into a kidney shaped access window.

Size/weight of camera unit. A standard rod-lens endoscope has a standard eyepiece that is a universal interface with a certain size. The camera that is connected to such a system has to be built in a certain dimension to be compatible with the eyepiece. This requirement produces a relatively bulky camera attachment (approx. 3cm-6 cm in diameter, approx. 5cm-10 cm in length) having a number of drawbacks. First, this large camera construct can be a physical obstacle to work, especially if the trajectory of the working port changes or interferes with the camera. Secondly, the dimension and weight of this conventional construct becomes significant enough to produce certain undesirable forces upon the rod-lens-endoscope, especially in bending. Thirdly, the relatively fragile conventional rod-lens-endoscope has to be embedded in stabilizing structures such as metal tubes, thereby further reducing the active working window.

With the chip-on-tip embodiments disclosed herein having its chip cable embedded in the wall of the outer tube, the cable that exits at the proximal outer tube wall does not produce similar forces upon the working port. Also, respecting the attachment mechanisms that mount the chip-on-tip endoscope in the tube-wall, the lack of bending forces produced thereby raise the possibility of adopting relatively thin attachment options that mechanically do not need to be very stable.

Working Environment. Conventionally, a constant fluid environment (permanent flow of saline solution) is used in spine endoscopy applications. However, in a mini-open and microsurgical environment, the fluid environment is not helpful, as the anatomical conditions are very different. Accordingly, in the preferred novel procedures described herein, the chip-on-tip endoscope works in a dry, open air environment. However, the open, dry air environment in which the chip-on-tip endoscope is used may produce an undesired condensation effect upon the lens component of the endoscope. For example, a colder lens in a humid body temperature environment may fog up. Moreover, drill debris, burr debris or smoke from monopolar scalpels or hemostatic tools can likewise affect the lens of the endoscope so as to reduce visibility. Accordingly, it may be desirable to periodically clean the lens of the chip-on-tip endoscope.

Nerve Deflection (Tube in Tube)

In minimally invasive spine surgery conducted through portals, a set of dilators is often used to prepare the site for reception of the portal. One such technology is shown in US Patent Publication US 2012-0232552 (Morgenstern). In this conventional technology (which has eccentric dilators), the outer diameter of any one of the dilators is identical to the inner diameter of the next successive (outer) dilator. This identity of diameters is necessary for fluoroscopy assisted, percutaneous muscle dilation.

Since some embodiments of the present application describe a procedure between the level of the facet joint and the disc, the surgical site is dissected under direct visualization. Accordingly, the diameters of successive dilators used in these novel procedures do not have to match. Relaxation of the "exact diameter" requirement in these novel procedures allows the surgeon freedom in many tube design areas. For example, it allows the use of tubes that are tapered. It also allows the surgeon the freedom to use outer and inner ports that are not coaxial. It further allows the trajectories of the inner port relative to the outer port to vary in angulation within certain treatment steps. Lastly, it allows the trajectories of the inner port relative to the outer port to vary in distance within certain treatment steps.

Because fluoroscopy-assisted, percutaneous muscle dilation is carried out without direct visualization, it is a blind procedure whose use has limitations. These limitations include the inability to carry out surgical steps that require direct visualization out of safety considerations. One such treatment step requiring direct visualization is direct decompression of bony and ligamentous tissue that is directly adjacent to nerve structures.

Because some embodiments described herein allow for direct visualization of delicate anatomical structures, those embodiments further specifically allow direct decompression of bony and ligamentous tissue that is directly adjacent to nerve structures and more generally allow manipulation or removal of tissue adjacent the tubes through a very tissue-preserving "tube-in-tube" access port.

Morgenstern further describes a method in which a guide wire is directly introduced through the disc space to Kambin's triangle, under fluoroscopy guidance (i.e., no direct visualization). Morgenstern further describes the possibility of using electrically-based nerve monitoring probes. Moreover Morgenstern describes a method of enlarging the spinous process by subsequently rasping away bone from the SAP and the pedicle.

The novel procedures described herein only perform non-visualized procedures (e.g., dilation) in a safe zone above the facet line. In the anatomically more critical zone between the level of the facet joint and the disc, the novel procedures dissect the surgical site under direct visualization, thereby allowing the surgeon to spare as much of the bone as is possible and as is meaningful.

Navigation

Navigation enhances static x-ray, CT, or MRI data by intra-operatively showing in real-time where the instruments used actually are in relation to the anatomy of the patient. Therefore it increases the safety of those instruments by showing their shape, trajectory, and positioning and even more importantly it supports the surgeon to keep instrument orientation during the performed manipulations.

Without wishing to be tied to a theory, it is believed that one reason why minimally invasive techniques are not often used is the significantly higher x-ray exposure needed to keep orientation in comparison to mini-open techniques, where the surgeon still has direct visualization and so can actually see the active site with a microscope or loupe. The x-ray exposure is an even greater for the surgeon who is exposed to the radiation on a frequent basis. This challenge is addressed by the implementation of navigation technology in the novel procedures described herein because they allow the reduction of x-ray exposure to an ideal minimal total of two x-rays for registration purposes. Once a single lateral shot and a single anterior—posterior shot have been registered, all used instruments (e.g., Jamshidi-Needle, Pointer, Dilataors, Access Tube, Osteotome, Expandable Cage itself, Disc Removal Device . . . ) can be projected in these static fluoro-images in real time. Another positive effect is a significant savings of time. Having the navigation system in place also helps the surgeon to understand the orientation (trajectory and depth) of the endoscope and therefore to understand what he or she actually sees with the camera. This can either be achieved by navigating the camera directly or indirectly by setting the camera in a fixed position integrated into a navigated Access Tube.

The Jamshidi-Needle, Pointer, Dilators, and Access Tube Instruments can all be navigated with only one Instrument, the FOX-Navigation-Multi-Tool or "multi-tool." The multi-tool can include integrated or built-in neuromonitoring, e.g., for detecting the presence, proximity, health, or other attributes of nerve tissue. The multi-tool can include an electrode, transducer, or other energy delivery element for applying energy to tissue, e.g., to ablate or cauterize the tissue. The multi-tool can include an energy delivery element in the form of a microwave ablation element. The multi-tool can include an energy delivery element of the type used in the NEUWAVE system available from ETHICON, INC. of Cincinnati, Ohio. The energy delivery element can be built-into the multi-tool, or can be supported or guided to a target location using the multi-tool. The energy delivery element can be mounted on a shaft or needle coaxially received within or around another shaft component of the multi-tool. The multi-tool can be used to position the energy delivery element in proximity to a target location, such as an osseous bone tumor. Energy can be delivered from the energy delivery element to the tumor or other target location.

Figure 47A:
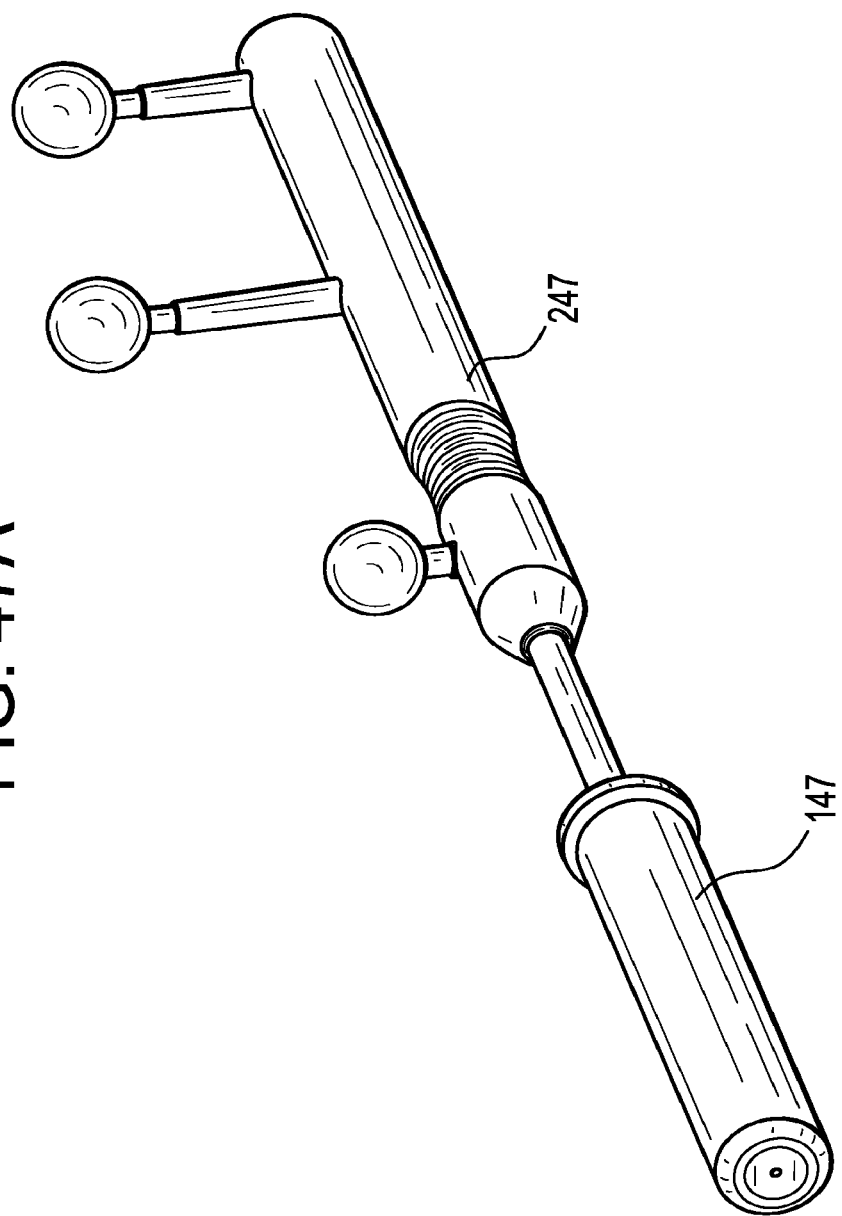
FIGS. 47a-47c disclose a Navigation plug comprising a base having an array attached thereto, wherein the plug is adapted to fit within an outer tube.
Figure 47B:
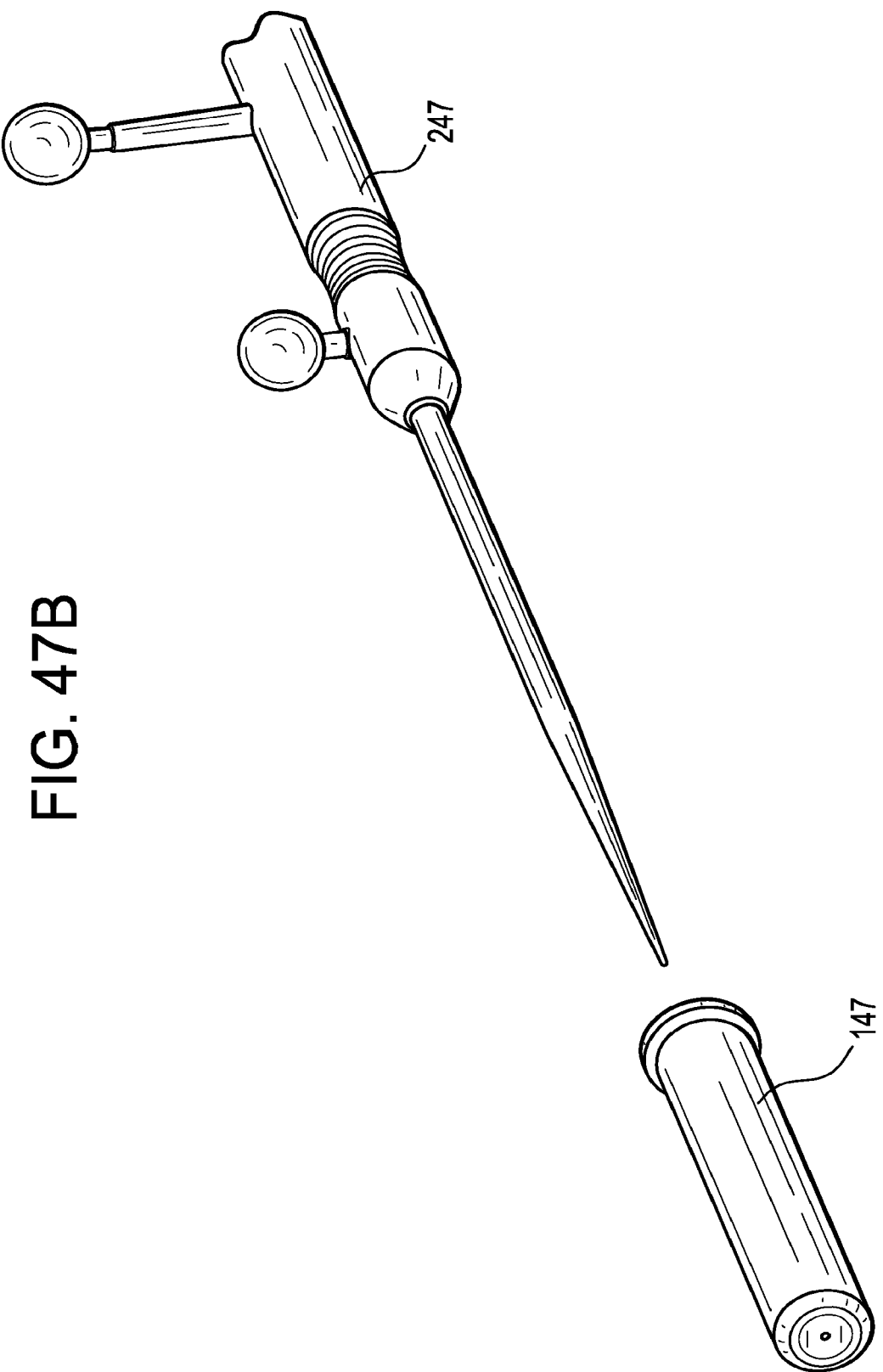
Figure 47C:
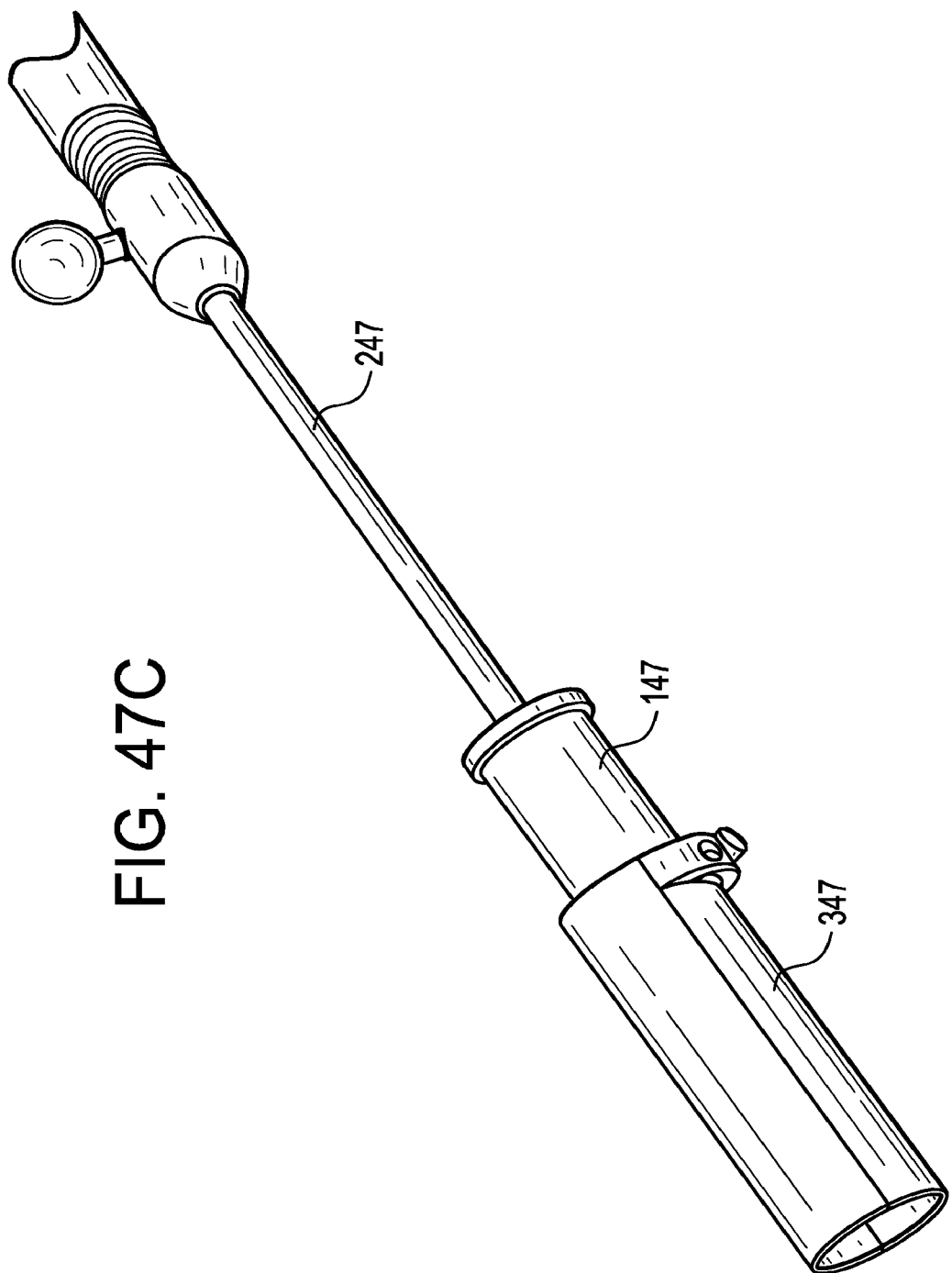

FIGS. 47*a*-47*c* disclose a Navigation plug comprising a base 147 having an array 247 attached thereto, wherein the plug is adapted to fit within an outer tube 347.

Bone Cutter

In some embodiments, the novel procedures use an Ultrasonic Bone Cutting device for SAP removal, which specifically cuts bone only and will not cut soft tissue. Embodiments based on a conventional Expandable Cage Device for interbody fusion may require an access window at least as large as 12 mm. Such a large window can only be achieved by (partly) removing the Superior Articulation Process (SAP) to extend the Kambin's Triangle. The Ultrasonic Bone Cutting Device adds significantly to the safety of this procedure since it does not cut nerves if accidently hit. If the cutting device blade is designed to be in the shape and diameter of the Inner Tube/Blade (i.e., a Cookie Cutter design) that approaches distally down to the level of the disc space, the SAP removal can be minimized (less trauma, less stress for patient, quicker recovery) and performed in a single step (faster than multiple step procedure).

Figure 48:
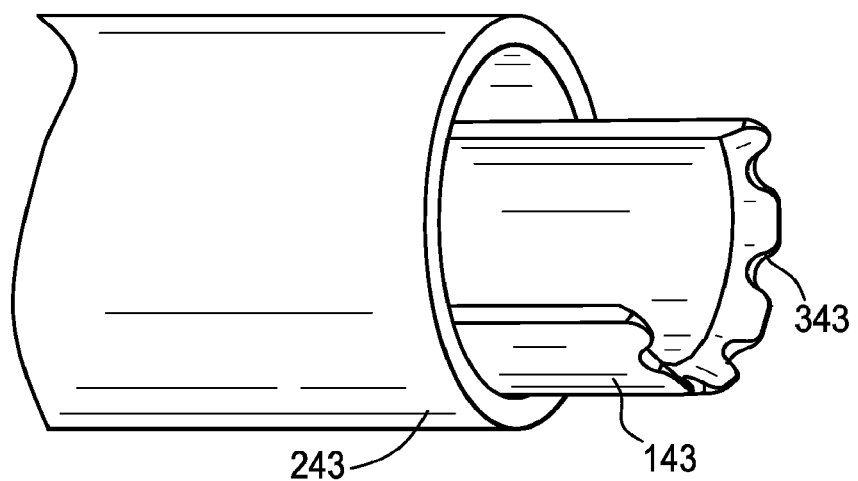
FIG. 48 discloses the cookie cutter-type distal end of an ultrasonic cutter extending from the end of an outer tube, wherein the distal end has a plurality of cutting teeth.

FIG. 48 discloses the cookie cutter-type distal end 143 of an ultrasonic cutter extending from the end of an outer tube 243, wherein the distal end 143 has a plurality of cutting teeth 343.

Another option to increase the safety of bone cutting is a depth-controlled manual milling of the bone with a negative guide. The negative guide covers those areas that will not be removed (negative template). The depth control allows the milling of the bone layer by level, under serial control of the surgeon. The reference for the depth control as well as the trajectory can be the outer Access Tube (also see paragraph navigation).

Figure 49A:
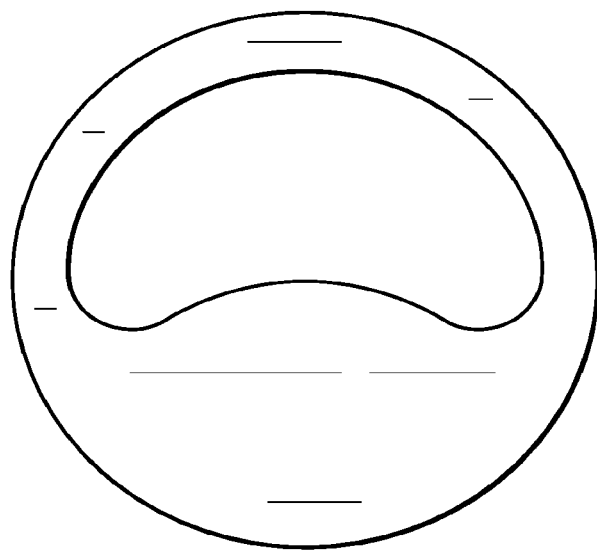
FIGS. 49a-49b disclose various cross-sections of the template for guiding a bone cutting device.
Figure 49B:
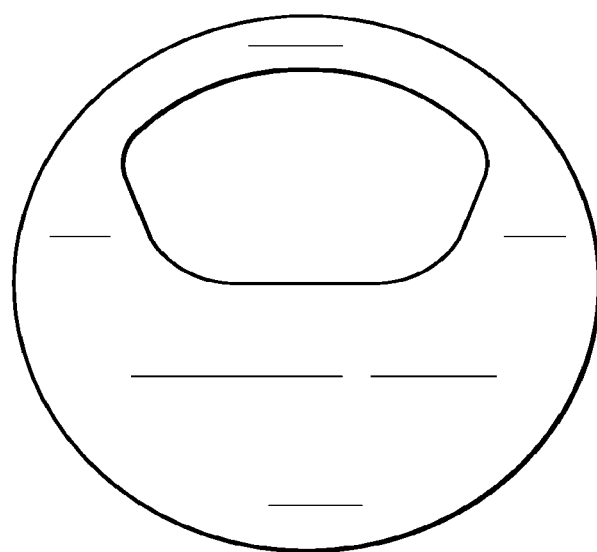

FIGS. 49*a*-49*b* disclose various cross-sections of the template for guiding a bone cutting device.

Bone Cutter

In some embodiments, the bone removal device is a harmonic scalpel having a cookie cutter design. The scalpel has a crescent—shaped cutting surface that interfaces with the outer tube. The scalpel is used as a single pass instrument, removing a predetermined amount of bone in a single pass. In some embodiments, the scalpel also has a tube that sprays water for irrigation, while the outer tube has a suction line for clearing the slurry of removed bone.

In some embodiments, the scalpel can be navigated and ride down a slot provided in the inside wall of the outer tube. The slot depth can be predetermined to provide depth-controlled milling, and to control where cutter goes. This is advantageous because it is believed that freehand cutting hits the nerves too easily. The shape and size of the cutting surface can define the specific area of bone to be removed. The specificity of cut is advantageous because it minimizes the amount of bone removal, which is beneficial in the highly enervated facet. Thus, a quicker procedure, less trauma (less pain), and more stable construct is realized.

Viewing Element (Olive)

In some embodiments, the chip viewing element can be angulated so it can see around a corner of the tube;

In a conventional endoscope, visualization is 2D (i.e., no depth perception) and so two nerves may look close together when they are actually 2 cm apart. Thus, in some embodiments, the endoscope is modified so that the chip acts like a range finder. In particular, the chip identifies and assesses a reference feature that is a known distance from chip, and then measures how far away a nerve is from chip (which is the tube end) based on that assessment.

Nerve Deflection (Tube in Tube)

In some embodiments, the outer shield has a pressure sensor thereon to measure the stress on the nerve. Using ultrasound techniques that can measure distance, the system can measure the elongation of nerve under retraction and define a maximum elongation limit (e.g., 20%), and then warn the surgeon if the elongation limit is exceeded. In some embodiments, the system integrates ultrasound into the port and thereby navigates the port.

In some embodiments, the surgeon navigates the camera. This allows the surgeon to understand orientation of the camera.

In some embodiments, visualization provides an axial view of the disc, so the surgeon can understand the location of the disc removal tool.

Neuromonitoring Analytics

Currently, neuromonitoring devices can be used to obtain an indication of potential nerve health or nerve damage, which may be induced in a surgical setting. This indication of nerve health is achieved by measuring electrical impulses between a nerve near a surgical site and a far end of the nerve. For example, impulses may be measured between a nerve root at the spine and some point found on the legs.

Nerve damage can be caused through direct manual contact with a nerve. Apart from gross damage such as severing or crushing the nerve, other lesser forces imparted on the nerve can also cause damage. For example, displacing the nerve, stretching it, or compressing it can cause significant damage. In some cases, extended application of such forces to the nerve can reduce blood flow through the nerve, again causing nerve damage. Often times, this exposure time is dependent on the amount of force applied. Accordingly, there appears to be no known steadfast rule as to how long the surgeon may be able to load a nerve.

Alternate forms of evaluating potential nerve damage besides neuromonitoring may bring new insights into nerve protection during a procedure. In this regard, nerve manipulation measurement could yield an indication of risk to the nerve. If a nerve is displaced for the procedure, it may be elongated or it may be displaced laterally. These alterations in the nerve's physical features could be measured and used to predict potential nerve damage. Accordingly, other potential features could be measured and used to predict potential nerve damage include arc length and the diameter of the nerve itself etc. These features may be measured in quantifiable terms via techniques such as ultrasound. The resulting measurements are and then analyzed (via software or manually) in terms of absolute value, percent change, or some other metric indicative of potential nerve risk/damage that can be obtained from a database or library. In some embodiments, these metrics can be used as predictors of the safe length of time that a nerve can have a given displacement or deformation without causing long term damage. Calculation or algorithms can also be used to determine a maximum safe deformation, or a maximum allowable time during which a nerve can have a given deformed feature.

This measurement could be obtained in many ways. It can be measured manually, optically or through some other form of imaging. This could occur in an open procedure, subcutaneously in an MIS or other type of procedure. Direct visualization could be completed with the use of a camera. Before and after images could be interpreted to calculate the amount of absolute deformation or percent change. The measurements can be obtained through modalities such as ultrasound, or other forms of imaging that can "see" soft tissue or identify nerve tissue relative to the surrounding tissue (X-ray, CAT/PET scan, MRI, etc.).

Other measurement methods that can be used in accordance with this embodiment may include a) measurement of density change within the nerve due to loading, or b) change in blood flow. Such measurements can be obtained through radar, ultrasound, and other imaging methods.

In some neuromonitoring embodiments, it may be possible to measure impedance within the nerve or impulses, wherein this may be done locally relative to the specific deformation area of the nerve. In particular, in some embodiments discussed herein, the nerve shield could have a sensor on opposite edges of the shield that would contact the same nerve in two different nerve locations. These sensors would allow the surgeon to read electrical values such as impulses or resistance, before nerve distention and then measure it again as distention occurs or is achieved. The difference in these measured values could be an indicator as to the level of deformation. Any of the neuromonitoring features described above or elsewhere herein can be incorporated into or included in the multi-tool. For example, the above-described sensors can be mounted to a shaft component of the multi-tool, which can be used to position the sensors in proximity to nerve tissue.

Figure 50:
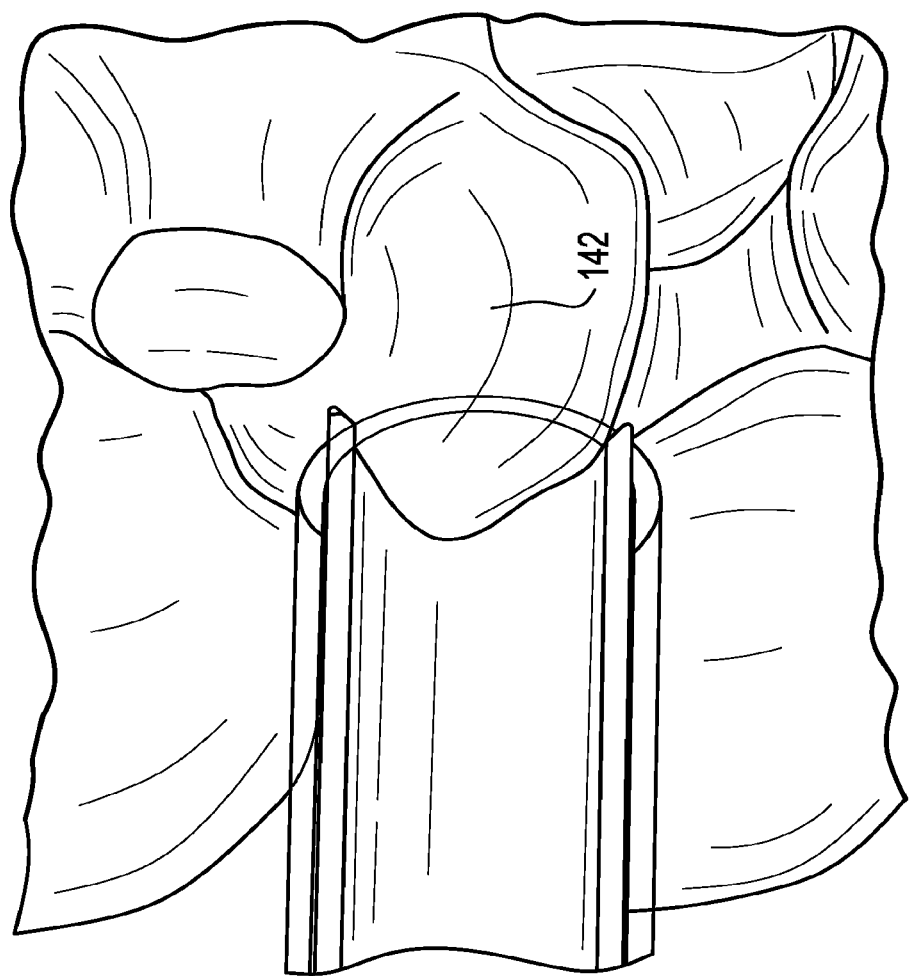
FIG. 50 discloses a cookie cutter-type distal end of an ultrasonic cutter having a semicircular cutting piece cutter bone.

FIG. 50 discloses a cookie cutter-type distal end 142 of an ultrasonic cutter having a semicircular cutting piece cutter bone.

Figure 51:
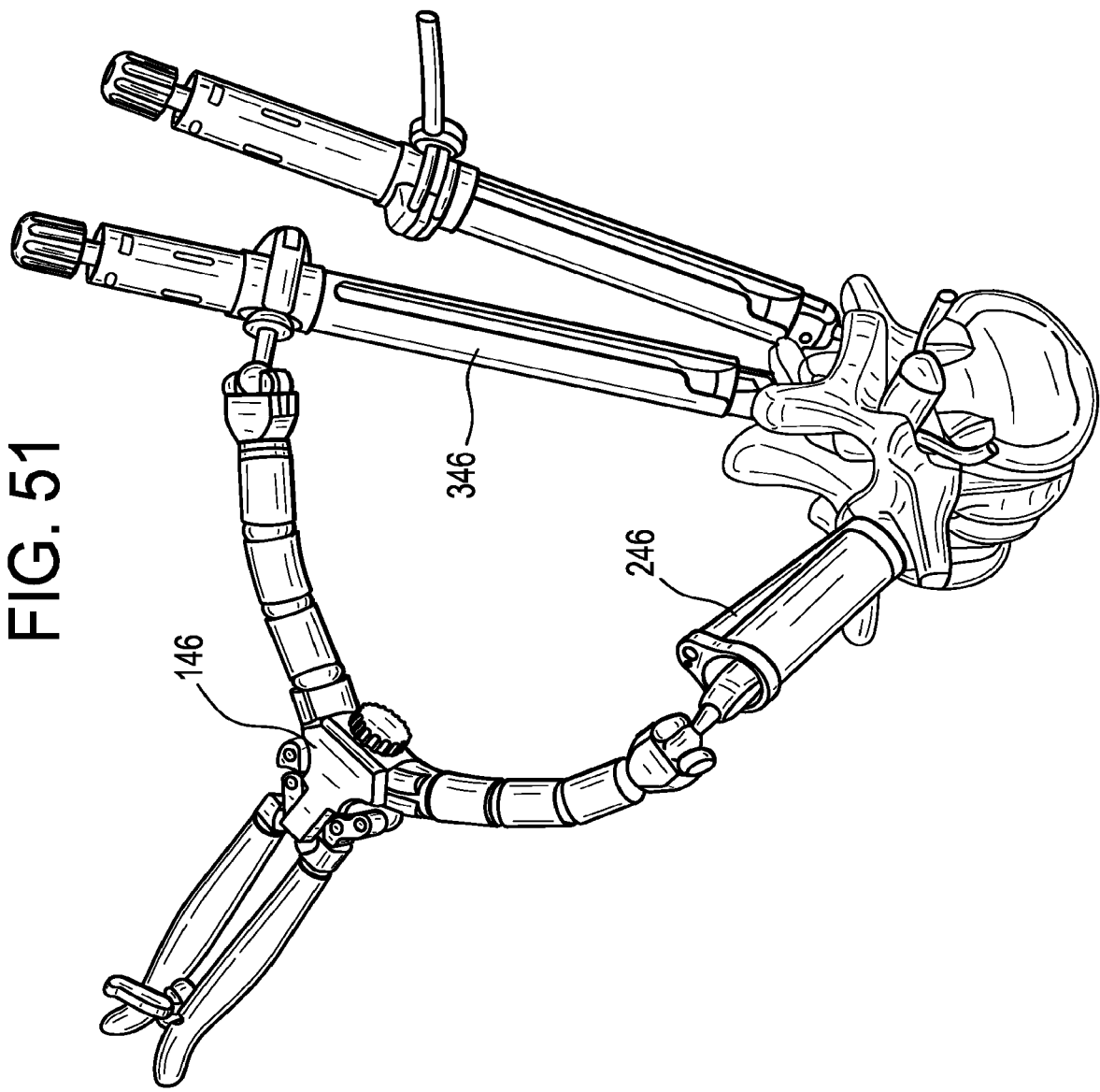
FIG. 51 discloses a mini flex arm connecting an outer tube and a screw extension.

FIG. 51 discloses a mini flex arm 146 connecting an outer tube 246 and a screw extension 346.

Figure 52:
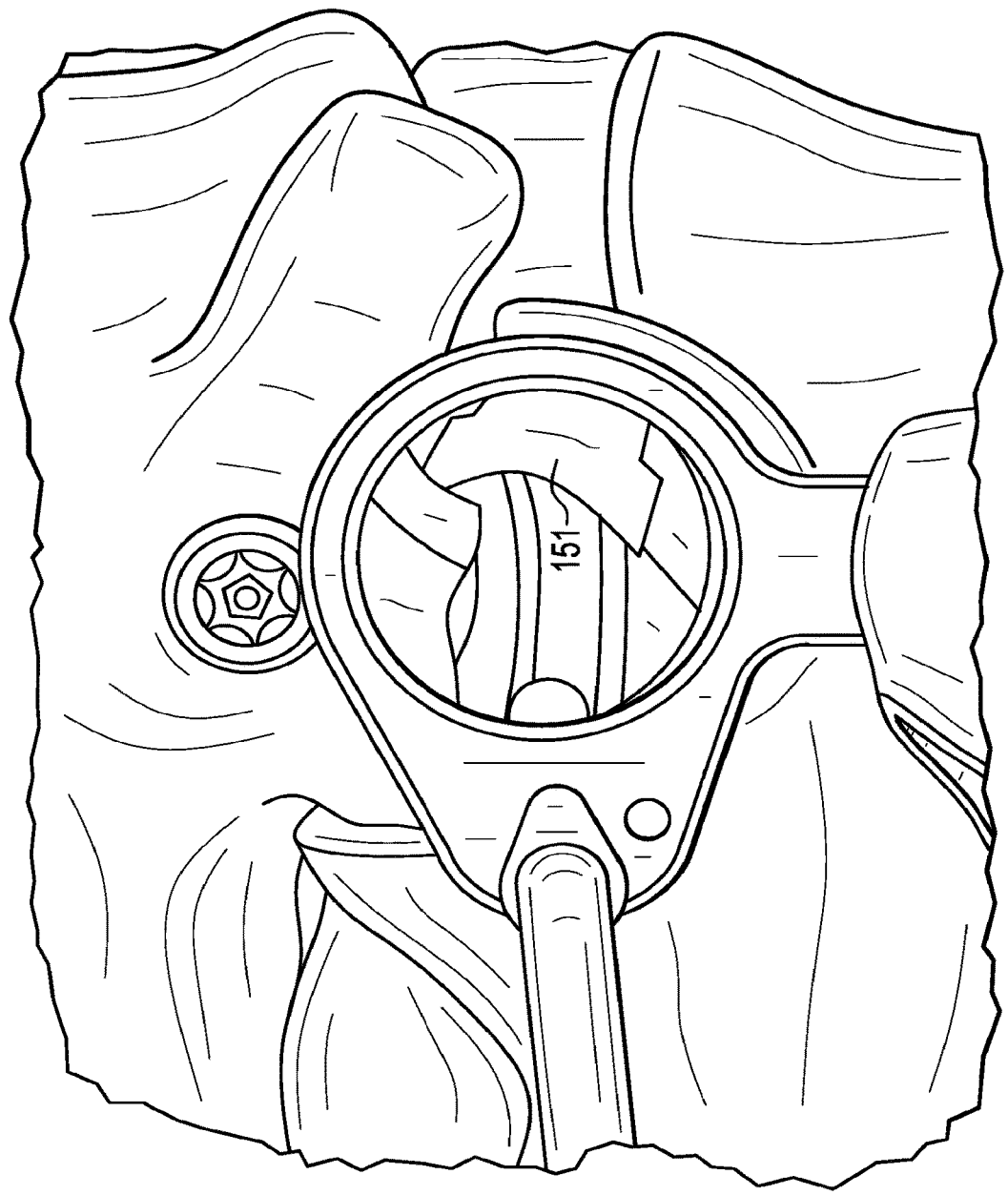
FIG. 52 discloses an outer tube/inner retractor assembly wherein the inner retractor is tilted inwards to retractor soft tissue.

FIG. 52 discloses an outer tube/inner retractor assembly wherein the inner retractor 151 is tilted inwards to retractor soft tissue.

Figure 53:
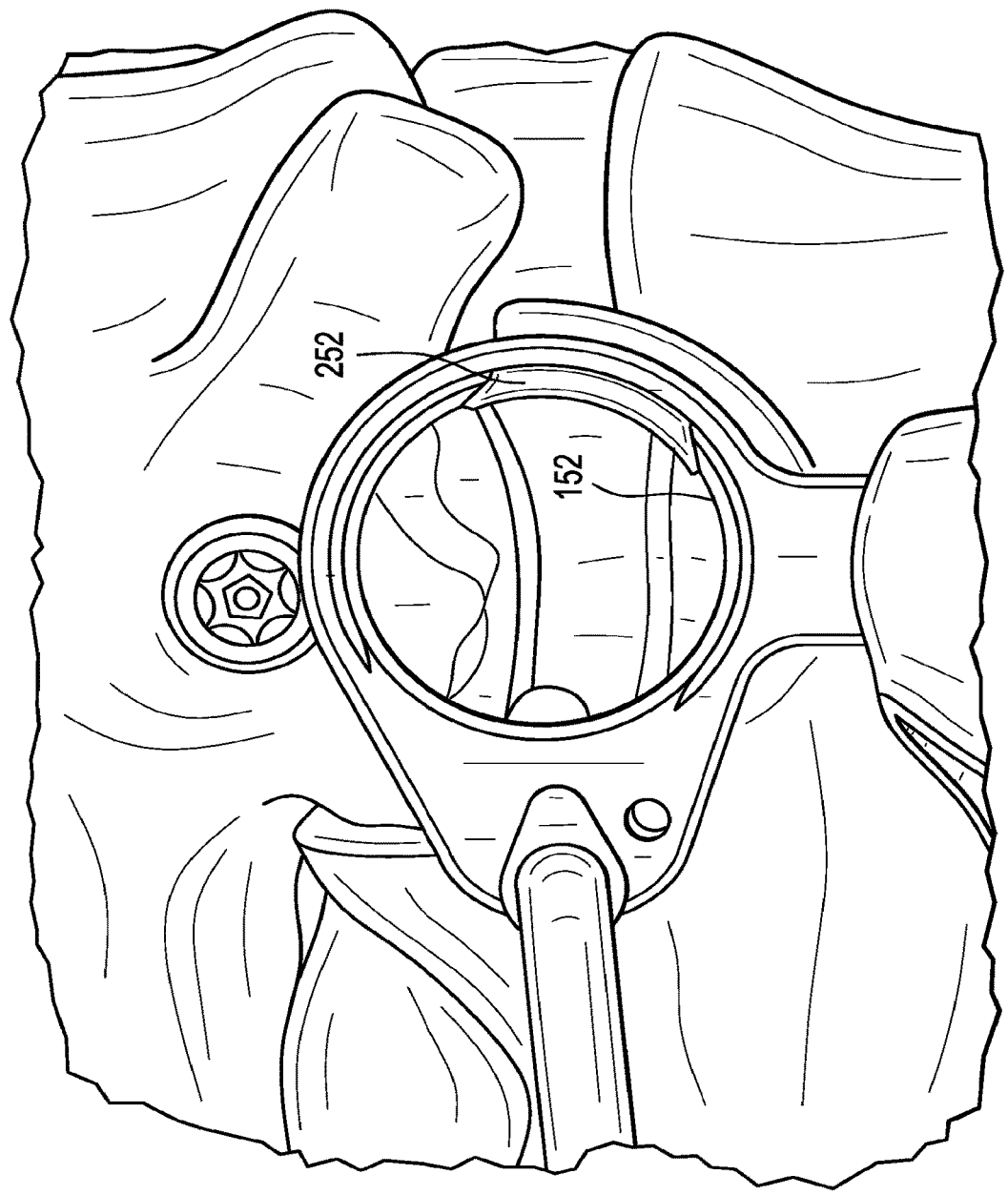
FIG. 53 discloses an outer tube/inner retractor assembly wherein the inner retractor runs parallel with the outer tube.

FIG. 53 discloses an outer tube/inner retractor assembly wherein the inner retractor 152 runs parallel with the outer tube 252.

Figure 54:
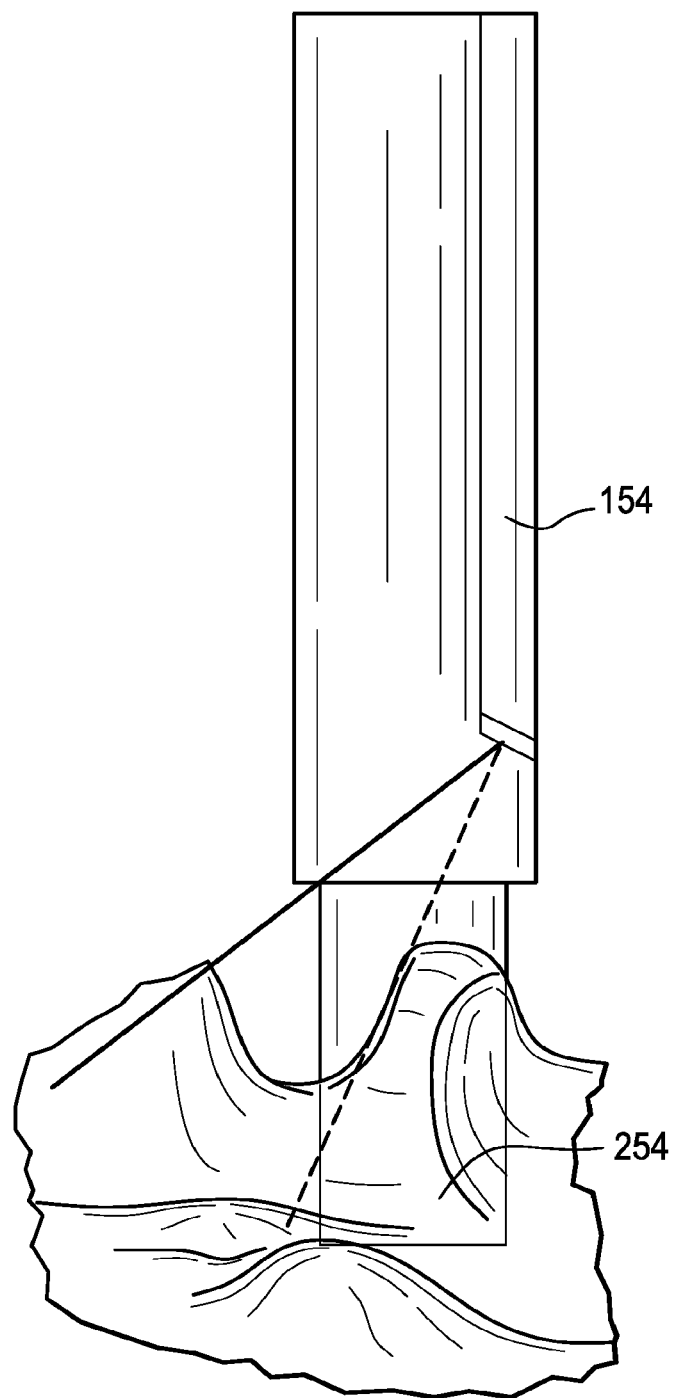
FIG. 54 discloses an endoscope housed within an outer tube, and an inner tube extending from the outer tube.

FIG. 54 discloses an endoscope 154 housed within an outer tube, and an inner tube 254 extending from the outer tube.

In many embodiments disclosed above, an inner shield nests within an outer shield. In an alternative embodiment to all such embodiments, however, the inner shield is replaced with a removable blade that is integrated into a cutout formed within the wall of the outer shield. In such cases, the outer surface of the inner shield substantially nests within the outer surface of the outer shield so that the flange extends distally past the distal end portion of the outer shield.

In many embodiments disclosed above, the proximal end portion of the substantially tubular portion of the inner shield comprises a stop adapted to abut the proximal end portion of the outer shield, the stop being adapted to prevent excessive distal movement of the inner shield. In other embodiments, the abutment occurs anywhere along the outer shield.

FIGS. 55-63 disclose some of the instruments used in preferred procedures disclosed herein.

Pedicle Post w/ Reference Array

Figure 55:
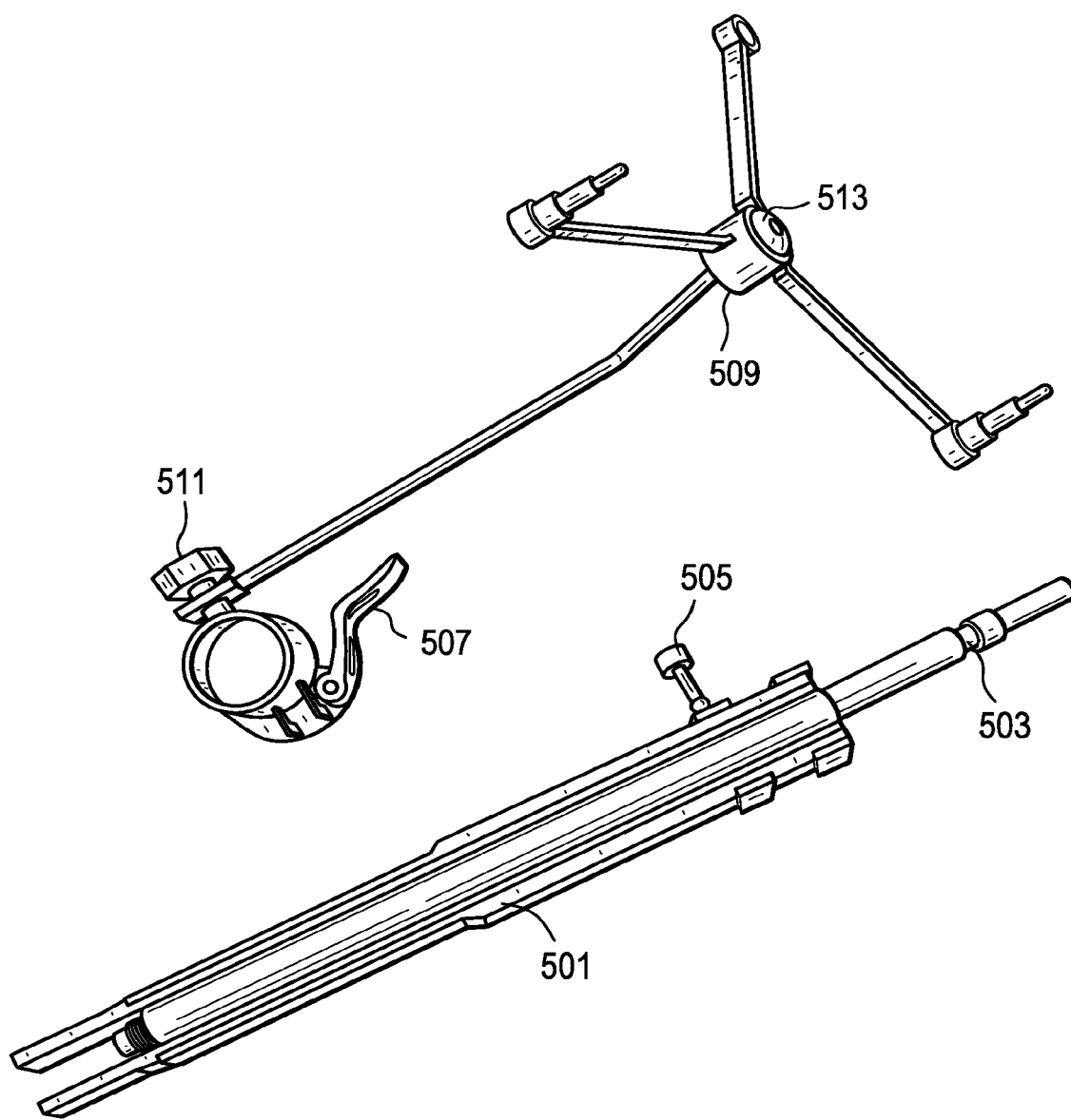
FIGS. 55-63 disclose some of the instruments used in preferred procedures disclosed herein.

Now referring to FIG. 55, a first step of a navigated procedure is the placement of a Pedicle Screw (such as Viper 2 or Viper Prime, available from DePuy Synthes Spine, Raynham, Mass.) in the contralateral caudal vertebral body followed by the insertion of a center core 501 including a polyaxial blocking post 503, which engages with the thread for a locking cap of the Pedicle Screw. When tightened, the polyaxiality of the screw is fully blocked. A screw 505 locks the Center Core with the Polyaxial Blocking Post. A clamp 507 with an eccentric lever securely connects the Reference Array 509 on the Pedicle Post. Two additional screw connections 511, 513 allow the surgeon to align the Reference Array set up with the cameras to the navigation system, which are most commonly places at the caudal side of the patient.

The Reference Array should directly be mounted on Blocking Core (see Pedicle Anchor). In some embodiments, there is an adjustable orientation of the array on the post. In some embodiments, care is taken to make sure that the distance between the handle and the top of the counter-torque insert is greater than the length of the screws. In some embodiments, the navigation array is strong enough to act as counter-torque for polyaxial blocking (which would be done before registration).

Multi-Tool

Figure 56:
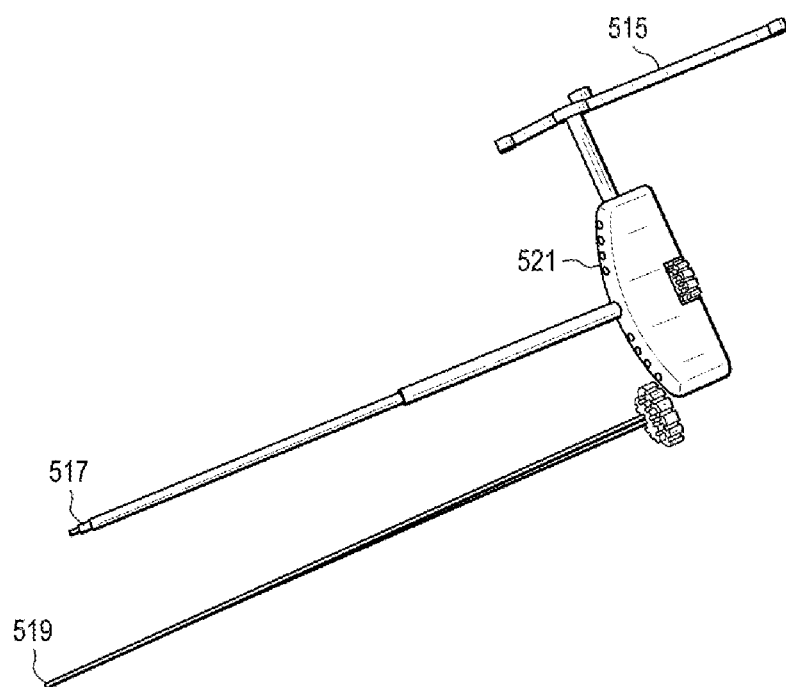

Now referring to FIG. 56, there is a provided a Multi-Tool probe comprising a main body 515 including a Navigation Array (single piece), a Blunt Mandrin 517, a Sharp Mandrin 519, and a Detachable Handle 521. This set of features allows the surgeon to use the device as a Navigation Pointer (with Blunt Mandrin), a navigated Jamshidi-Needle (Sharp Tip), and a device to navigate the insertion of Dilation Tubes as well as the Access Tube (see below). This tool uses a single array and the resulting single registration procedure covers four functions. In some embodiments, the array is part of a detachable handle.

Figure 56A:
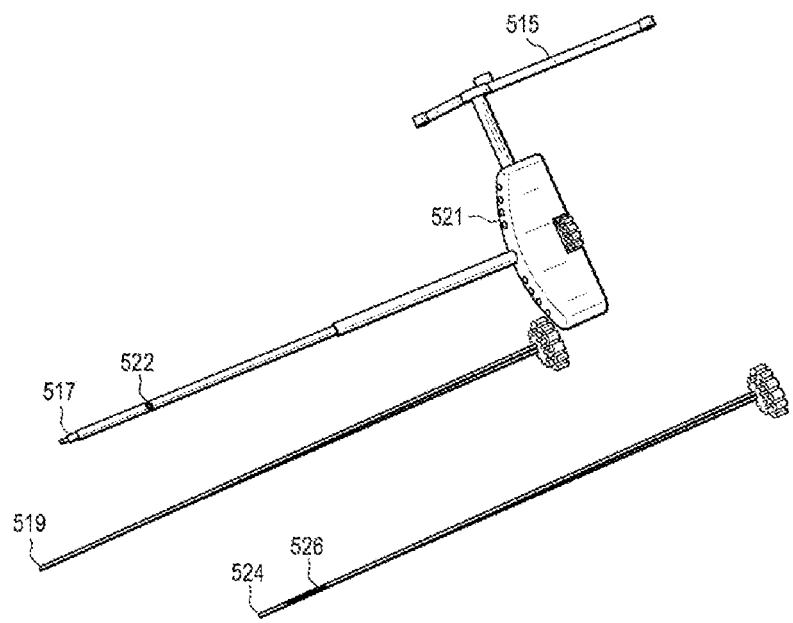

As noted above, the multi-tool can include integrated or built-in neuromonitoring, e.g., for detecting the presence, proximity, health, or other attributes of nerve tissue. For example, as shown in FIG. 56A, one or more shaft components of the multi-tool can include a neuromonitoring sensor 522. The sensor can include one or a plurality of sensors. The sensor can be configured to detect the presence, proximity, health, or other attributes of nerve tissue. For example, the sensor can be configured to assess nerve heath using functional near-infrared (fNIR) spectroscopy, e.g., as described in U.S. Application No. 62/507,930 filed on May 18, 2017, which is hereby incorporated herein by reference. As another example, the sensor can be configured to measure electrical nerve impulses, EEG, EMG, evoked potentials, or the like. Nerve assessment data can be communicated to the surgeon to inform subsequent surgical steps.

As also noted above, and as shown in FIG. 56A, the multi-tool can include an electrode, transducer, or other energy delivery element 526 for applying energy to tissue, e.g., to ablate or cauterize the tissue. The multi-tool can include an energy delivery element in the form of a microwave ablation element. The multi-tool can include an energy delivery element of the type used in the NEUWAVE system available from ETHICON, INC. of Cincinnati, Ohio. The energy delivery element can be built-into the multi-tool, or can be supported or guided to a target location using the multi-tool. The energy delivery element can be mounted on a shaft or needle 524. The needle can be coaxially received within or around another shaft component of the multi-tool. The multi-tool can be used to position the energy delivery element in proximity to a target location, such as an osseous bone tumor. Energy can be delivered from the energy delivery element to the tumor or other target location.

Pedicle Anchor

Figure 57:
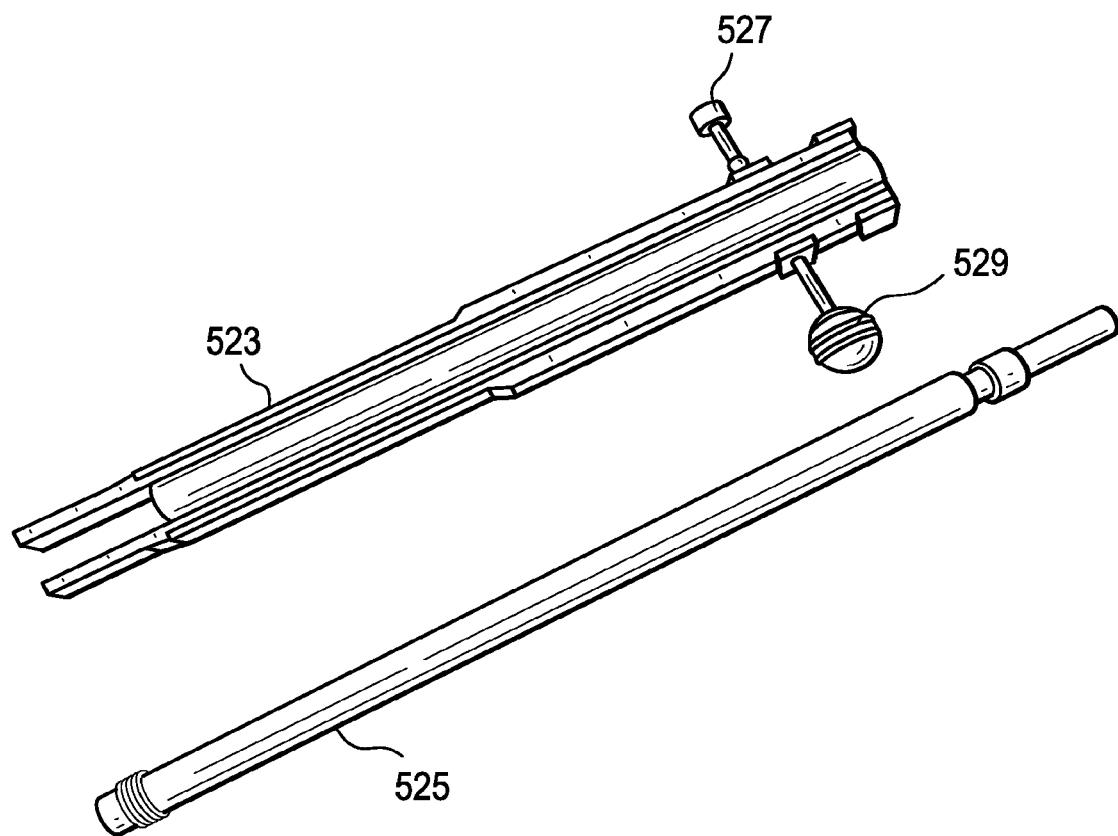

Now referring to FIG. 57, there is provided a Pedicle Anchor based on conventional screws that comprises a Center Core 523 including a Polyaxial Blocking Post 525, which engages with the thread for the Locking Cap of the Screw. When tightened, the polyaxiality of the screw is fully blocked. A screw 527 locks the Center Core with the Polyaxial Blocking Post. In other embodiments not including the above Pedicle Post with Reference Array, the interface to attached devices (Mini-Flex-Arm) is not realized by using a Clamp but by a non-detachable feature (sphere, 529). This provides sufficient stability and is a simple add-on to existing screw systems.

Dilatation Tubes

Figure 58:
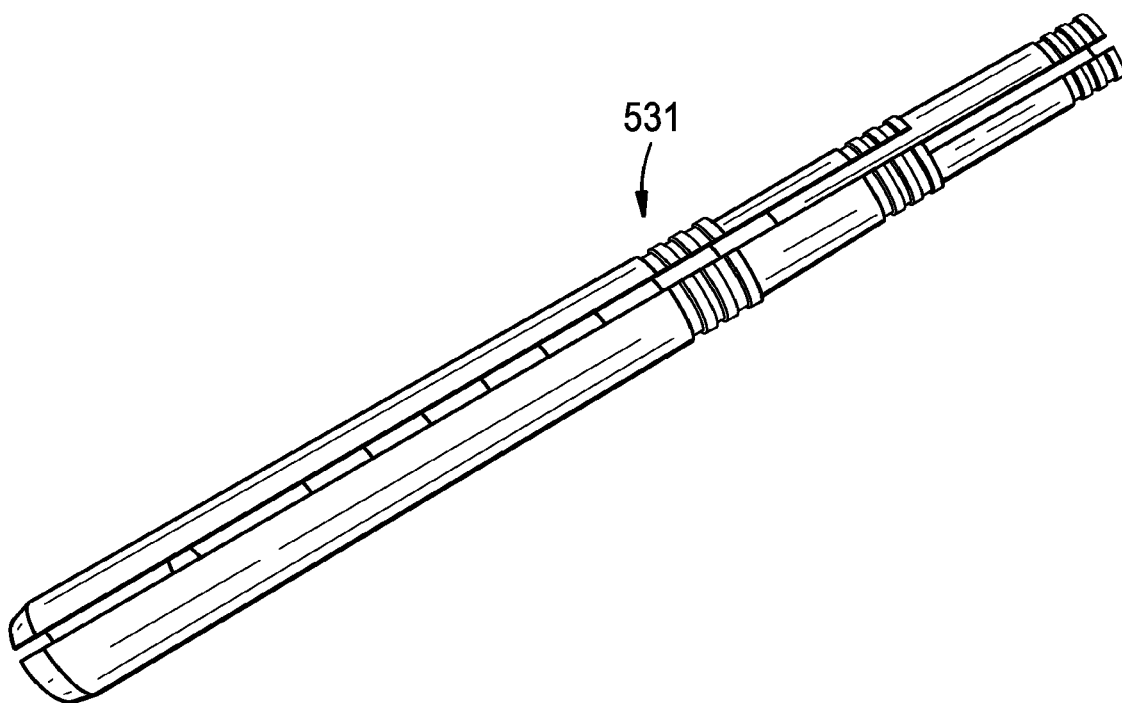

Now referring to FIG. 58, there is provided a dilation System comprising a set of Tubes 531 having outer diameters that match the current Access Tube (outer shield) inner diameters of 12 mm, 15 mm, and 18 mm. They are all circular shaped in the cross sectional plane and slotted in the longitudinal axis in order to be placed over the Multi-Tool probe (see above) and pass the connection of the Navigation Array with the cannulated cylindrical body of the Multi-Tool. In some embodiments, the set of Tubes have outer diameters (ODs) of OD1=12 mm, OD2=15 mm, and OD3=18 mm.

Mini-Flex Arm

Figure 59:
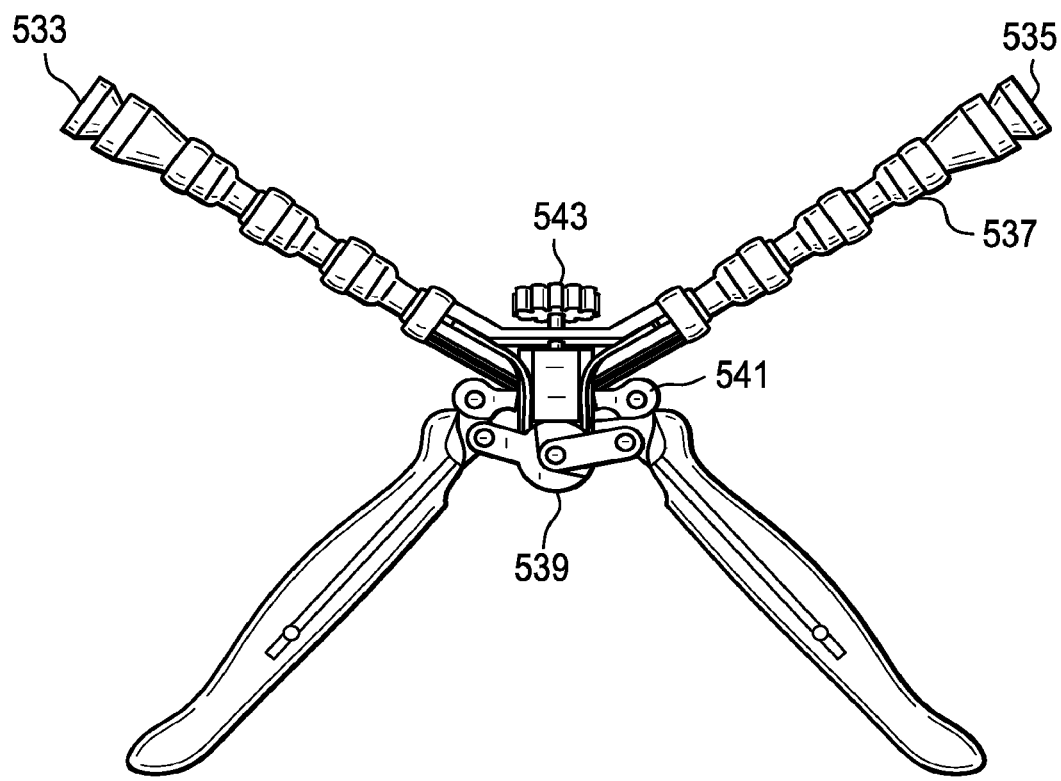

Now referring to FIG. 59, there is provided a Mini-Flex-Arm comprising of two clamps 533, 535 that are attached to spherical connectors on the Pedicle Anchor and Access Tube (outer shield) and therefore allows for a polyaxial adjustment to the attached devices. In an unlocked position, the segmented arms with ball and socket elements 537 in combination with the polyaxial clamps allow for a non-restricted 3-dimensional placement of the Access Tube (outer shield). The System can be locked with a single point handle 539 that tightens a multi-core wire 541. A potential elongation of the wire over time which would have a negative effect on the fixation properties of the device can be compensated on a screw 543 by adjusting the effective length of the wire.

Access Tube (Outer Shield) with Soft Tissue Retractor

Figure 60:
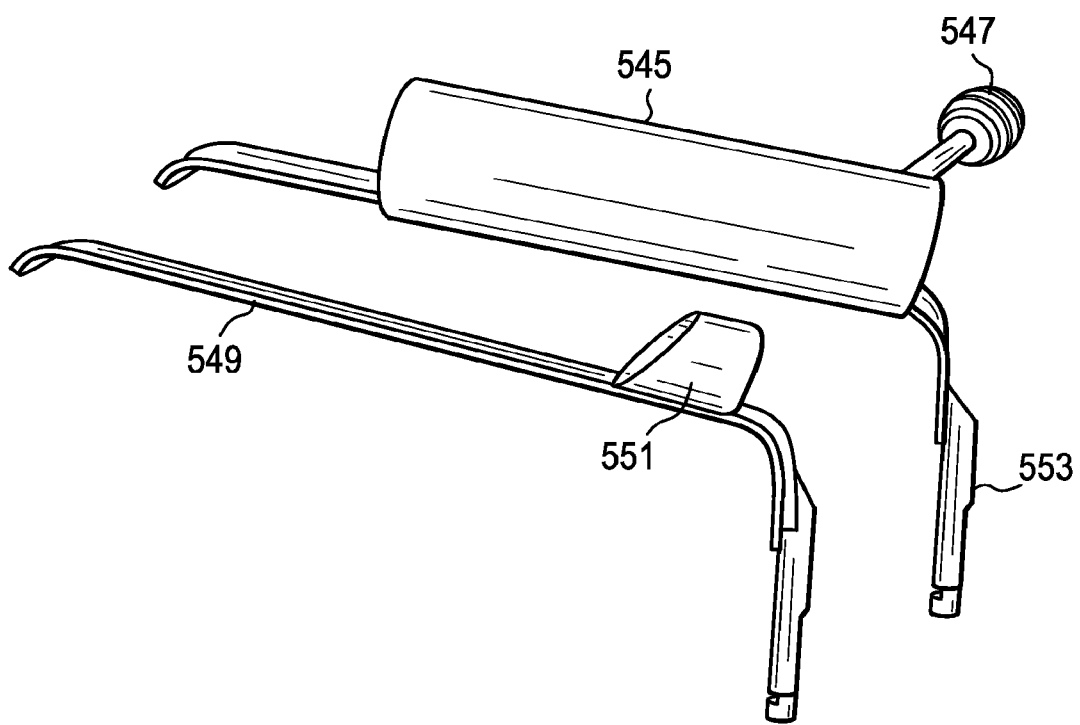

Now referring to FIG. 60, there is provided an Access Tube (outer shield) 545, which is a simple cylindrical tube with a distal flange, with a non-detachable feature (sphere 547) that connects it with the Mini-Flex-Arm. The Soft-Tissue-Retraction-Blade (inner shield) 549 is placed within the Access Tube. An attached spring 551 allows for a central insertion. As soon as the blades get released (handle, 553), the spring pushes the Blade (inner shield) against the inner wall of the Access Tube (outer shield) and therefore retracts the soft tissue on its distal end. The Blade (inner shield) remains free rotation and is held with the Access Tube (outer shield) by a pure fictional force. In some embodiments, there is the option to use two Soft-Tissue-Retraction Blades (inner shields) at the same time which would meet the requirements to use this embodiment for TLIF Procedures since it allows for the retraction of the transverse as well as the exiting nerve. In some embodiments, the Detachable Handle is replaced by a simple permanent handle with a length of about 25 mm.

Access Tube (Outer Shield) with Integrated Endoscopy

Figure 61:
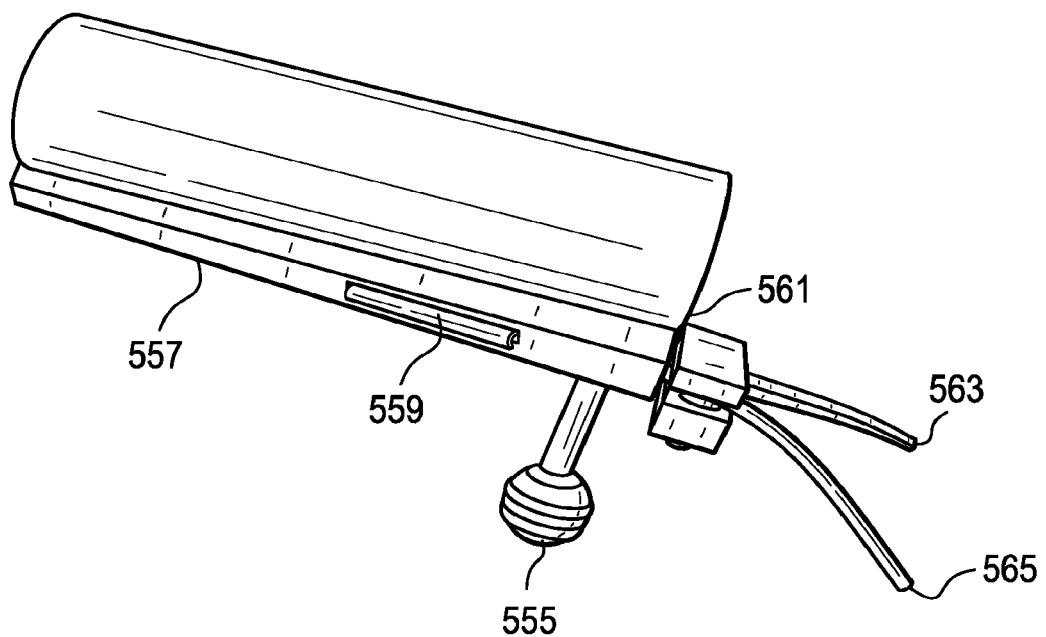

Now referring to FIG. 61, there is provided an Access Tube (outer shield) with an integrated endoscope and a non-detachable feature (sphere 555) that connects it with the Mini-Flex-Arm. The depth adjustable Endoscope System is held in a channel 557 that has a spring feature 559 to increase the friction and therefore hold the endoscope in place. The Endoscope system 561 consists of the endoscope itself (OD=4 mm) and 2 tubes, one for irrigation 563 and the other one for suction 565. In some embodiments, the Endoscope is depth adjustable. In some embodiments, the endoscope's channel will be parallel to the Access Tube (outer shield) Lumen.

Navigation Plug

Figure 62:
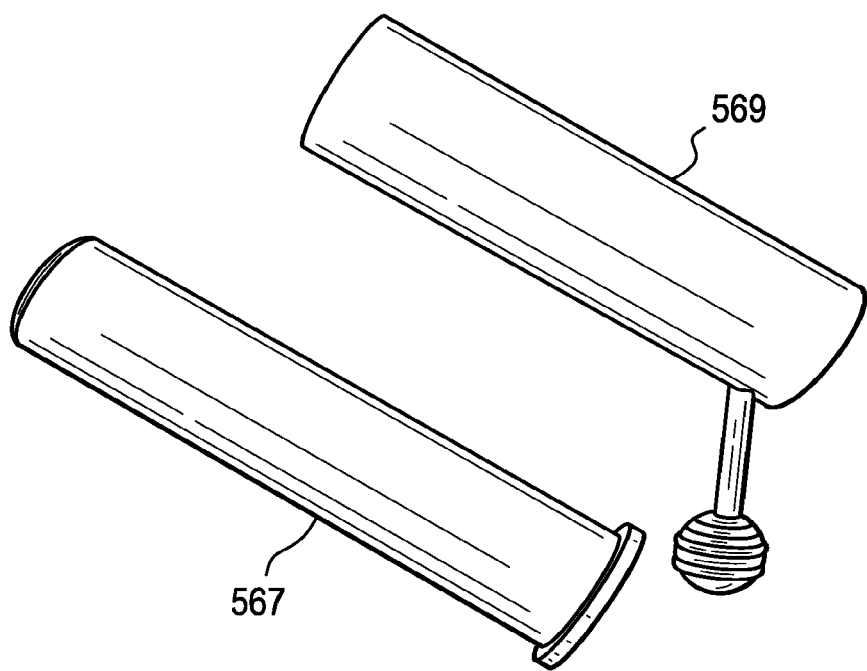

Now referring to FIG. 62, in some embodiments, there is a Navigation Plug 567 that is placed in the Access Tube (outer shield) 569 and allows the placement of the Multi-tool (see above) in the Center of the Access Tube (outer shield) flush with its distal end. This embodiment allows the visualization of the central longitudinal axis of the Access Tube (outer shield) as well as its distal end in the Navigation System. Because, in some embodiments, access trajectory is considered to be of higher importance than depth, the trajectory line could be graduated to offer information of depth in combination with known port length.

Discectomy Tool with Handle

Figure 63:
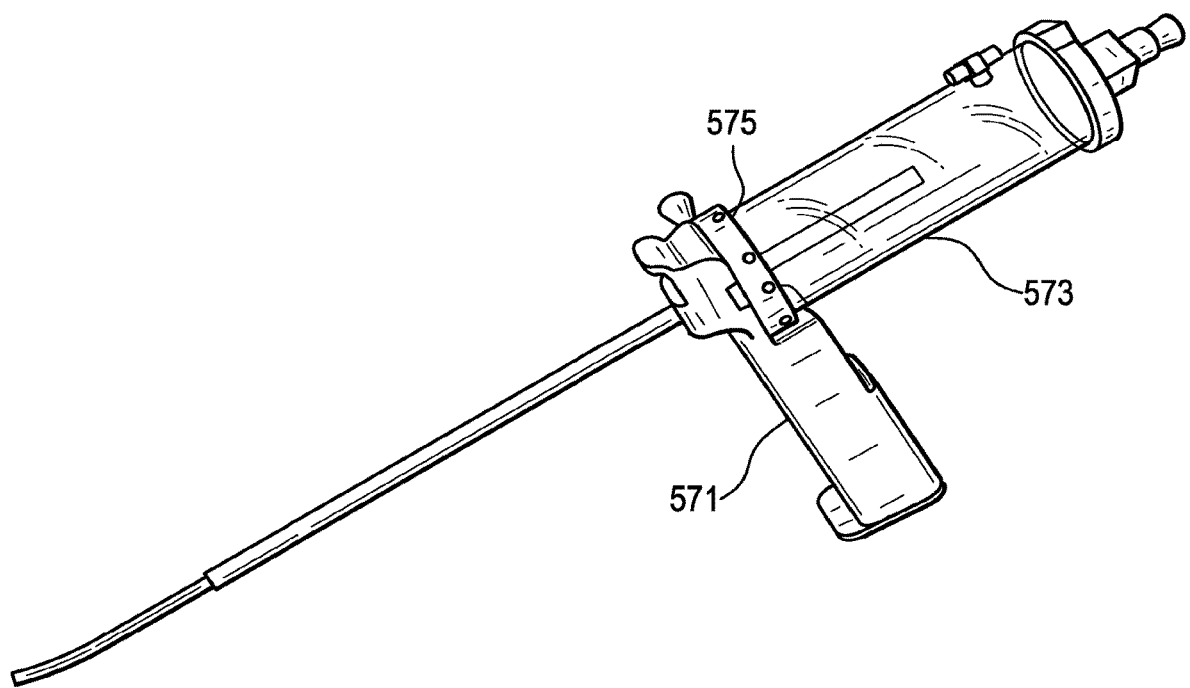
Figure 64:
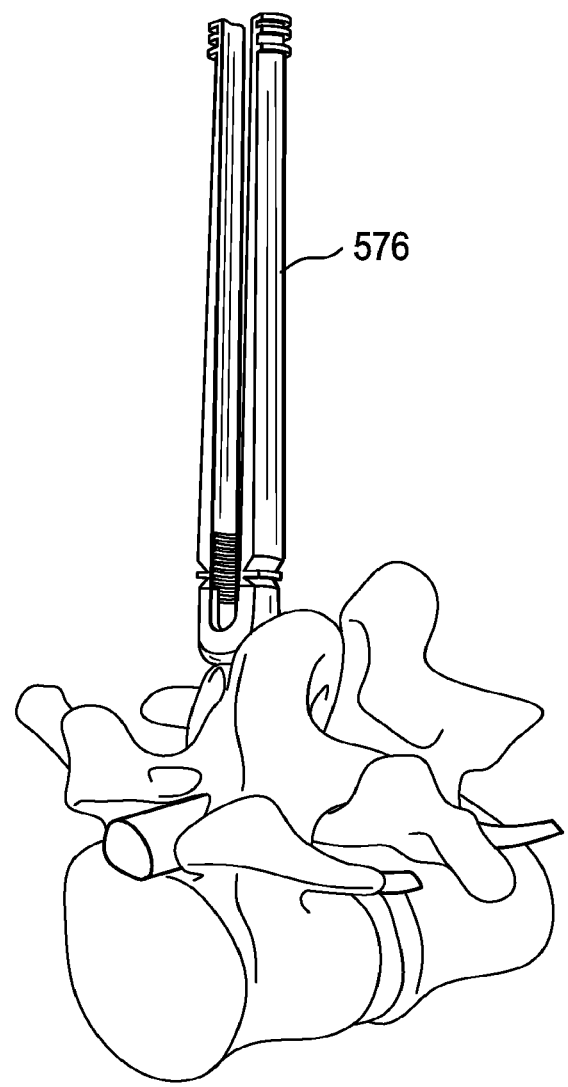
FIGS. 64-90 disclose some of the instruments in their contemplated in-spine use orientations in preferred procedures disclosed herein.
Figure 65:
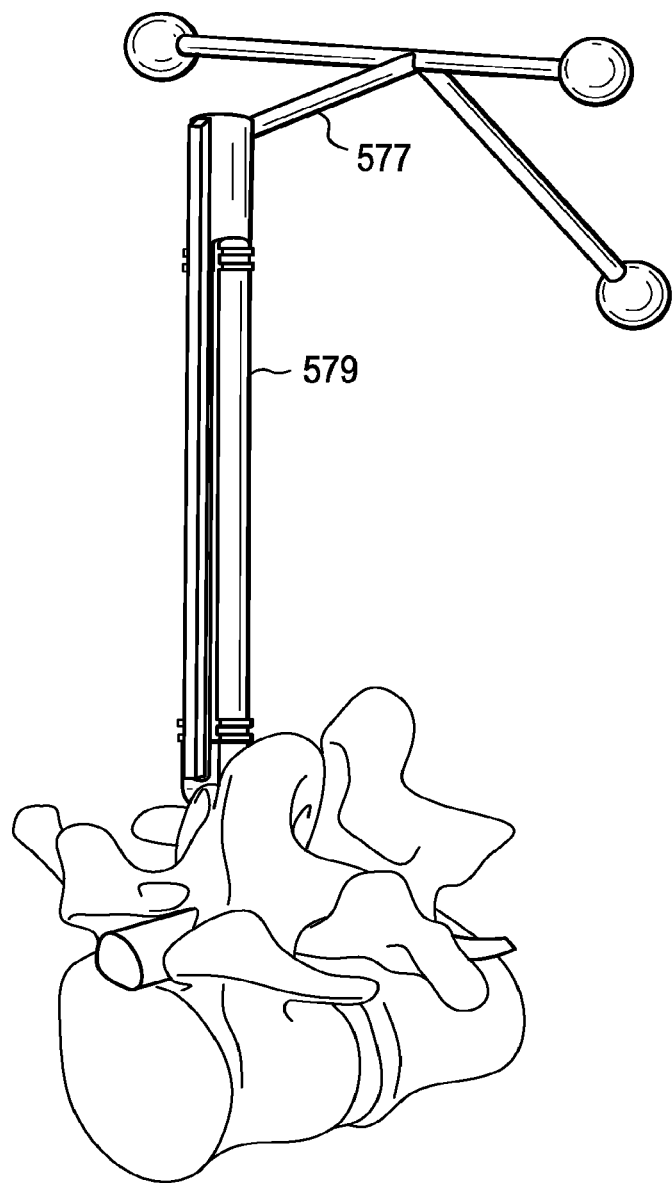

Now referring to FIG. 63, there is provided an attachable handle 571 directly attached to a standard suction-based discectomy tool 573 via an Adapter Plate 575 that clamps to the discectomy tool containment with 3 screws. In a first embodiment of this Adapter Plate, it only holds the attachable Handle, while in a second version it holds an additional Navigation Array. The Navigation Array is pre-calibrated: After letting the Navigation System know what specific discectomy tool is currently used, it shows the correct dimension and tip of the device in the pre-registered x-ray views in real time.

FIGS. 64-90 disclose some of the instruments in their contemplated in-spine use orientations in preferred procedures disclosed herein.

Step 1 Placement of Ref. Array
    Step 2 Placement of Pedicle Anchor
    Step 3 Placement of Access Tube
    Step 4 SAP Removal
    Step 5 Soft Tissue Retraction
    Step 6 Disc Removal
    Step 7 Insertion of Expandable Cage and Bone Substitute
    Step 8 Posterior Stabilization Step 1 Placement of Reference Array Now referring to FIGS. 64-65, in one embodiment, a polyaxial screw is inserted contra-laterally into the spine via post 576. A navigation reference array 577 is then fixed mounted on a Polyaxial Blocking Post 579, and engaged in the distal thread (not visible, inside screw/tab) for the Locking Cap of the Pedicle Screw.

Step 2 Placement of Pedicle Anchor

Figure 66:
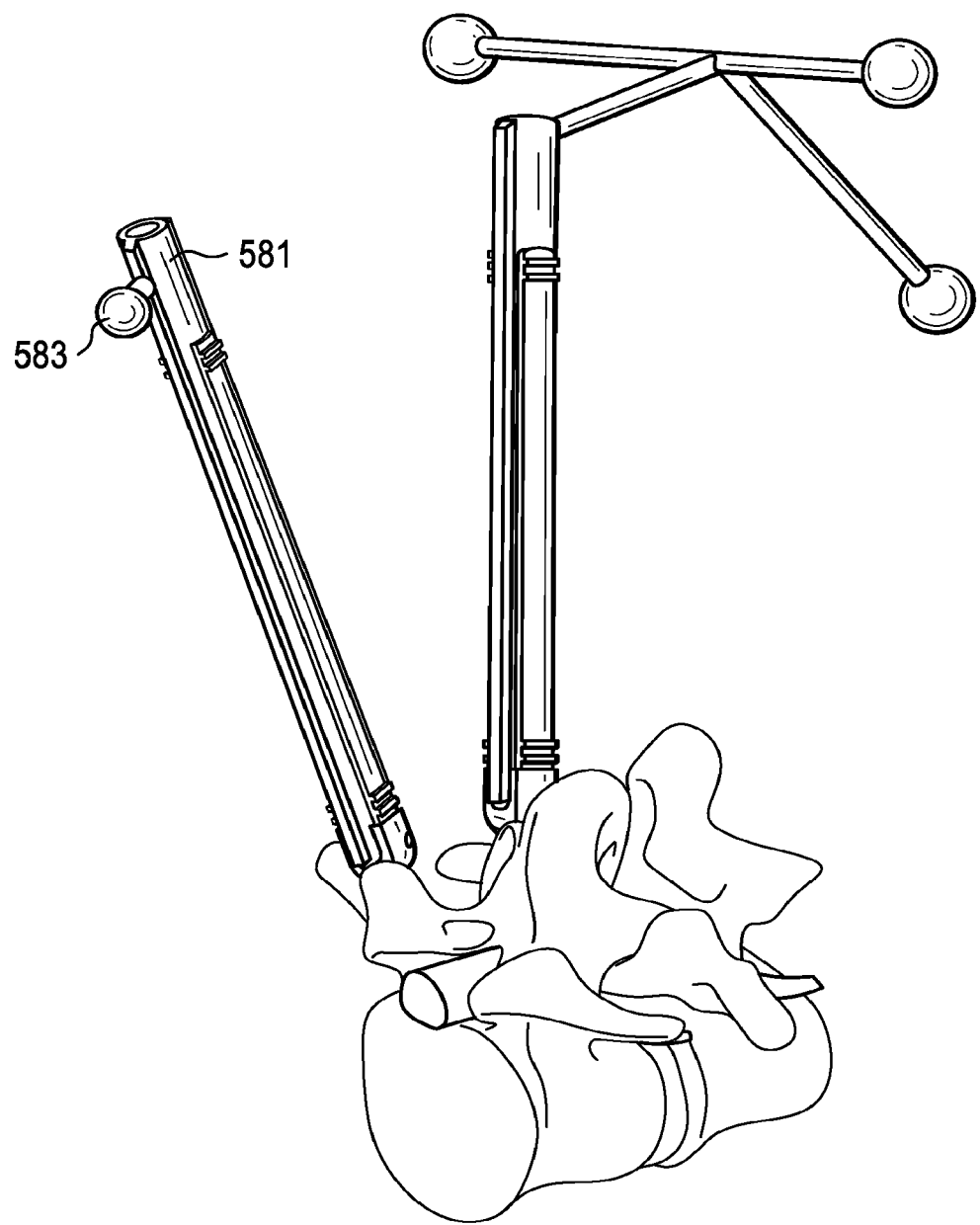

Now referring to FIG. 66, a pedicle Anchor 581 with Connector Interface 583 is placed on the contralateral side.

Figure 67:
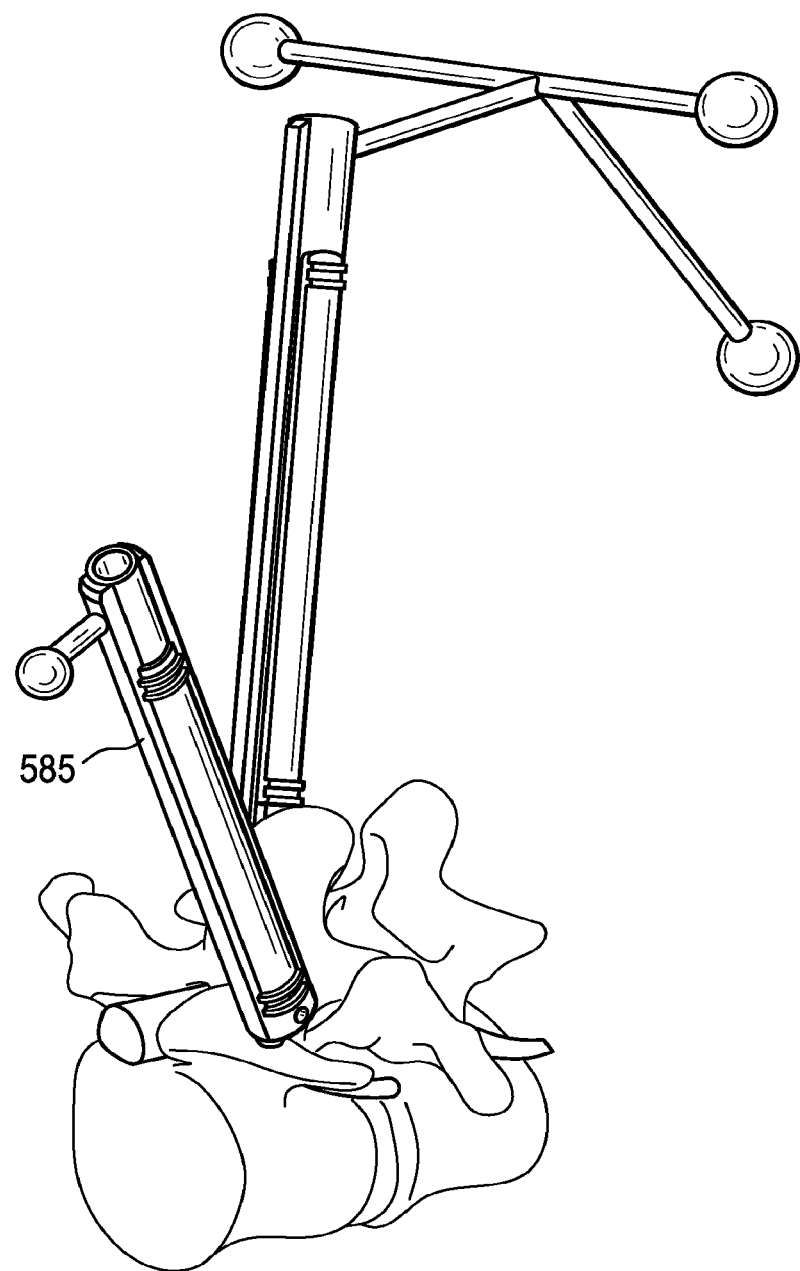

Now referring to FIG. 67, a pedicle anchor 585 is placed on the ipsilateral side.

Step 3 Placement of Access Tube

Figure 68:
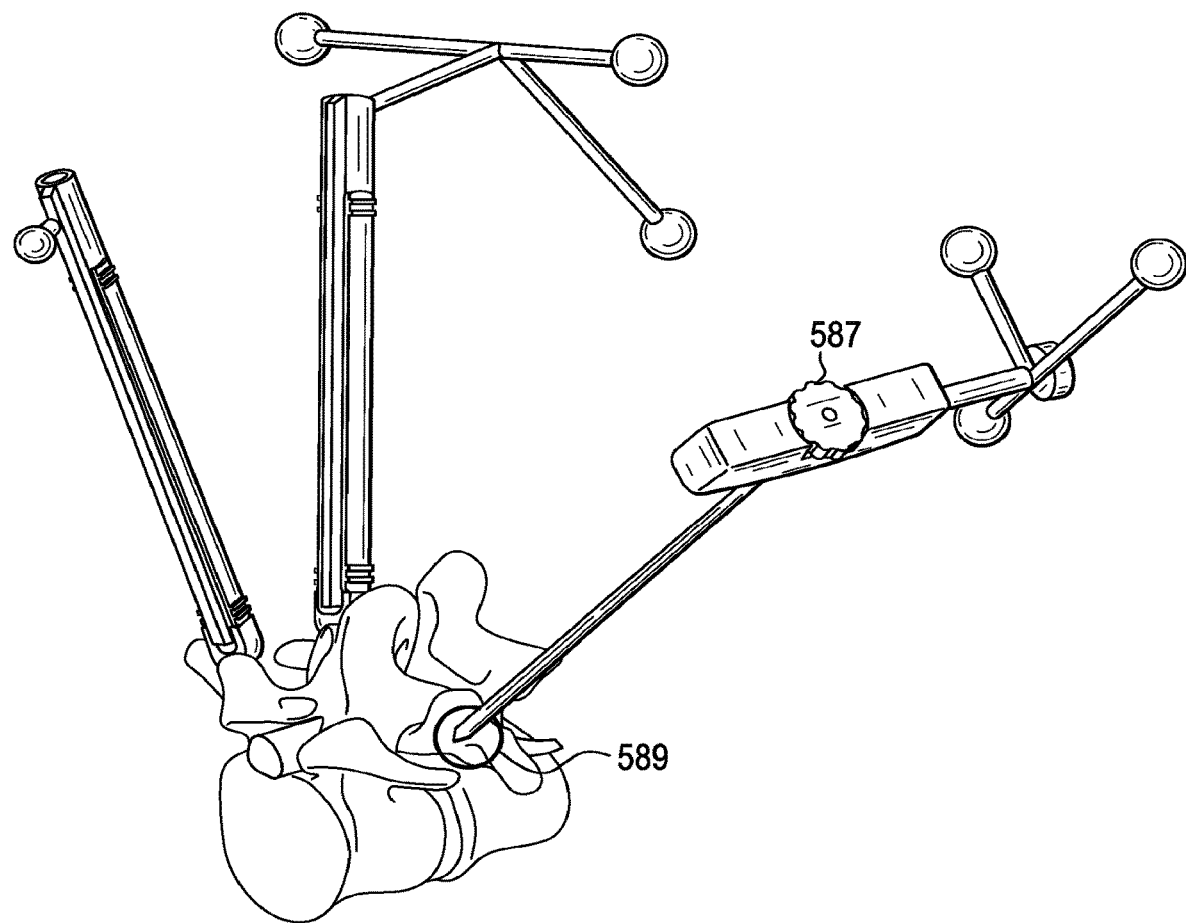

Now referring to FIG. 68, a Multitool 587 is inserted into the spine for determination of Target Area 589 and trajectory of Dilators/Access Tube. Neuromonitoring features of the multi-tool can be used during insertion or at any other desired time to avoid or navigate around nerve tissue, to safely retract nerve tissue, and/or to assess the health of nerve tissue.

Figure 69:
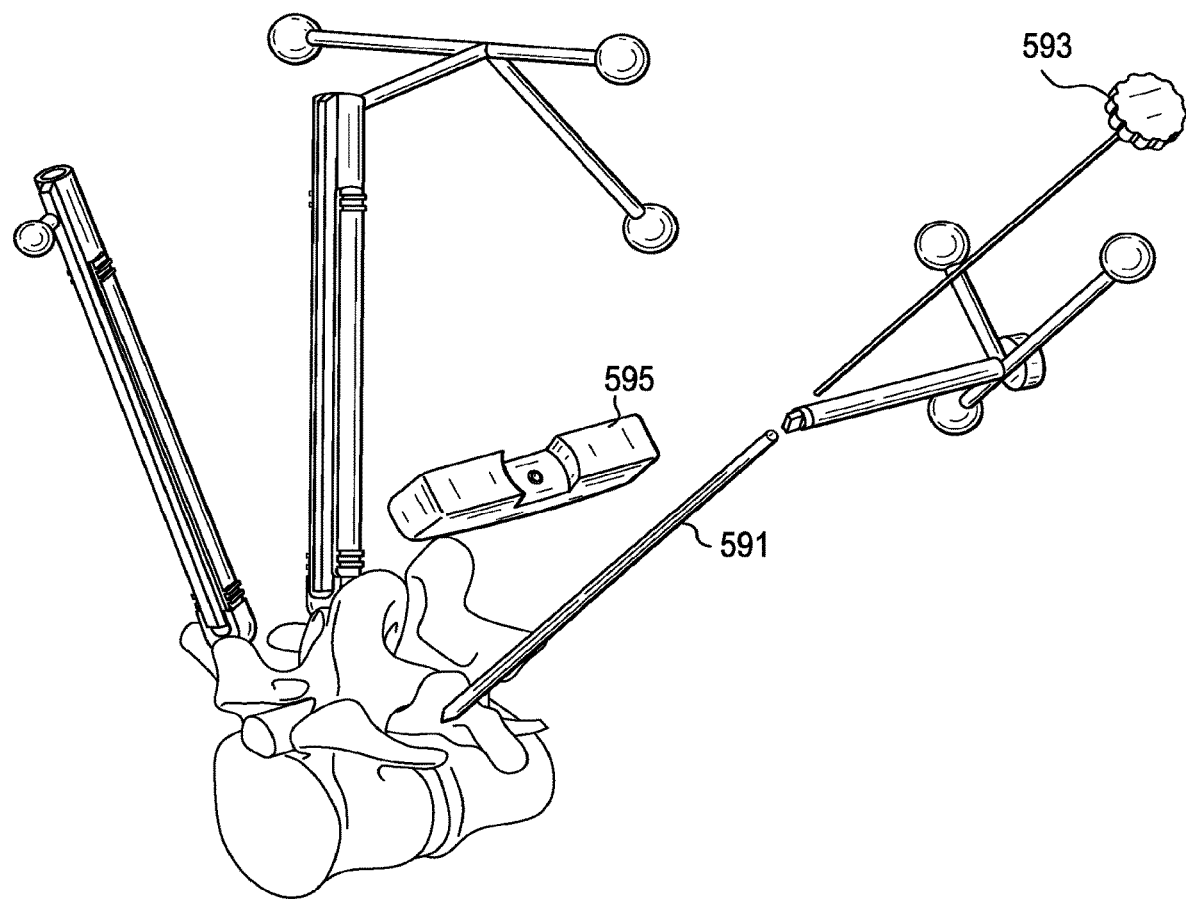

Now referring to FIG. 69, the K-Wire and Handle are removed from the multi-tool for next step. After placing the Multitool 591, the K-Wire 593 needs to be removed in order to allow the removal of the Handle 595.

Figure 70:
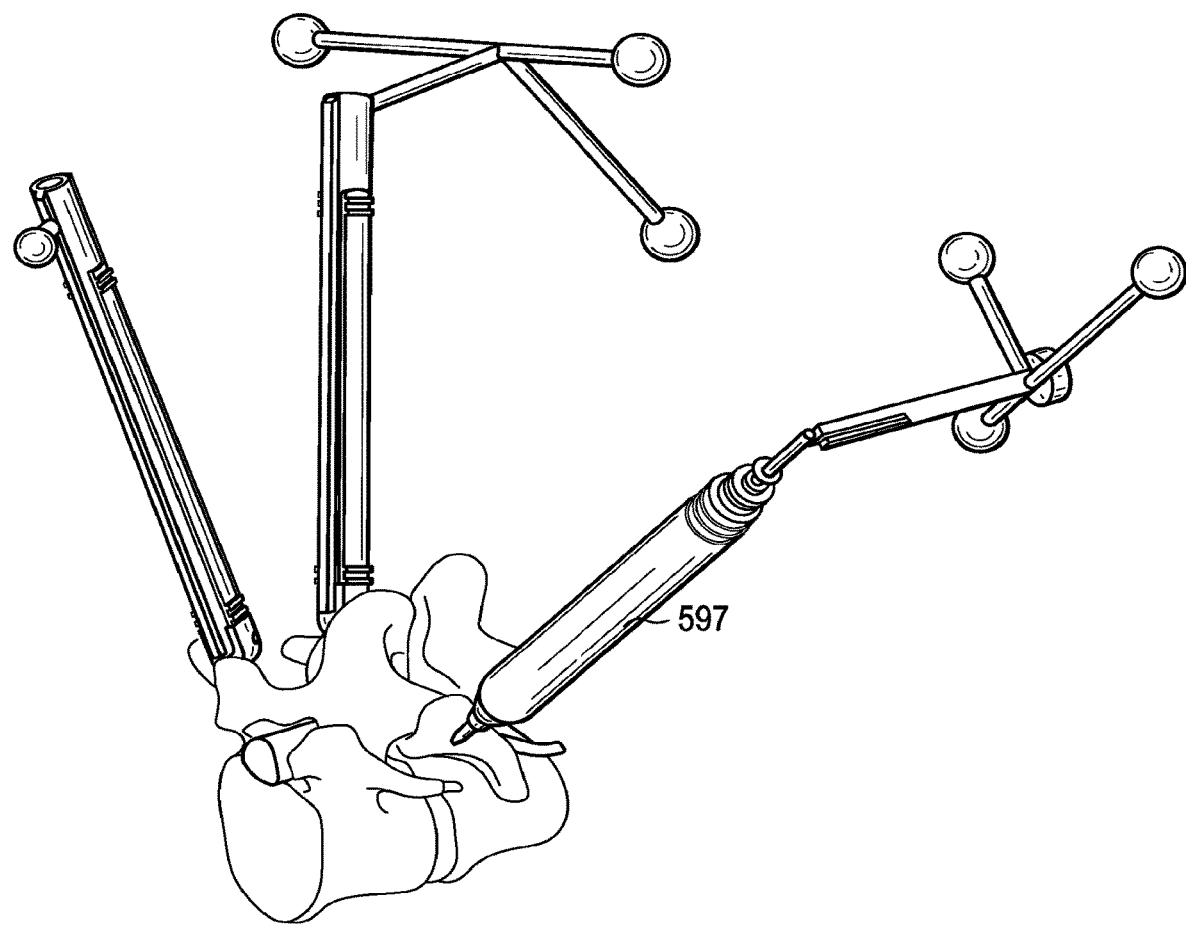

Now referring to FIG. 70, Multi-step dilation is carried out to prepare for Access Tube (outer shield) insertion. The removal of the handle (see previous step) allows the placement of the first, second and third dilators 597 to prepare for Access Tube insertion.

Figure 71:
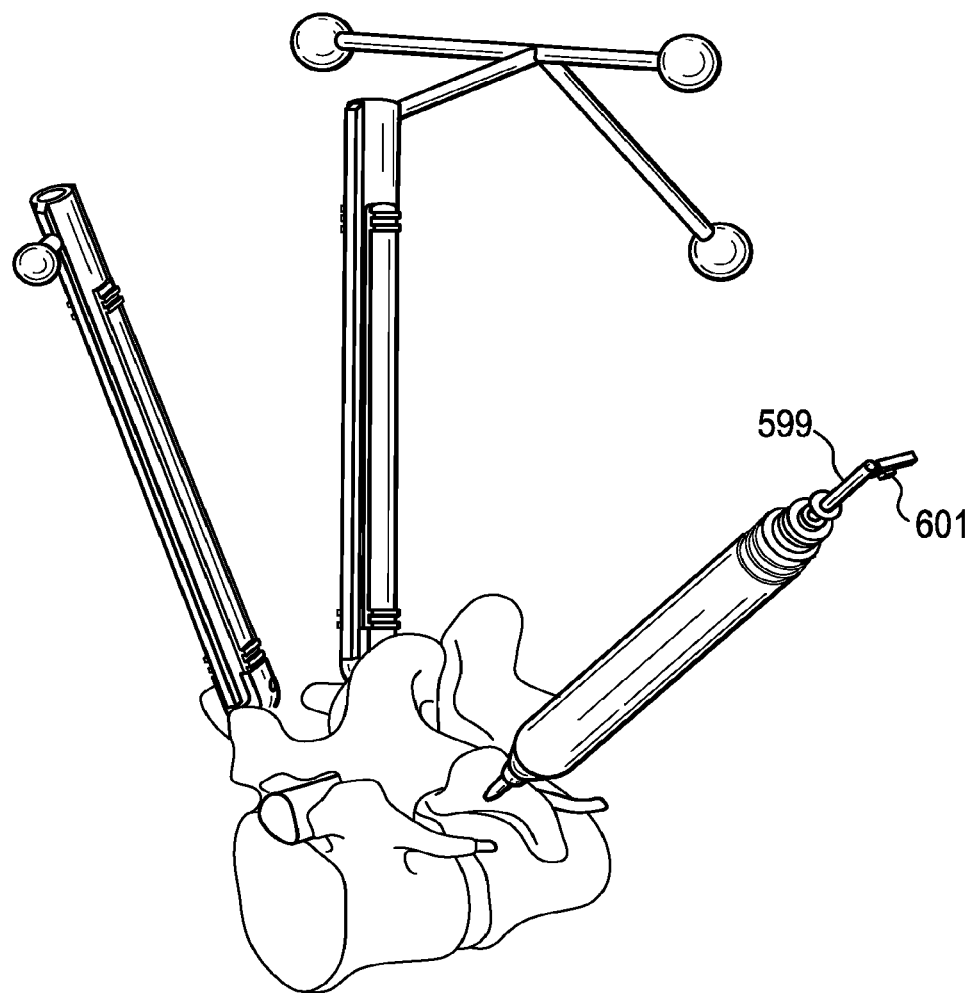

Now referring to FIG. 71, the navigation array is removed from the Multi-tool base. Since it is clinically important to keep the target point of the Access Tube (outer shield) positioning, the Access Port can be placed over the main Body 599 of the Multi-Tool by removing the Navigation Array, leaving behind the Navigation Array Interface 601, which allows a play free, load bearing and bi-unique fixation of the Reference Array.

Figure 72:
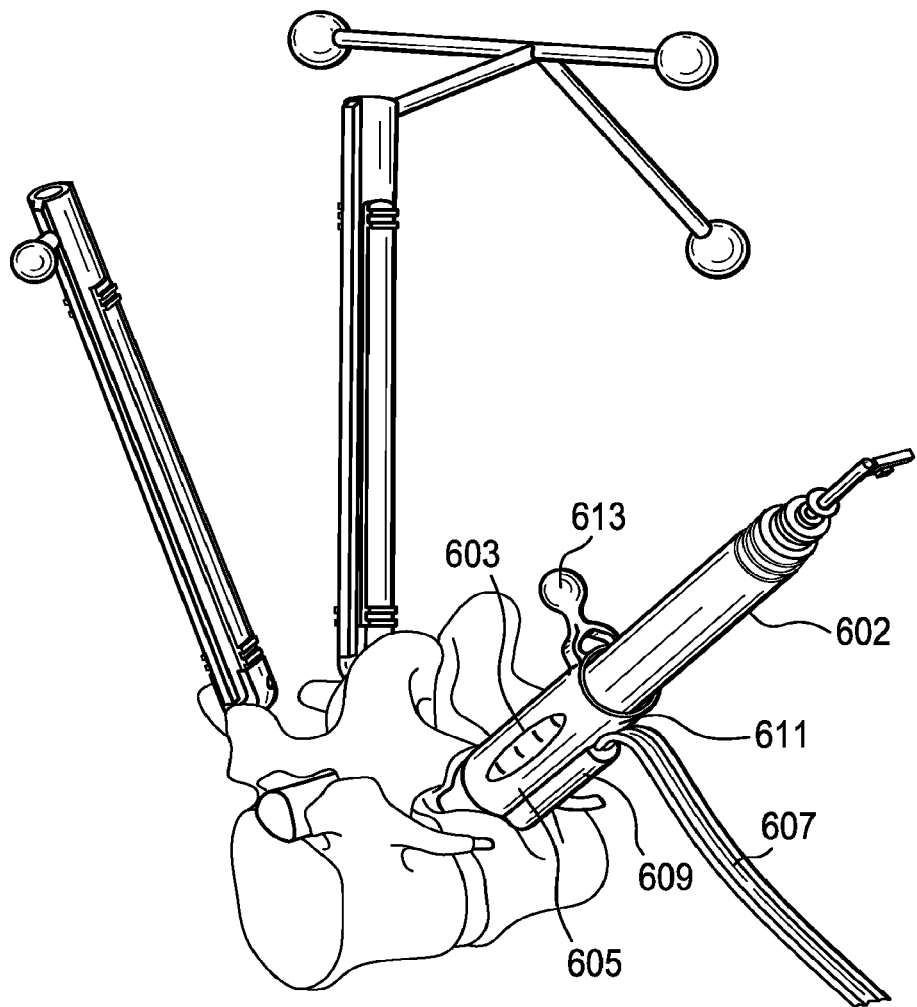

Now referring to FIG. 72, the Access Tube (outer shield) is inserted over the dilators 602 (wherein the viewing element Chip-on-tip scope is pre-mounted). The Access Tube (outer shield) is telescopic and can be adjusted in length, stabilized with a ratchet mechanism 603. It comprises a distal segment 605 that holds a depth adjustable Chip-on-Tip Camera 607 housed in a channel 609 which is integrated into the wall of the distal segment. A proximal portion of the access tube (outer shield) 611 slides over the distal segment and holds a connector interface 613.

Figure 73:
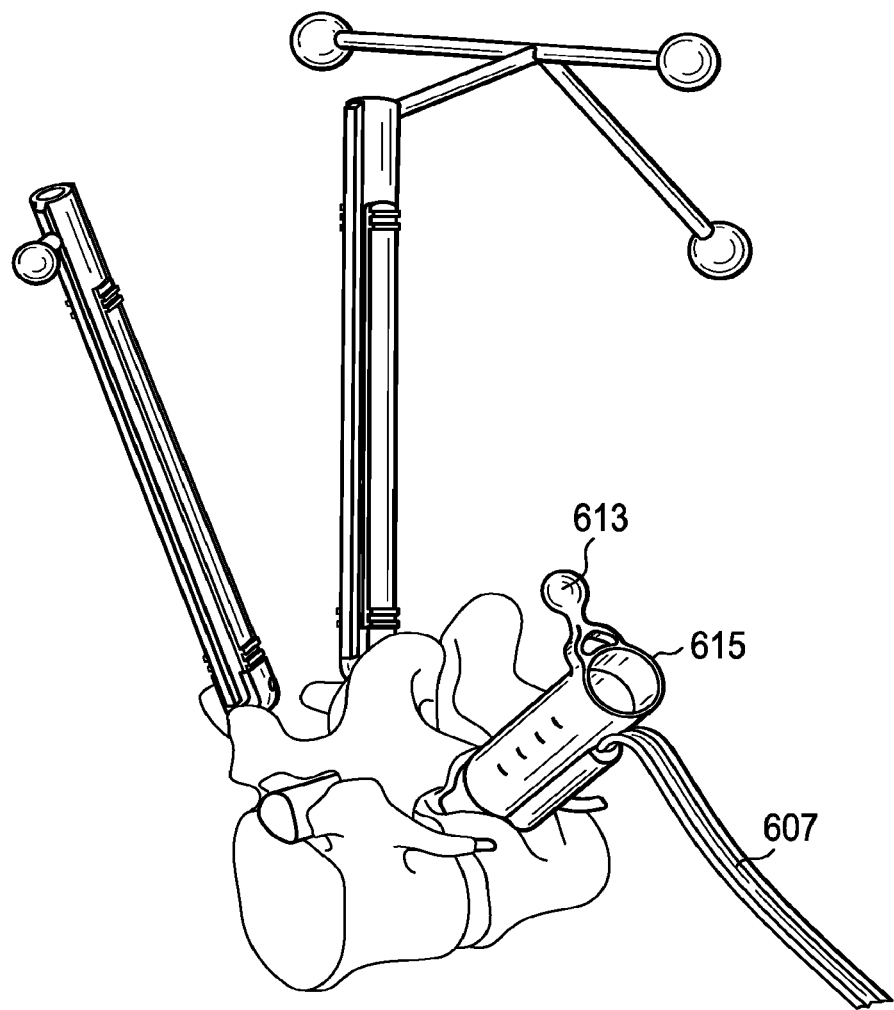

Now referring to FIG. 73, once the Dilators as well as the Body of the Multi-Tool have been removed, the Access Tube (outer shield) 615 offers free access to the SAP.

Figure 74:
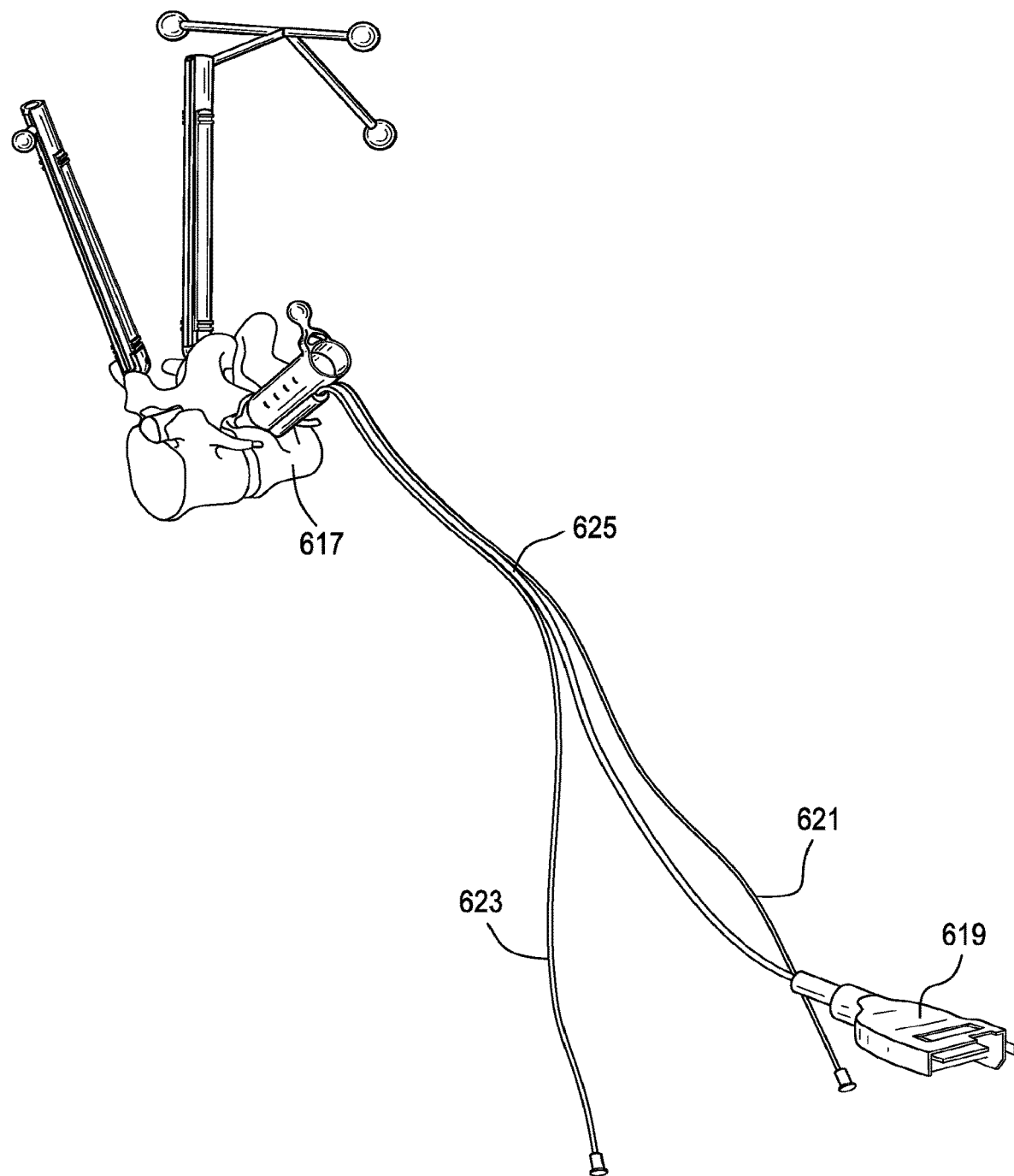

FIG. 74 discloses connectors to the Visualization Box and the Cleaning Box (water and suction). The Chip-on-Tip Camera comprises the actual Camera 617 disposed in the access tube (outer shield) and a main connector plug 619 that provides power supply, data cables and light to the Camera. There are also two tubes for irrigation and suction 621, 623 to provide a cleaning feature for the Camera Lens, which merge into a single cable 625 connected to the Camera and extending from the access tube (outer shield).

Figure 75:
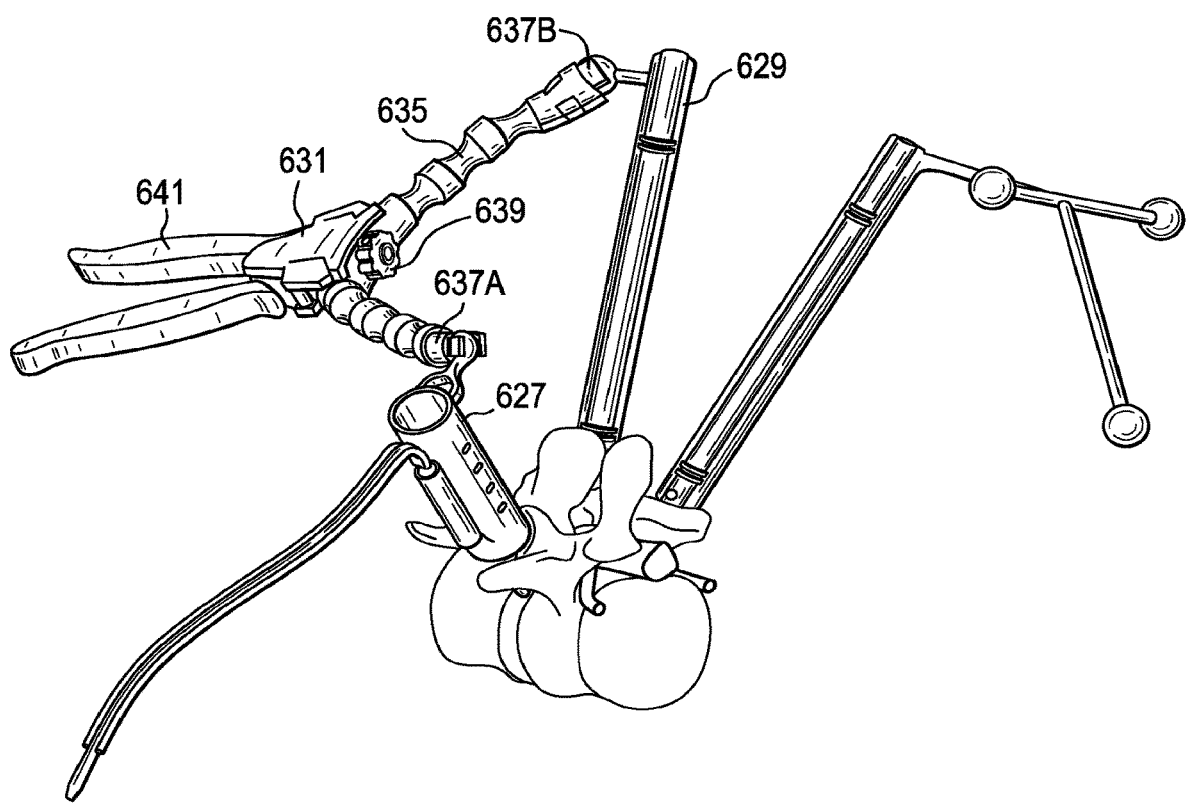

Now referring to FIG. 75, the Access Tube (outer shield) is fixed to the ipsilateral or contralateral pedicle anchor. The Access Tube 627 is rigidly attached to the contralateral 629 or ipsilateral (not shown) Pedicle Anchor via a Connector 631. This Connector allows the locking of the Access Tube in any 3D position. It comprises ball and socket segments 635, two Interface Clamps 637a, 637b and an inner wire (not visible) that is put under tension by an adjustable 639 single point fixation handle 641 and thereby blocks the single joints of the two Interface Clamps and segments by increasing their absolute friction. The single point fixation Connector is designed to minimize the accruing forces on the Access Tube, as well as the pedicle Anchor, during tightening of the construct. Another Connector Design (not shown) is reverse in function, in that it is permanently stable unless the inner wire is released via the single point fixation Handle.

Step 4 SAP Removal

Figure 76:
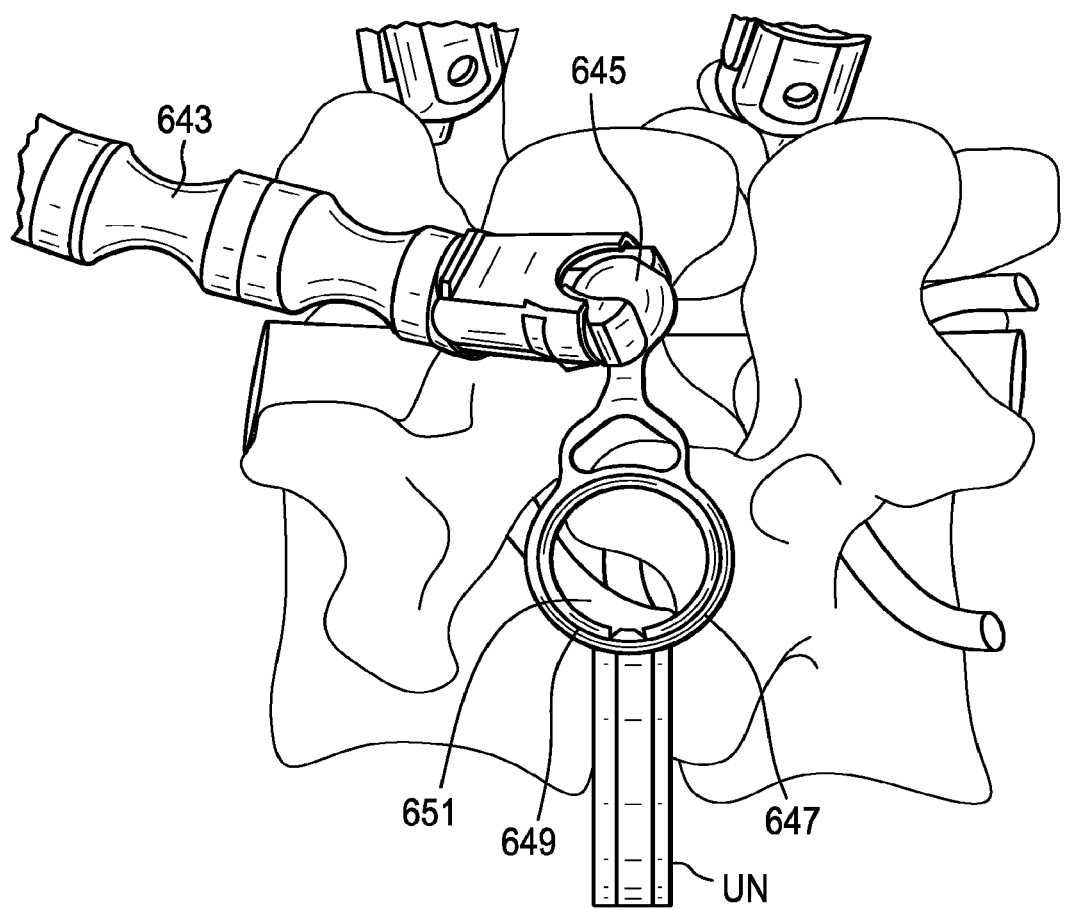

Now referring to FIG. 76, there is provided an axial view of the Access Tube, wherein the surgeon is ready to start cutting the SAP. Disclosed in the FIG. are Single segment 643 and Connector Interface 645 of the Mini-Flex arm, outer proximal portion 647 of a Telescopic Access Tube; Inner distal portion 649 of Telescopic Access Tube; Cable of integrated Chip-on-Tip Camera 651; and unretracted Nerve UN.

Figure 77:
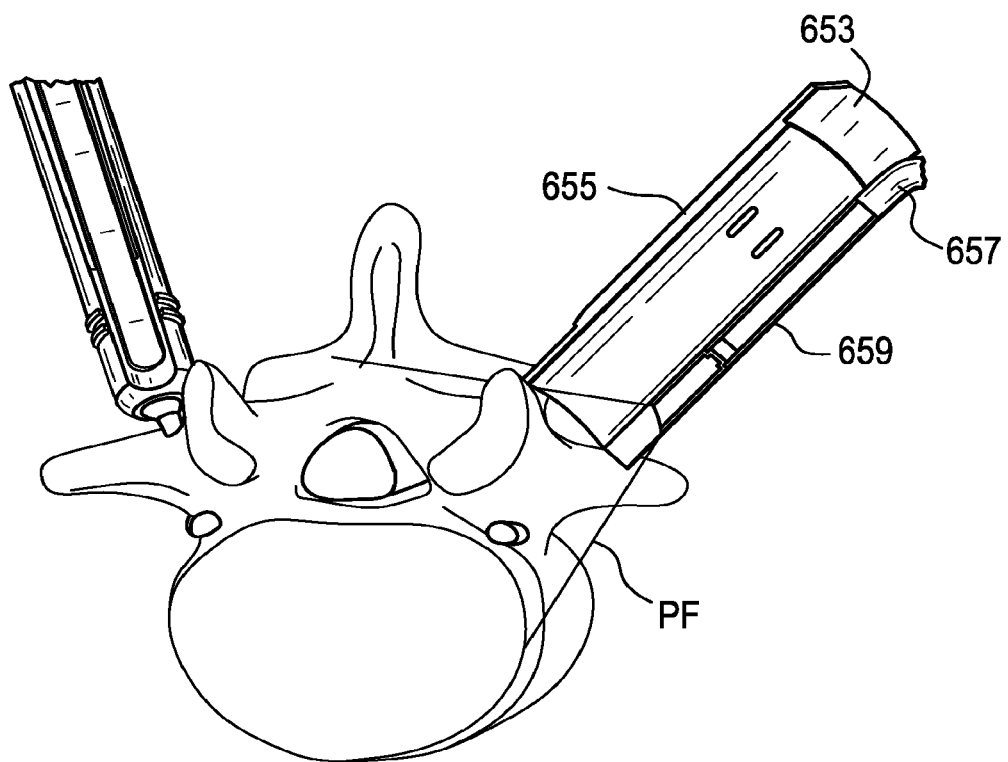

Now referring to FIG. 77, there is provided disposition of an Integrated Scope, which includes Outer proximal Tube 653 of Telescopic Access Tube; Inner distal Tube 655 of Telescopic Access Tube; Exiting Cable of integrated Chip-on-Tip Camera 657; Chip-on-Tip Camera in housing 659; and Projected field of view of Chip-on-Tip Camera PF.

Figure 78:
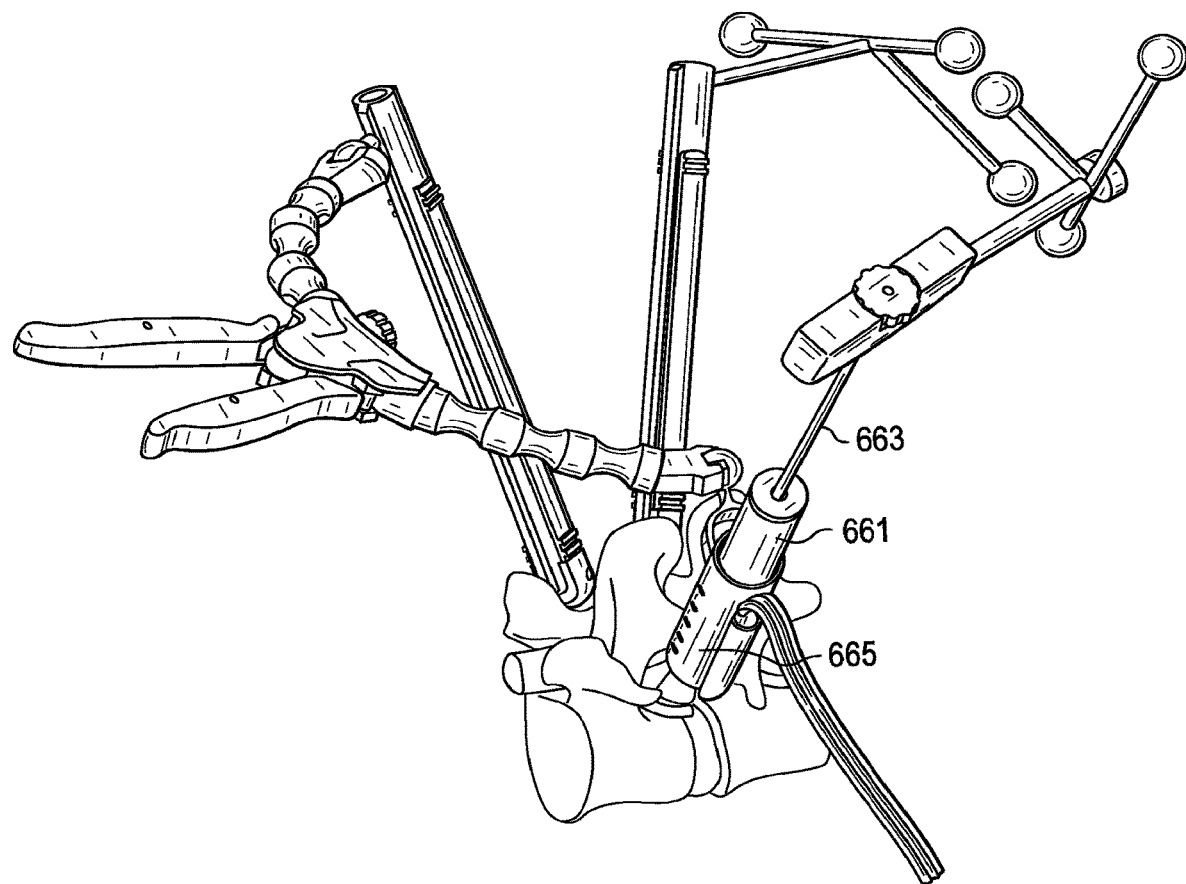

Now referring to FIG. 78, in some embodiments, there is optional Navigation of the Access Tube through use of the Multi-Tool with a Navigation Plug. In conjunction with a Navigation Plug 661, the Multi Tool 663 can also be used to visualize the trajectory as well as the distal end of the Access Tube 665 using navigation. The Navigation Plug sits on the proximal rim of the inner distal tube of the telescopic Access Tube, which leads to an accurate visualization of the depth perception independently from the position of the outer proximal tube and therefore total length of the Access Tube.

Figure 79:
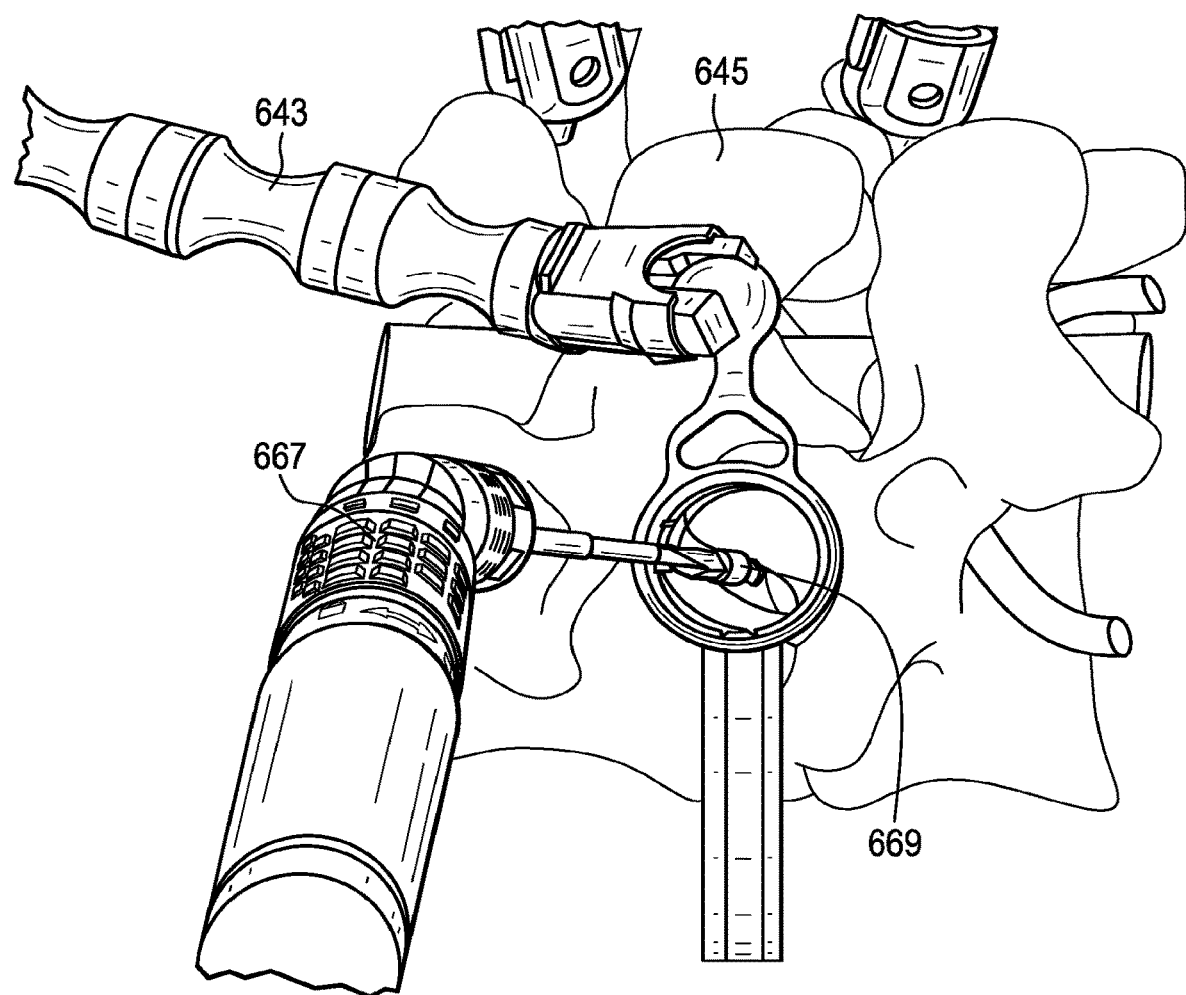

Now referring to FIG. 79, there is provided carrying out SAP removal via the use of MIS high-speed drills or manual tools. The SAP will be (partly) removed using a high speed Power Tool such as an Anspach System 667. The Burr 669 will be partly shielded to increase safety.

Figure 80:
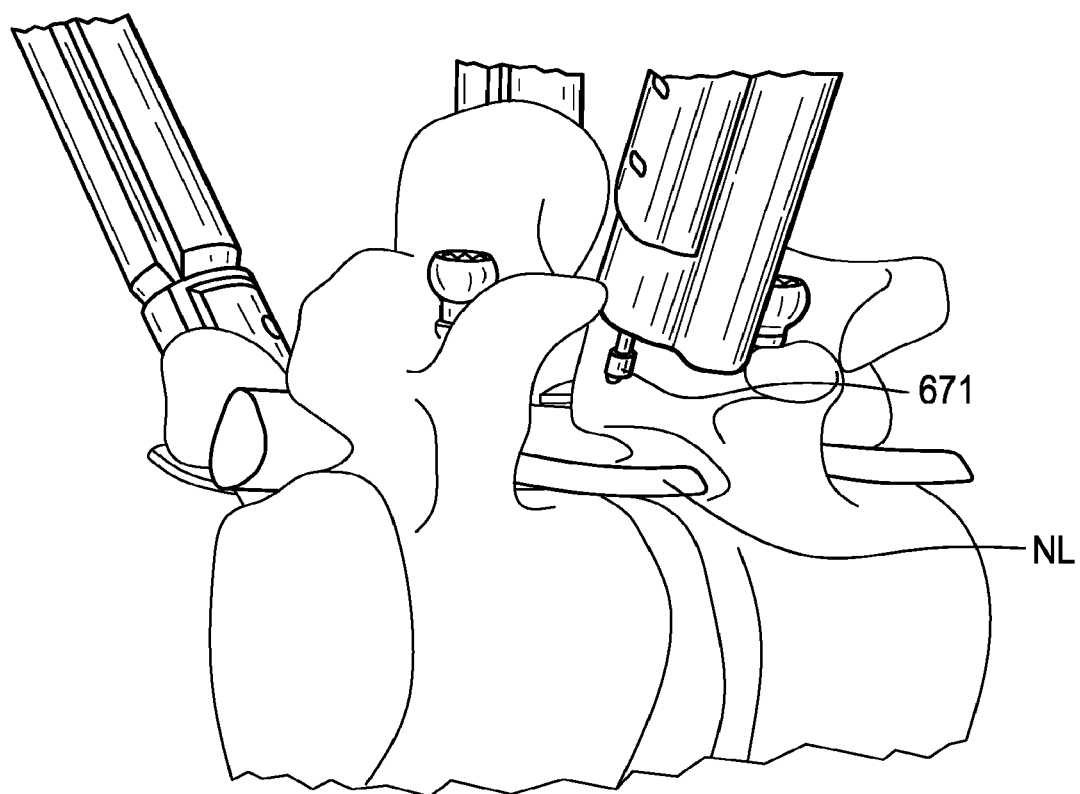

Now referring to FIG. 80, further SAP removal by MIS high-speed drills or manual tools is demonstrated with respect to the different anatomical planes. The removal of the SAP with a Burr 671 takes place about 10 mm-20 mm above the nerve (2) level NL.

Step 5 Soft Tissue Retraction

Figure 81:
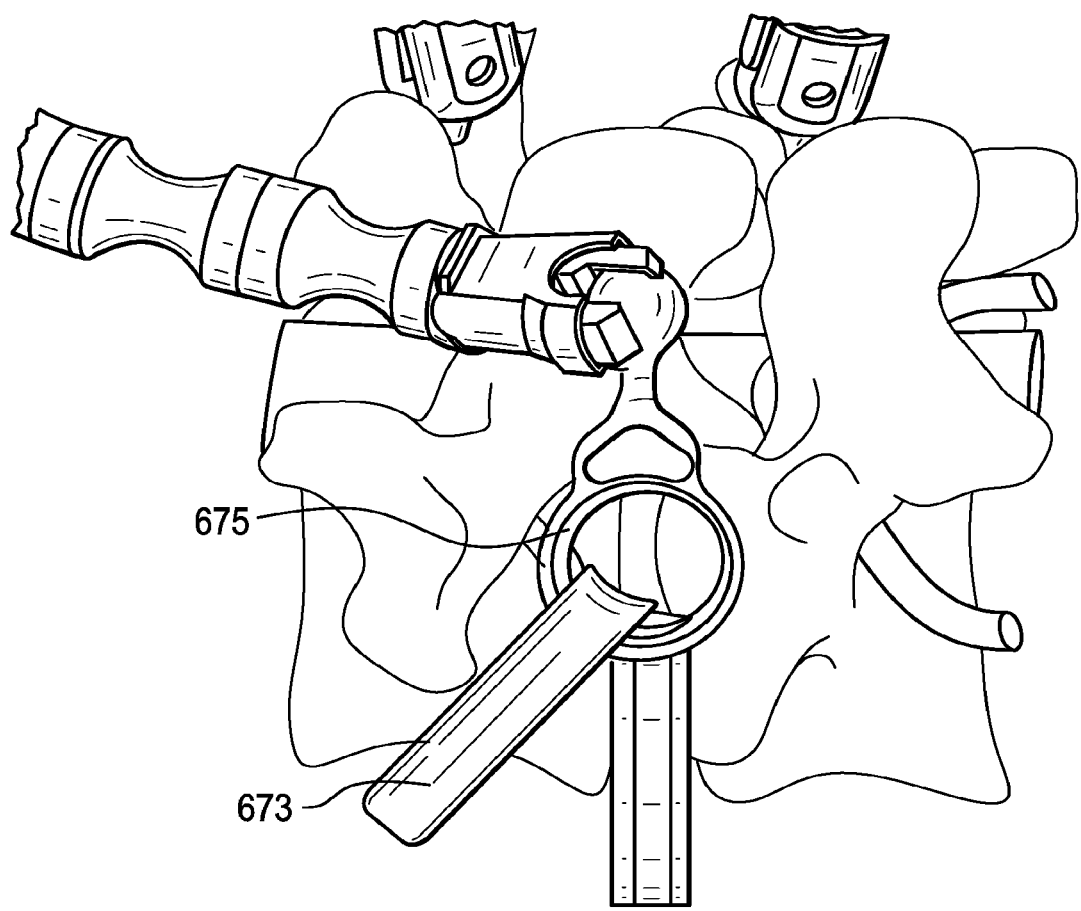
Figure 82:
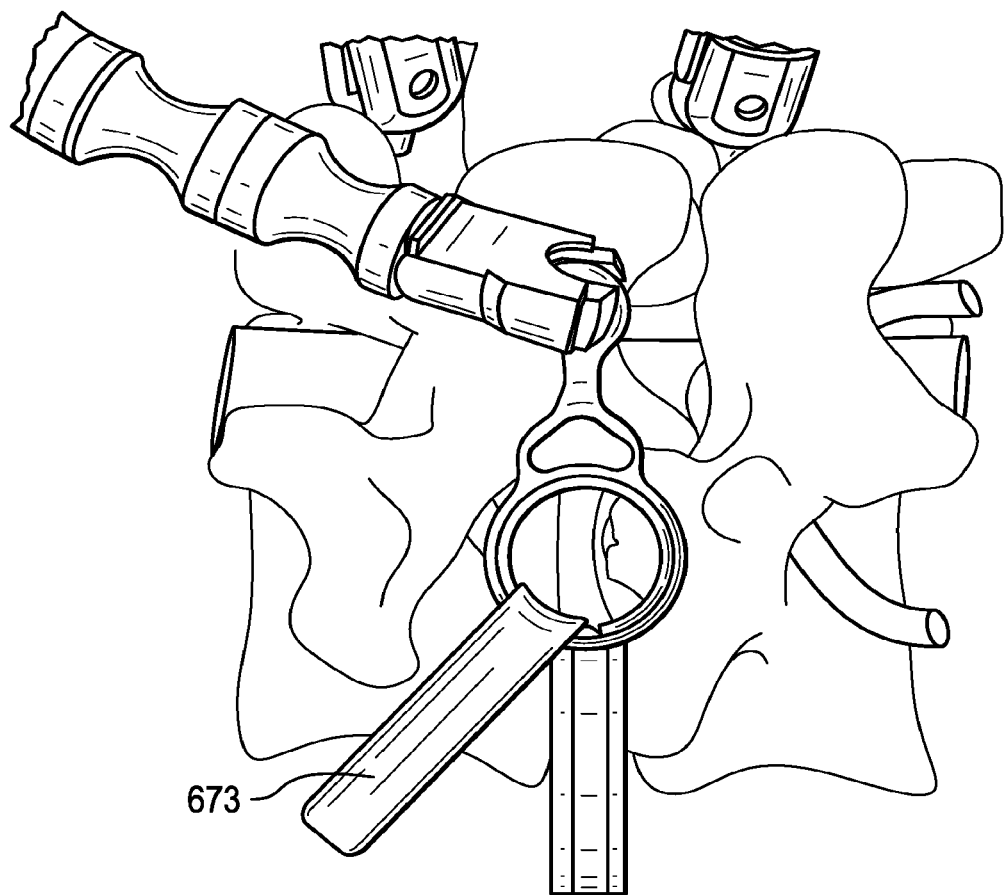

FIGS. 81-82 disclose Soft tissue retraction, showing a clip directly on access tube, medial to lateral retraction. FIG. 81 shows the Soft Tissue Retractor 673 before radial retraction of the nerve. At this state, the Soft Tissue Retractor is already engaged with the Access Tube 675. FIG. 82 discloses the Soft Tissue Retractor 673 after radial retraction of the nerve.

Figure 83:
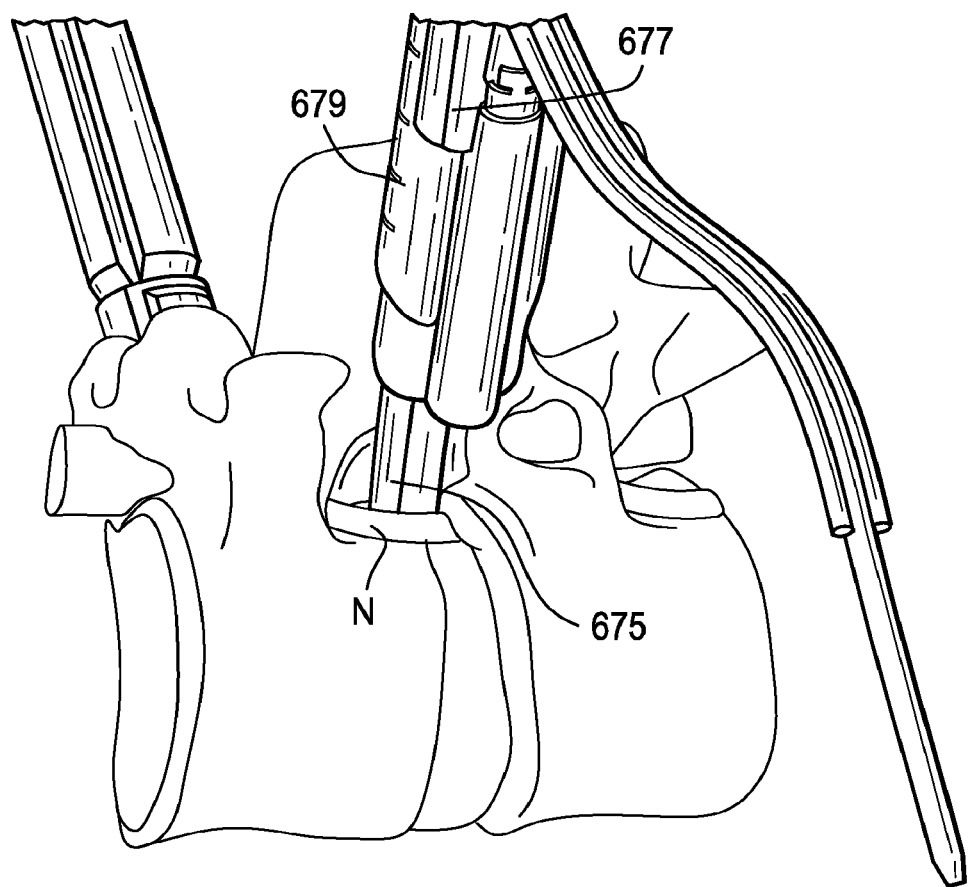

FIG. 83 discloses nerve Shielding and Positioning according patient anatomy. FIG. 83 shows the fully engaged Soft Tissue Retractor 675 with a Clip 677 holding it on the proximal outer Tube 679 of the Telescopic Access Tube. The nerve N is fully retracted and protected by the Soft Tissue Retractor.

Step 6 Disc Removal

Figure 84:
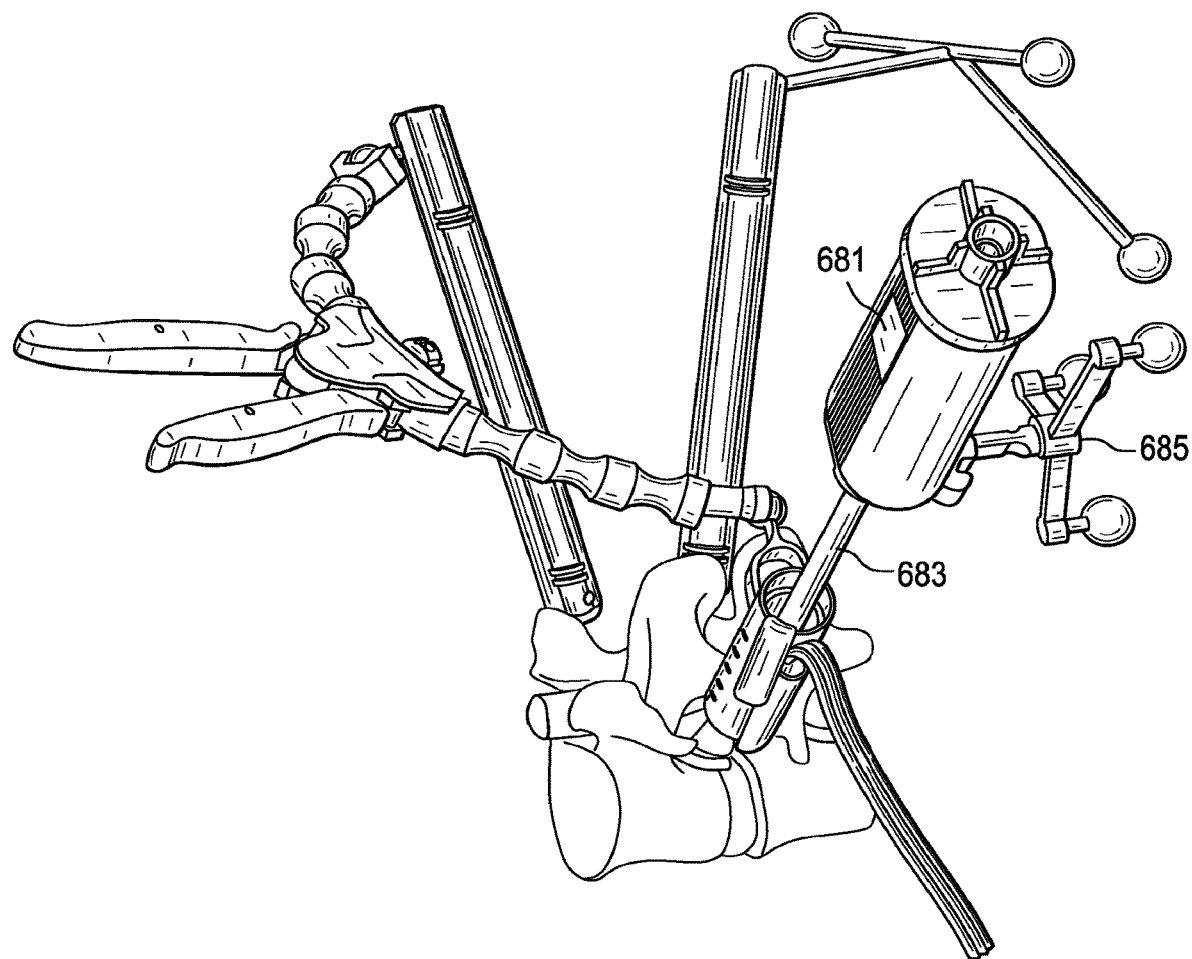
Figure 85:
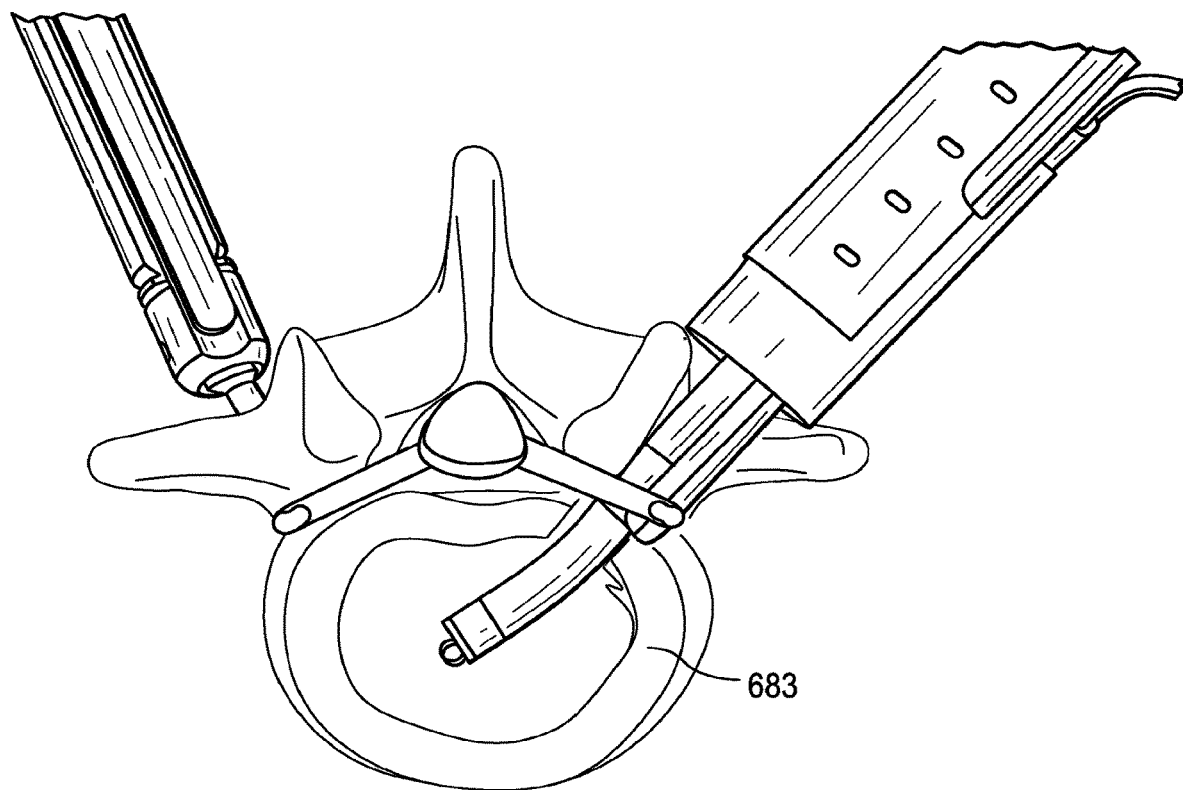

Now referring to FIGS. 84-85, disc clearing is performed with a suction-based discectomy tool 681 that holds the option to be navigated. Therefore there is a ring (not visible) mounted (welded/glued) on the shaft 683 of the discectomy tool that allows a play free mounting of a Navigation Array 685.

Step 7 Cage Insertion

Figure 86:
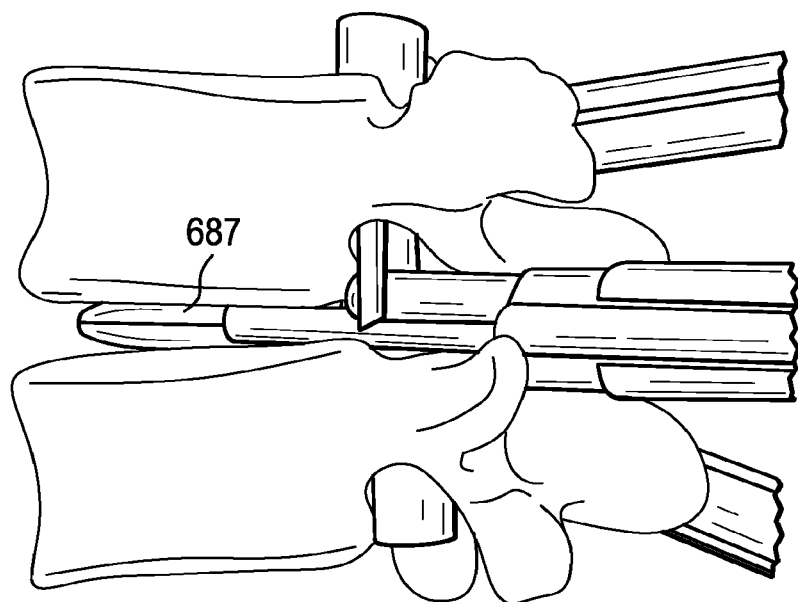
Figure 87:
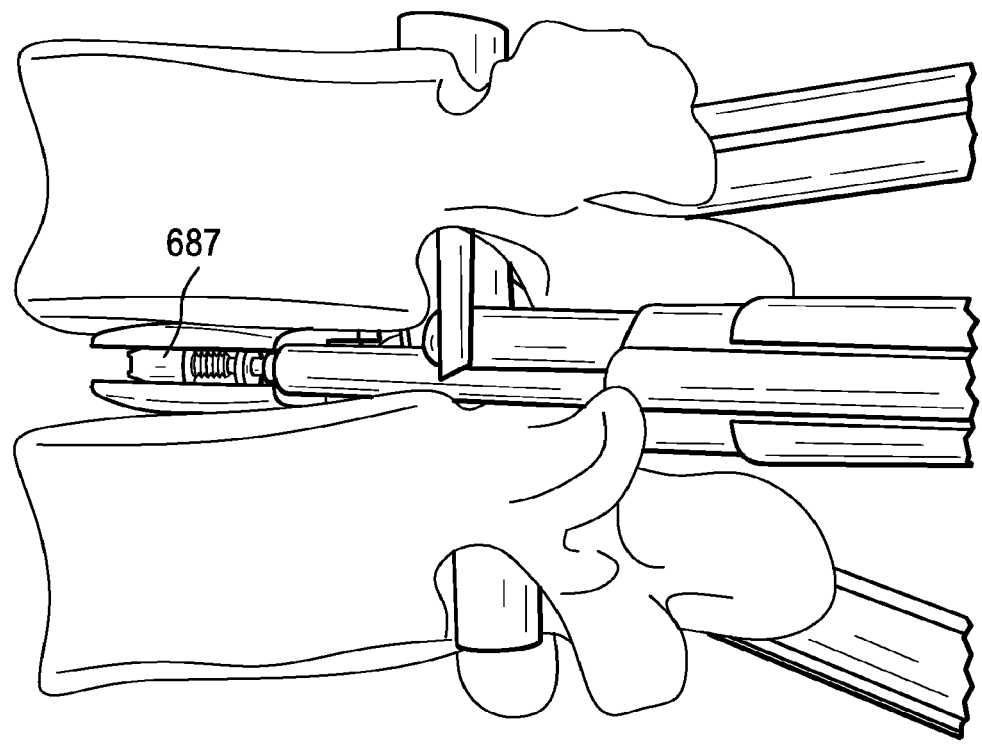

In FIG. 86 an expandable cage 687 is inserted into the disc space. In FIG. 87, the cage 687 is expanded to full expansion.

Figure 88:
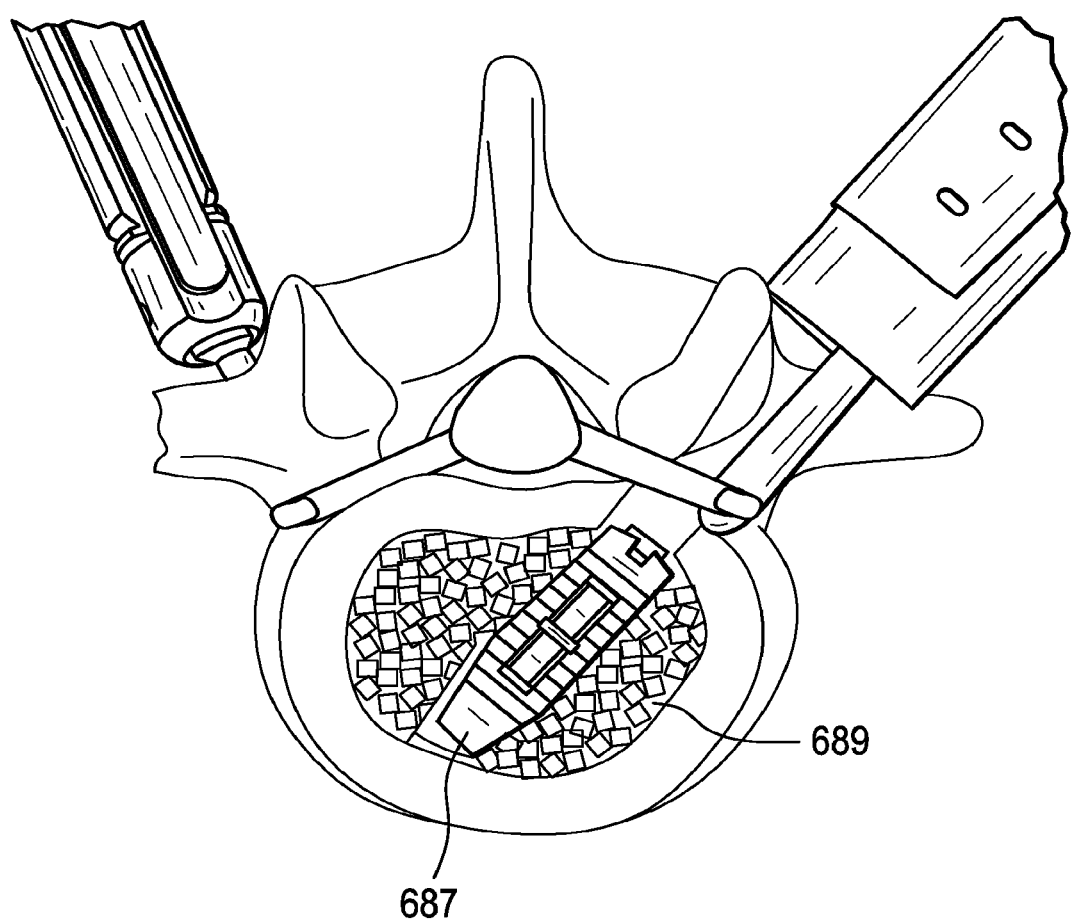

Now referring to FIG. 88, Bone graft 689 is inserted around the cage via a delivery system. The Expandable cage 687 is in its final position before detaching the Inserter. Bone Substitute 689 has been placed around the device (before and after inserting the cage) to ensure a proper fusion process.

Step 8 Posterior Fixation

Figure 89:
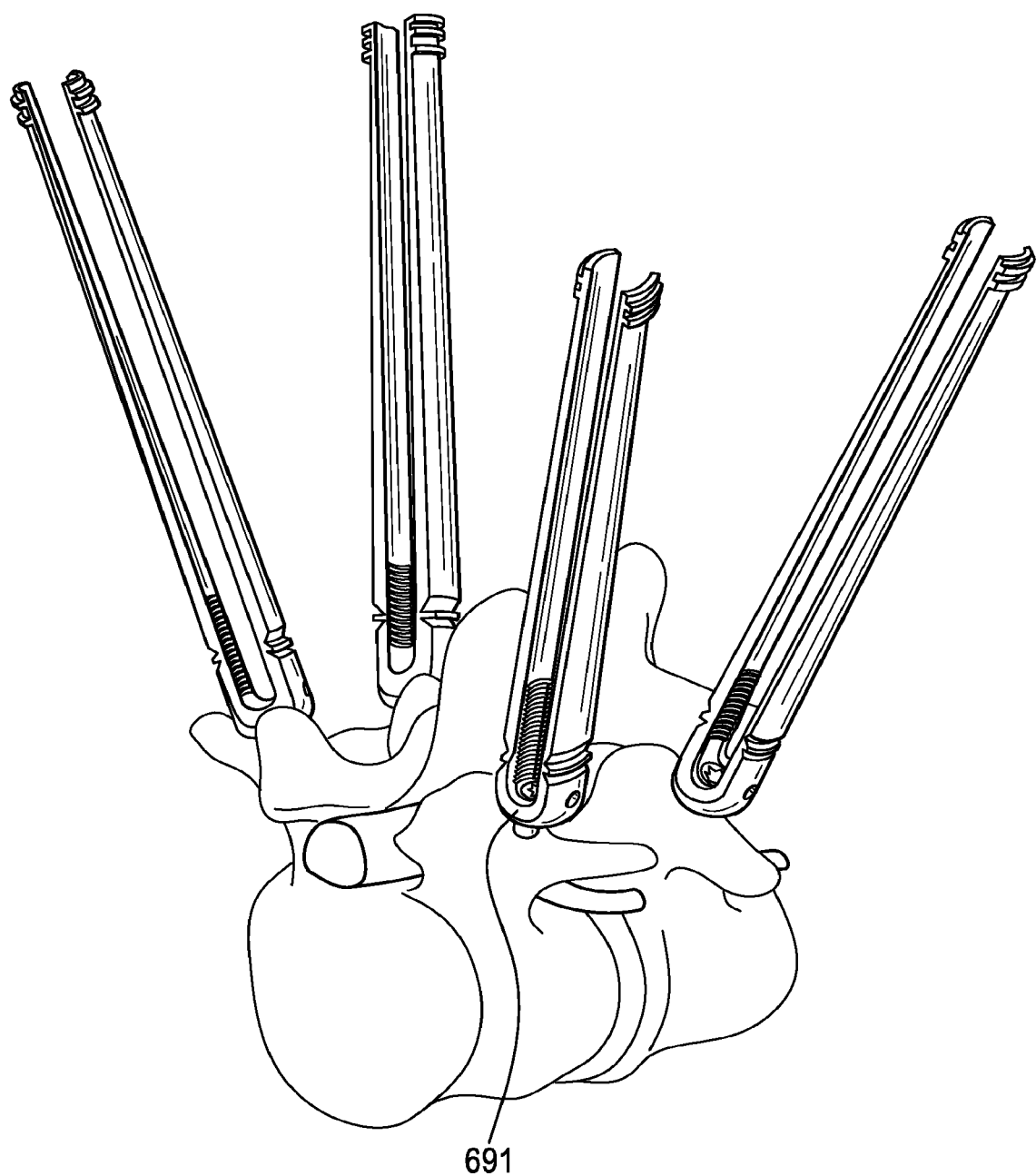
Figure 90:
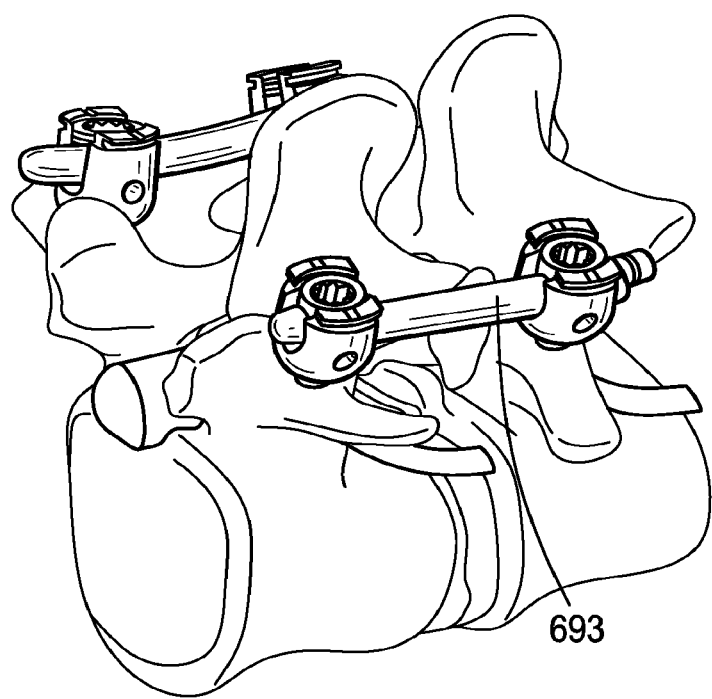

FIG. 89 discloses inserting the remaining screws 691, while FIG. 90 discloses placing rods 693 and fixing the construct.

The invention claimed is:

1. A method of accessing a surgical site in a patient, comprising:
    making an incision in a skin of the patient;
    percutaneously inserting through the incision a multi-tool having a main body, the main body comprising a handle and a shaft extending from the handle, the shaft comprising a sensor;
    navigating insertion of the multi-tool using a navigation array coupled to the main body of the multi-tool;
    detecting at least one of the presence, proximity, health, or other attributes of nerve tissue using the sensor;
    after the detecting, removing the handle from the shaft;
    after the removing, inserting one or more dilators over the shaft of the main body of the multi-tool to dilate the incision;
    inserting an access device percutaneously through the dilated incision to position a distal end of the access device at the surgical site; and
    removing the one or more dilators and the main body from a working channel of the access device.

2. The method of claim 1, further comprising after navigating insertion of the multi-tool, delivering energy to a target tissue using an energy delivery element of the multi-tool.

3. The method of claim 2, wherein delivering the energy comprises ablating osseous bone tumor tissue.

4. The method of claim 1, wherein the dilators are inserted over the main body while the navigation array is coupled to the main body.

5. The method of claim 1, further comprising adjusting a length of the access device.

6. The method of claim 5, wherein the access device is telescopically expandable.

7. The method of claim 1, further comprising inserting a camera through the access device.

8. The method of claim 1, wherein the access device includes an outer shield having a substantially tubular shape, and an inner shield movably coupled to the outer shield to retract or shield nerve tissue.

9. The method of claim 1, wherein the navigating insertion of the multi-tool further comprises using the navigation array of the multi-tool to navigate:
    a blunt-tipped probe inserted through the main body,
    a sharp-tipped Jamshidi needle inserted through the main body,
    the one or more dilator tubes, and
    the access device.

10. The method of claim 9, wherein navigation of said components is performed using a single navigation array and using a single registration.

11. The method of claim 9, wherein at least one of the blunt-tipped probe or the sharp-tipped Jamshidi needle comprises a proximal end element configured to prevent detachment of the handle from the shaft of the main body when fully inserted though the shaft of the main body.

12. The method of claim 11, wherein a proximal end of the handle includes a recess configured to receive at least a portion of a thickness of the proximal end element while exposing opposite sides of the proximal end element.

13. The method of claim 11, wherein the handle is configured to expose at least a portion of the proximal end element when the respective sharp-tipped needle or blunt-tipped mandarin is fully inserted though the main body.

* * * * *